Figure 3:
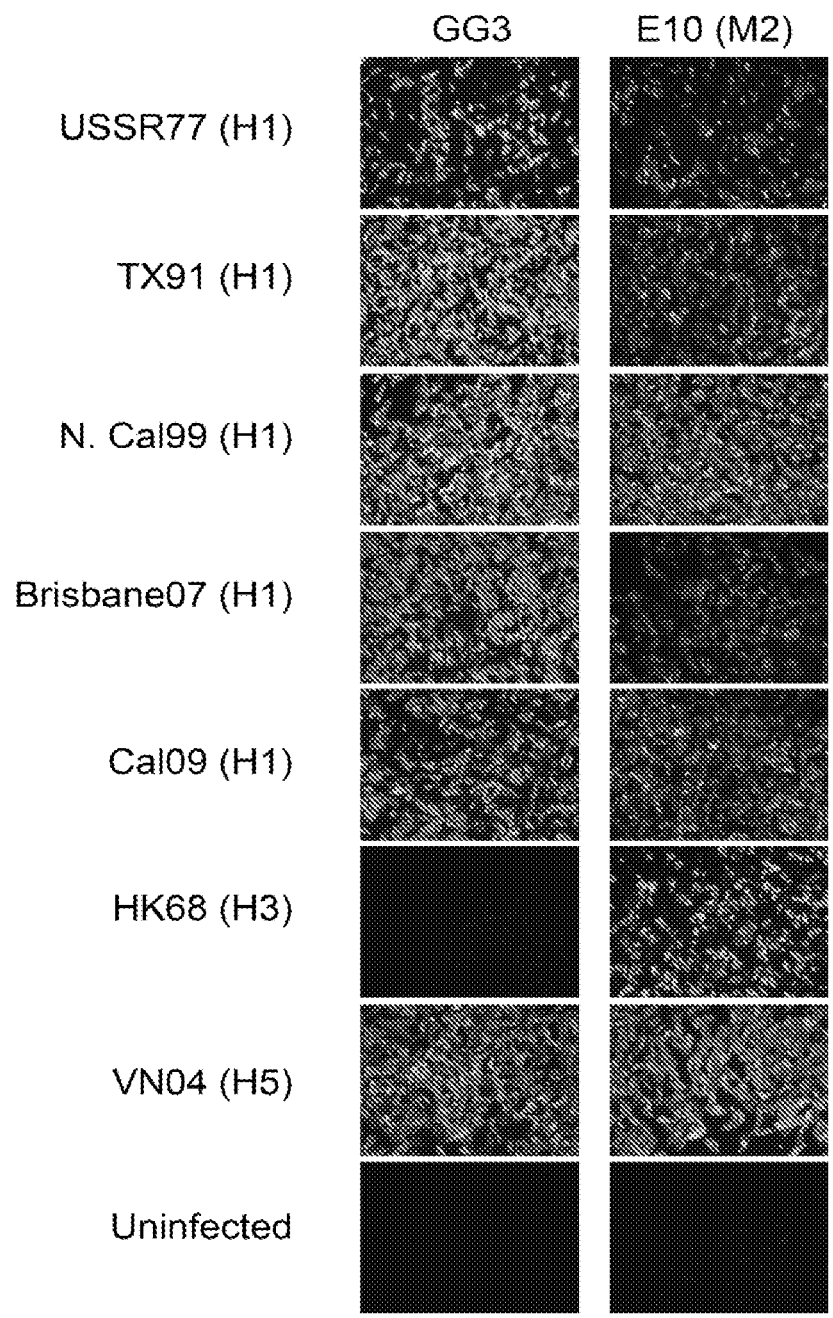

(12) United States Patent
Palese et al.

(10) Patent No.: US 9,908,930 B2
(45) Date of Patent: Mar. 6, 2018

(54) ANTIBODIES AGAINST INFLUENZA VIRUS HEMAGGLUTININ AND USES THEREOF

(71) Applicant: ICAHN SCHOOL OF MEDICINE AT MOUNT SINAI, New York, NY (US)

(72) Inventors: Peter Palese, New York, NY (US); Adolfo Garcia-Sastre, New York, NY (US); Gene Tan, New York, NY (US)

(73) Assignee: ICAHN SCHOOL OF MEDICINE AT MOUNT SINAI, New York, NY (US)

(*) Notice: Subject to any disclaimer, the term of this patent is extended or adjusted under 35 U.S.C. 154(b) by 27 days.

(21) Appl. No.: 14/774,893

(22) PCT Filed: Mar. 13, 2014

(86) PCT No.: PCT/US2014/025526
§ 371 (c)(1),
(2) Date: Sep. 11, 2015

(87) PCT Pub. No.: WO2014/159960
PCT Pub. Date: Oct. 2, 2014

(65) Prior Publication Data
US 2016/0137721 A1    May 19, 2016

Related U.S. Application Data

(60) Provisional application No. 61/783,532, filed on Mar. 14, 2013.

(51) Int. Cl.
| C07K 16/10 | (2006.01) |
| G01N 33/53 | (2006.01) |
| G01N 33/569 | (2006.01) |
| A61K 47/68 | (2017.01) |
| A61K 39/00 | (2006.01) |

(52) U.S. Cl.
CPC ...... *C07K 16/1018* (2013.01); *A61K 47/6841* (2017.08); *G01N 33/56983* (2013.01); *A61K 2039/505* (2013.01); *C07K 2317/33* (2013.01); *C07K 2317/565* (2013.01); *C07K 2317/76* (2013.01); *C07K 2319/00* (2013.01); *G01N 2333/11* (2013.01); *G01N 2469/10* (2013.01)

(58) Field of Classification Search
None
See application file for complete search history.

(56) References Cited

U.S. PATENT DOCUMENTS

| 5,182,192 A | 1/1993 | Steplewski et al. |
| 5,413,923 A | 5/1995 | Kucherlapati et al. |
| 5,545,806 A | 8/1996 | Lonberg et al. |
| 5,569,825 A | 10/1996 | Lonberg et al. |
| 5,571,709 A | 11/1996 | Devauchelle et al. |
| 5,573,916 A | 11/1996 | Cheronis et al. |
| 5,589,174 A | 12/1996 | Okuno et al. |
| 5,625,126 A | 4/1997 | Lonberg et al. |
| 5,631,350 A | 5/1997 | Okuno et al. |
| 5,633,425 A | 5/1997 | Lonberg et al. |
| 5,661,016 A | 8/1997 | Lonberg et al. |
| 5,820,871 A | 10/1998 | Palese et al. |
| 5,854,037 A | 12/1998 | Palese et al. |
| 5,885,793 A | 3/1999 | Griffiths et al. |
| 5,916,771 A | 6/1999 | Hori et al. |
| 6,001,634 A | 12/1999 | Palese et al. |
| 6,165,476 A | 12/2000 | Strom et al. |
| 6,337,070 B1 | 1/2002 | Okuno et al. |
| 6,720,409 B2 | 4/2004 | Okuno et al. |
| 6,867,293 B2 | 3/2005 | Andrews et al. |
| 6,887,699 B1 | 5/2005 | Palese et al. |
| 6,942,861 B2 | 9/2005 | McKee et al. |
| 8,367,077 B2 | 2/2013 | Zurbriggen et al. |
| 8,603,467 B2 | 12/2013 | Chen et al. |
| 8,673,314 B2 | 3/2014 | Garcia Sastre et al. |
| 8,828,406 B2 | 9/2014 | Garcia-Sastre et al. |
| 9,051,359 B2 | 6/2015 | Garcia-Sastre et al. |
| 9,175,069 B2 | 11/2015 | Garcia-Sastre et al. |
| 9,371,366 B2 | 6/2016 | Garcia-Sastre et al. |
| 9,452,211 B2 | 9/2016 | Meijberg et al. |
| 9,701,723 B2 | 7/2017 | Garcia-Sastre et al. |
| 9,708,373 B2 | 7/2017 | Garcia-Sastre et al. |
| 2002/0164770 A1 | 11/2002 | Hoffman |
| 2003/0134338 A1 | 7/2003 | Makarocskiy |

(Continued)

FOREIGN PATENT DOCUMENTS

| CA | 2121559 | 10/1994 |
| CA | 2121559 A1 | 10/1994 |

(Continued)

OTHER PUBLICATIONS

Sparrow et al., Vaccine, 2016, 34:5442-5448.*
Babai et al., "A novel liposomal influenza vaccine (Influsome-VAC) containing hemagglutinin-neuraminidase and IL-2 or GM-CSF induces protective anti-neuraminidase antibodies cross-reacting with a wide spectrum of influenza A viral strains." Vaccine.; 20(3-4);505-15, (2001).
Babu et al., 2014, "Live attenuated H7N7 influenza vaccine primes for a vigorous antibody response to inactivated H7N7 influenza vaccine," Vaccine, 32:6798-6804.
Berry, 2007, "Cross-reactive MAb to the binding domain of botulinum neurotoxin A, B, and E developed using a sequential immunization strategy: anti-botulinum neurotoxin", Hybridoma, 26(6).
Bianch

(56) References Cited

U.S. PATENT DOCUMENTS

| | | |
|---|---|---|
| 2004/0002061 A1 | 1/2004 | Kawaoka |
| 2005/0009008 A1 | 1/2005 | Robinson et al. |
| 2005/0048074 A1 | 3/2005 | Cardineau et al. |
| 2005/0064391 A1 | 3/2005 | Segal et al. |
| 2005/0106178 A1 | 5/2005 | O'hagan et al. |
| 2005/0201946 A1 | 9/2005 | Friede et al. |
| 2006/0008473 A1 | 1/2006 | Yana et al. |
| 2006/0280754 A1 | 12/2006 | Garry et al. |
| 2007/0020238 A1 | 1/2007 | Baltimore et al. |
| 2007/0036809 A1 | 2/2007 | Michl et al. |
| 2008/0019998 A1 | 1/2008 | Wang et al. |
| 2008/0032921 A1 | 2/2008 | Alexander et al. |
| 2008/0152657 A1 | 6/2008 | Horowitz et al. |
| 2008/0176247 A1 | 7/2008 | Chou et al. |
| 2009/0081255 A1 | 3/2009 | Bublot et al. |
| 2009/0291472 A1 | 11/2009 | Lu et al. |
| 2009/0304730 A1 | 12/2009 | Amon et al. |
| 2009/0304739 A1 | 12/2009 | Rappouli et al. |
| 2009/0311265 A1 | 12/2009 | Van Den Brink et al. |
| 2009/0311669 A1 | 12/2009 | Kawaoka |
| 2010/0297165 A1 | 11/2010 | Berzofsky et al. |
| 2010/0297174 A1 | 11/2010 | Garcia-Sastre et al. |
| 2011/0027270 A1 | 2/2011 | Garcia-Sastre et al. |
| 2011/0111494 A1 | 5/2011 | Hill et al. |
| 2011/0182938 A1 | 7/2011 | Weiner et al. |
| 2012/0039898 A1 | 2/2012 | Throsby et al. |
| 2012/0122185 A1 | 5/2012 | Palese et al. |
| 2012/0189658 A1 | 7/2012 | Couture et al. |
| 2012/0244183 A1 | 9/2012 | Garcia-Sastre et al. |
| 2013/0129747 A1 | 5/2013 | Schrader |
| 2013/0129761 A1 | 5/2013 | Garcia-Sastre et al. |
| 2013/0209499 A1 | 8/2013 | Garcia-Sastre et al. |
| 2014/0170163 A1 | 6/2014 | Garcia Sastre et al. |
| 2014/0328875 A1 | 11/2014 | Garcia Sastre et al. |
| 2015/0132330 A1 | 5/2015 | Garcia-Sastre et al. |
| 2015/0239960 A1 | 8/2015 | Garcia-Sastre et al. |
| 2015/0297712 A1 | 10/2015 | Garcia-Sastre et al. |
| 2015/0335729 A1 | 11/2015 | Garcia-Sastre et al. |
| 2016/0355553 A1 | 12/2016 | Meijberg et al. |
| 2016/0361408 A1 | 12/2016 | Garcia-Sastre et al. |
| 2016/0362455 A1 | 12/2016 | Meijberg et al. |
| 2016/0376347 A1 | 12/2016 | Saelens et al. |

FOREIGN PATENT DOCUMENTS

| | | |
|---|---|---|
| CA | 2718923 | 9/2009 |
| EP | 0621339 A2 | 10/1994 |
| JP | 2004-258814 | 9/2004 |
| JP | 2006-347922 | 12/2006 |
| JP | 2011-057653 A | 3/2011 |
| WO | WO 1984/000687 | 3/1984 |
| WO | WO 1992/001047 | 1/1992 |
| WO | WO 1994/009136 | 4/1994 |
| WO | WO 1994/016109 | 7/1994 |
| WO | WO 1994/017826 | 8/1994 |
| WO | WO 1995/034324 | 12/1994 |
| WO | WO 1996/033735 | 10/1996 |
| WO | WO 1996/034096 | 10/1996 |
| WO | 1997/040177 A1 | 10/1997 |
| WO | WO 1998/024893 | 6/1998 |
| WO | WO 2007/045674 | 4/2007 |
| WO | WO 2007/064802 | 6/2007 |
| WO | WO 2007/103322 | 9/2007 |
| WO | WO 2007/134327 | 11/2007 |
| WO | WO 2008/005777 | 1/2008 |
| WO | WO 2008/028946 | 3/2008 |
| WO | WO 2008/032219 | 3/2008 |
| WO | WO 2009/009876 | 1/2009 |
| WO | WO 2009/025770 | 2/2009 |
| WO | WO 2009/036157 | 3/2009 |
| WO | WO 2009/068992 | 6/2009 |
| WO | WO 2009/076778 | 6/2009 |
| WO | WO 2009/079259 | 6/2009 |
| WO | WO 2009/092038 | 7/2009 |
| WO | WO 2009/121004 | 10/2009 |
| WO | WO 2009/150532 | 12/2009 |
| WO | WO 2009/156405 | 12/2009 |
| WO | WO 2010/003235 | 1/2010 |
| WO | WO 2010/036948 | 4/2010 |
| WO | WO 2010/117786 | 10/2010 |
| WO | WO 2010/130636 | 11/2010 |
| WO | WO 2010/138564 | 12/2010 |
| WO | WO 2010/148511 | 12/2010 |
| WO | WO 2011/014645 | 2/2011 |
| WO | WO 2011/044152 | 4/2011 |
| WO | WO 2011/087092 | 7/2011 |
| WO | WO 2011/103453 | 8/2011 |
| WO | WO 2011/111966 | 9/2011 |
| WO | WO 2011/123495 | 10/2011 |
| WO | WO 2012/009790 | 1/2012 |
| WO | WO 2013/043729 | 3/2013 |
| WO | WO 2013/079473 | 6/2013 |
| WO | WO 2014/159960 | 1/2014 |
| WO | WO 2014/099931 | 6/2014 |
| WO | WO 2014/152841 A1 * | 9/2014 |

OTHER PUBLICATIONS

Boni et al., 2010, "Guidelines for identifying homologous recombination events in influenza A virus", PLoS One, 5(5):e10434.

Boni et al., 2012, "No evidence for intra-segment recombination of 2009 H1N1 influenza virus in swine", Gene, 494(2):242-245.

Bowie, et al., 1990, "Deciphering the Message in Protein Sequences: Tolerance to Amino Acid Substitutions." Science, 247: 1306-1310.

Bullough et al., 1994, "Structure of influenza haemagglutinin at the pH of membrane fusion." Nature, 371:37-43.

Casali et al., 2008, "Site-directed mutagenesis of the hinge peptide from the hemagglutinin protein: enhancement of the pH-responsive conformational change." Protein Engineering Design & Selection, 21(6):395-404.

Chen et al., 1999, "N- and C-terminal residues combine in the fusion-pH influenza hemagglutinin HA2 subunit to form an N cap that terminates the triple-stranded coiled coil." Proc. Natl. Acad Sci., 91:8967-8972.

Chen et al., 2007, "Influenza Virus Hemagglutinin and Neuraminidase, but Not the Matrix Protein, are Required for Assembly and Budding of Plasmid-Derived Virus-Like Particles", J. Virol. 81(13):7111-7123.

Chen et al., 2010, "Generation of Live Attenuated Novel Influenza Virus A/California/7/09 (H1N1) Vaccines with High Yield in Embryonated Chicken Eggs." J. Virol. 84(1):44-51.

Chen et al., 2011, "Vaccine design of hemagglutinin glycoprotein against influenza", Trends in Biotechnology, 29(9):426-434.

Chen et al., 2016, "Influenza A viruses expressing intra- or intergroup chimeric hemagglutinins", doi:10.1128/JVI.03060-15.

Clementi et al., 2011, "A Human Monoclonal Antibody with Neutralizing Activity against Highly Divergent Influenza Subtypes". PLoS One, 6(12):e28001.

Copeland et al., 2005, "Functional chimeras of human immunodeficiency virus type 1 Gp120 and influenza A virus (H3) hemagglutinin", Journal of Virology; 79:6459-6471.

Corti et al., 2011, "A neutralizing antibody selected from plasma cells that binds to group 1 and group 2 influenza A hemagglutinins", Science. 333(6044):850-856.

Cotter et al., 2014, "A Single Amino Acid in the Stalk Region of the H1N1pdm Influenza Virus HA Protein Affects Viral Fusion, Stability and Infectivity." PLoS Pathogens, 10(1):e1003831.

D'Aoust et al., 2008, "Influenza virus-like particles produced by transient expression in Nicotiana benthaminana induce a protective immune response against a lethal viral challenge in mice", J. Plant Biotechnology, 6(9):930-940.

D'Aoust et al., 2010, "The production of hemagglutinin-based virus-like particles in plants: a rapid, efficient and safe response to pandemic influenza", Plant Biotechnology, 8(5):607-619.

Das et al., 2010, "Glycosylation Focuses Sequence Variation in the Influenza A Virus H1 Hemagglutinin Globular Domain." PLoS Pathogens, 6(11):e1001211.

Database Geneseq "Influenza A virus hemagglutinin protein, 1-11PR8", Accession No. AJG95109, dated Nov. 15, 2007.

(56) References Cited

OTHER PUBLICATIONS

Database GenPept "Hemagglutinin precursor [Contains: Hemagglutinin HA1 chain; Hemagglutinin HA2 chain]", Accession No. P03437, dated Jul. 21, 1986.
Dillon et al., 1992, "Induction of protective class I MHC-restricted CTL in mice by a recombinant influenza vaccine in aluminum hydroxide adjuvant", Vaccine, 10(5):309-318.
Doms RW & Moore JP, 2000, "HIV-1 Membrane Fusion: Targets of Opportunity," JCB, 151(2): F9-F13.
Doyle et al., 1986, "Analysis of Progressive Deletions of the Transmembrane and Cytoplasmic Domains of Influenza Hemagglutinin", JCB, 103:1193-1204.
Dunand et al., 2016, "Both Neutralizing and Non-Neutralizing Human H7N9 Influenza Vaccine-Induced Monoclonal Antibodies Confer Protection," Cell Host & Microbe, 19:1-14.
Eda et al., 2006, "Sequential immunization with V3 peptides from primary human immunodeficiency virus type 1 produces cross-neutralizing antibodies against primary isolates with a matching narrow-neutralization sequence motif" J Virol, 80(11):5552-5562.
Ekiert et al., 2009, "Antibody recognition of a highly conserved influenza virus epitope", Science; 324(5924):246-251.
Ekiert et al., 2011, "A highly conserved neutralizing epitope on group 2 influenza A viruses", Science 333:843-850.
Ekiert et al., 2012, "Cross-neutralization of influenza A viruses mediated by a single antibody loop", Nature, 489:526-532.
Flandorfer et al., 2003, "Chimeric Influenza A Viruses with a Functional Influenza B Virus Neuraminidase or Hemagglutinin", J. Virol., 77(17):9116-9123.
Fluzone®, 2009-2010 Fluzone Seasonal influenza vaccine package insert, 2009.
Fodor et al., 1999, "Rescue of influenza A virus from recombinant DNA", J Virol 73:9679-9682.
Fujii et al., 2002, "Selective incorporation of influenza virus RNA segments into virions", Proc. Natl. Acad. Sci. USA 100:2002-2007.
Gao & Palese, 2009, "Rewiring the RNAs of influenza virus to prevent reassortment", PNAS 106:15891-15896.
Gao et al., 2013, "Human infection with a novel avian-origin influenza A(H7N9) virus", N. Engl. J. Med. 368:1888-1897.
García-Sastre et al., 1994, "Introduction of foreign sequences into the genome of influenza A virus", Dev. Biol. Stand, 82:237-246.
García-Sastre et al., 1994, "Use of a mammalian internal ribosomal entry site element for expression of a foreign protein by a transfectant influenza virus", J. Virol. 68:6254-6261.
Genbank, NCBI Reference Sequence: YP_163736.1, HA2 [Influenza A virus (A/Puerto Rico/8/1934(H1N1))].
Gerhard et al., 2006, "Prospects for universal influenza virus vaccine", Emerging Infectious Diseases; 12(4):569-574.
Gibbs et al., 2001, "Recombination in the hemagglutinin gene of the 1918 Spanish Flu". Science, 293(5536):1842-1845.
Giddings et al., 2000, "Transgenic plants as factories for biopharmaceuticals", Nature Biotechnology, 18:1151-1155.
Gocnik et al., 2008, "Antibodies Induced by the HA2 Glycopolypeptide of Influenza Virus Haemagglutinin Improve Recovery from Influenza A Virus Infection," J Gen Virol., 89:958-967.
Goff et al., 2013, "Adjuvants and immunization strategies to induce influenza virus hemagglutinin stalk antibodies", PLoS One 8:e79194.
Gomord et al., 2005, "Biopharmaceutical production in plants: problems, solutions and opportunities." TRENDS in Biotechnology, 23(11):559-565.
Gould et al., 1987, "Mouse H-2k-Restricted Cytotoxic T Cells Recognize Antigenic Determinants in Both the HA1 and HA2 Subunits of the Influenza A/PR/8/34 Hemagglutinin," J. Exp. Med., 166:693-701.
Graham et al., 2013, "DNA Vaccine Delivered by a Needle-Free Injection Device Improves Potency of Priming for Antibody and CD8+ TCell Responses after rAd5 Boost in a Randomized Clinical Trial," PLoS One, 8(4): 1-11, e59340.
Graves et al., 1983, "Preparation of influenza virus subviral particles lacking the HAI subunit of hemagglutinin: unmasking of cross-reactive HA2 determinants," Virology, 126(1):106-1 16).
Hai et al., 2008, "Influenza B virus NS1-truncated mutants: live-attenuated vaccine approach", J Virol 82:10580-10590.
Hai et al., 2011, "A reassortment-incompetent live attenuated influenza virus vaccine for protection against pandemic virus strains", Journal of virology 85:6832-6843.
Hai et al., 2012, "Influenza viruses expressing chimeric hemagglutinins: globular head and stalk domains derived from different subtypes", J. Virol. 86:5774-5781.
Hallily et al., 2015, "High-Affinity H7 Head and Stalk Domain-Specific Antibody Response to an Inactivated Influenza H7N7 Vaccine After Priming With Live Attenuated Influenza Vaccine," Journal of Infectious Diseases, 212: 1270-1278.
Haynes, 2009, "Influenza virus-like particle vaccines", Expert Rev. Vaccines, 8(4): 435-445.
Horimoto et al., "Generation of influenza A viruses with chimeric (type A/B) hemagglutinins." J.Virol. Jul. 2003;77(14):8031-8038.
Horimoto et al., 2004, "Influenza A viruses possessing type B hemagglutinin and neuraminidase: potential as vaccine components." Microbes and Infection, 6(6): 579-583.
Horvath et al., 1998, "Hemagglutinin-based multipeptide construct elicits enhanced protective immune response in mice against influenza A virus infection", Immunology Letters; 60(2/03):127-136.
Igarashi et al.: 2008, "Genetically destined potentials for N-linked glycosylation of influenza virus hemagglutinin" Virology, 376:323-329.
Impagliazzo et al., 2015, "A stable trimeric influenza hemagglutinin stem as a broadly protective immunogen." Science, 349(6254):1301-1306.
International Search Report dated Feb. 19, 2013 for PCT Application No. PCT/US2012/056122, Published as WO 2013/043729.
International Search Report dated Apr. 28, 2014 of PCT Application No. PCT/US2013/075697, Published as WO 2014/099931.
International Search Report dated Jun. 26, 2014 for PCT Application No. PCT/US2014/025526, Published as WO 2014/149960.
International Search Report dated Jul. 13, 2011 of PCT Application No. PCT/US2011/030441, Published as WO 2011/123495.
International Search Report dated Aug. 24, 2010 or PCT Application No. PCT/US2010/029202, Published as WO 2010/117786.
International Search Report of International application No. PCT/US20011/025467, dated Oct. 19, 2011.
International Search Report of International application No. PCT/US2010/036170, dated Aug. 17, 2010.
Kanekiyo et al., 2013, "Self-assembling influenza nanoparticle vaccines elicit broadly neutralizing H1N1 antibodies." Nature, 499(7456):102-6.
Kashyap et al., 2008, "Combinatorial antibody libraries from survivors of the Turkish H5N1 avian influenza outbreak reveal virus neutralization strategies", Proc Natl Acad Sci USA; 105:5986-5991.
Kaverin et al., 2004, "Structural Differences Among Hemagglutinins of Influenza A Virus Subtypes Are Reflected in Their Antigenic Architecture: Analysis of H9 Escape Mutants", Journal of Virology, 78(1):240-249.
Khurana et al., 2013, "DNA Priming Prior to Inactivated Influenza A(H5N1) Vaccination Expands the Antibody Epitope Repertoire and Increases Affinity Maturation in a Boost-Interval-Dependent Manner in Adults," Journal of Infectious Disease, 208:413-417.
Kistner et al.. 2007, "Cell culture (Vero) derived whole virus (H5N1) vaccine based on wild-type virus strain induces cross-protective immune responses", Vaccine; 25(32):6028-6036.
Krammer et al., 2010, "Trichoplusia ni cells (High Five) are highly efficient for the production of influenza A virus-like particles: a comparison of two insect cell lines as production platforms for influenza vaccines", Mol Biotechnol; 45:226-34.
Krammer et al., 2012, "A carboxy-terminal trimerization domain stabilizes conformational epitopes on the stalk domain of soluble recombinant hemagglutinin substrates", PLoS One. 7:e43603. doi:10.1371/journal.pone .0043603.
Krammer et al., 2012, "Hemagglutinin stalk-reactive antibodies are boosted following sequential infection with seasonal and pandemic H1N1 influenza virus in mice", J Virol, 86:10302-10307.

(56) References Cited

OTHER PUBLICATIONS

Krammer et al., 2013, "Chimeric hemagglutinin influenza virus vaccine constructs elicit broadly protective stalk-specific antibodies", J. Virol. 87:6542-6550.
Krammer et al., 2013, "Influenza virus hemagglutinin stalk-based antibodies and vaccines", Current Opinion in Virology 3:521-530.
Krammer et al., 2014, "Assessment of influenza virus hemagglutinin stalk-based immunity in ferrets", J Virol, 88:3432-3442.
Krammer et al., 2014, "H3 stalk-based chimeric hemagglutinin influenza virus constructs protect mice from H7N9 challenge", J Virol, 88:2340-2343.
Krammer, 2015, "The quest for a universal flu vaccine: headless HA 2.0", Cell Host Microbe, 18:395-397.
Krammer, 2016, "Novel universal influenza virus vaccine approaches", Current Opinion in Virology, 17:95-103.
Krause et al., 2011, "A broadly neutralizing human monoclonal antibody that recognizes a conserved, novel epitope on the globular head of the influenza H1N1 virus hemagglutinin", J. Virol., 85(20):10905-10908.
Krause et al., 2012, "Human monoclonal antibodies to pandemic 1957 H2N2 and pandemic 1968 H3N2 influenza viruses", J. Virol. 86:6334-6340.
Landry et al., 2008, "Three-dimensional structure determines the pattern of CD4+ T-cell epitope dominance in influenza virus hemagglutinin", Journal of Virology; 82(3):1238-1248.
Landry et al., 2010, "Preclinical and Clinical Development of Plant-Made Virus-Like Particle Vaccine against Avian H5N1 Influenza", PLoS One, 5(12): e15559.
Lebendiker M. "Purification Protocols." The Wolfson Centre for Applied Structural Biology, http://wolfson.huji.ac.il/purification/Purification_Protocols.html. Apr. 5, 2006.
Ledgerwood, et al., 2013, "Prime-Boost Interval Matters: A Randomized Phase 1 Study to Identify the Minimum Interval Necessary to Observe the H5 DNA Influenza Vaccine Priming Effect," Journal of Infectious Diseases, 208:418-422.
Lee et al. 2012, "Heterosubtypic antibody recognition of the influenza virus hemagglutinin receptor binding site enhanced by avidity", Proc. Natl. Acad. Sci. U.S.A. 109:17040-17045.
Leroux-Roels, et al. 2008. "Broad Glade 2 cross-reactive immunity induced by an adjuvanted Glade 1 rH5N1 pandemic influenza vaccine", PLOS One; 3(2):1-5.
Li et al., 1992, "Influenza A virus transfectants with chimaeric haemagglutinins containing epitopes from different subtypes", Journal of Virology, 67:399-404.
Lorieau, et al., 2010, "The complete influenza hemagglutinin fusion domain adopts a tight helical hairpin arrangement at the lipid:water interface." PNAS, 107(25):11341-11346.
Lowen et al. 2009, "Blocking interhost transmission of influenza virus by vaccination in the guinea pig model", Journal of Virology; 8307):2803-2818.
Lu et al., 2013, "Production and stabilization of the trimeric influenza hemagglutinin stem domain for potentially broadly protective influenza vaccines." PNAS, 111(1):125-130.
Luke et al., 2014, "Improving pandemic H5N1 influenza vaccines by combining different vaccine platforms," Expert Review of Vaccines 13(7):873-883.
Mallajosyula et al., 2014, "Influenza hemagglutinin stem-fragment immunogen elicits broadly neutralizing antibodies and confers heterologous protection." PNAS, 111(25):E2514-23.
Marasco et al.. 2007, "The growth and potential of human antiviral monoclonal antibody therapeutics", Nat Biotechnol: 25(12):1421-1434.
Margine et al., 2013, "H3N2 influenza virus infection induces broadly reactive hemagglutinin stalk antibodies in humans and mice", J. Virol. 87:4728-4737.
Margine et al., 2013, "Hemagglutinin stalk-based universal vaccine constructs protect against group 2 influenza A viruses", J Virol, 10435-10446.

Mbawuike et al., 1994, "Influenza A subtype cross-protection after immunization of outbred mice with purified chimeric NS1/HA2 influenza virus protein", Vaccine, 1994: 12(14):1340-1348.
Mett et al., 2008, "A plant-produced influenza subunit vaccine protects ferrets against virus challenge", Influenza and Other Respiratory Viruses, 2(1):33-40.
Miller et al., 2013, "1976 and 2009 H1N1 influenza virus vaccines boost anti-hemagglutinin stalk antibodies in humans", J. Infect. Dis. 207:98-105.
Mo et al., 2003. "Coexpression of complementary fragments of CIC-5 and restoration of chloride channel function in a Dent's disease mutation", Am J Physiol Cell Physiol; 286:C79-C89.
Mok et al., 2008, "Enhancement of the CD8<+> T cell response to a subdominant epitope respiratory syncytial virus by deletion of an immunodominant epitope", Vaccine: 26(37):4775-4782.
Nachbagauer et al., 2015, "Hemagglutinin stalk immunity reduces influenza virus replication and transmission in ferrets", J. Virol., doi:10.1128/JVI.02481-15.
Neumann et al., 1999, "Generation of influenza A viruses entirely from cloned cDNAs", PNAS 96:9345-9350.
Okuno et al., 1993, "A common neutralizing epitope conserved between the hemagglutinins of influenza A virus H1 and H2 strains," J. Virol., 67(5):2552-2558.
Okuno et al., 1994, "Protection against the mouse-adapted A/FM/1/47 strain of influenza A virus in mice by a monoclonal antibody with cross-neutralizing activity among E11 and H2 strains," J. Virol., 68(1):517-520.
Oshima et al., 2011, "Naturally Occurring Antibodies in Humans Can Neutralize a Variety of Influenza Virus Strains, Including H3, H1, H2, and H5". Journal of Virology, 85(21):11048-11057.
Ott et al., 2000. The Adjuvant MF59: A 10-Year Perspective, p. 211-228. In O'Hagan DT (ed.), Vaccine Adjuvants, vol. 42. Springer.
Palese P & Shaw M (2007). Orthomyxoviridae: The Viruses and Their Replication. In D.M. Knipe, & P.M. Howley (Eds.), Fields Virology (pp. 1647-1689). Philadelphia, PA: Wolters Kluwer Lippincott Williams & Wilkins.
Papanikolopoulou et al., 2004, "Formation of highly stable chimeric trimers by fusion of an adenovirus fiber shaft fragment with the foldon domain of bacteriophage t4 fibritin", J. Biol. Chem. 279(10):8991-8998.
Pica et al., "Hemagglutinin stalk antibodies elicited by the 2009 pandemic influenza virus as a mechanism for the extinction or seasonal H1N1 viruses." Proc Nat Acad Sci U S A. 2012; 109(7):2573-8.
Pleschka et al., 1996, "A plasmid-based reverse genetics system for influenza A virus", J Virol 70:4188-92.
Ponomarenko et al., "B-Cell Epitope Prediction" Chap. 35 in Structural Bioinformatics, 2nd Edition, Gu and Bourne. Editors; 2009 John Wiley & Sons. Inc. pp. 849-879.
Reid et al., Hemagglutinin [Influenza A virus (A/South Carolina/1/1918(H1N1))]. GenBank Acc. No. AAD17229.1. Dep. Oct. 11, 2000.
Roberts el al., 1993, "Role of conserved glycosylation sites in maturation and transport of influenza A virus hemagglutinin." J Virol, 67(6):3048-60.
Robertson, 1987, "Sequence Analysis of the Haemagglutinin of A/Taiwan/1/86, a New Variant of Human Influenza A(H1/N1) Virus," J. Gen. Virol., 68:1205-1208.
Rudenko et al., 2015, "Assessment of immune responses to H5N1 inactivated influenza vaccine among individuals previously primed with H5N2 live attenuated influenza vaccine," Human Vaccines & Immunotherapeutics, 11(12):2839-2848.
Rudikoff et al., 1982, "Single amino acid substitution altering antigen-binding specificity." Proc Nat Acad Sci U S A., 79(6): I 979-83.
Ryder et al., 2016, "Vaccination with VSV-vectored chimeric hemagglutinins protects mice against divergent influenza virus challenge strains", J. Virol., 90(5):2544-2550.
Sagawa et al., 1996, "The immunological activity of a deletion mutant of influenza virus haemagglutinin lacking the globular region", J Gen Virol; 77:1483-1487.

(56) References Cited

OTHER PUBLICATIONS

Salem, 2000, "In vivo acute depletion of CD8(+) T cells before murine cytomegalovirus infection upregulated innate antiviral activity of natural killer cells", Int. J. Immunopharinacol. 22:707-718.
Santak, M., "Old and new ways to combat human influenza virus." Periodicus Biologorum, 2012; 114(2):221-34.
Schneeman et al., 2012, "A Virus-Like Particle That Elicits Cross-Reactive Antibodies to the Conserved Stem of Influenza Virus Hemagglutinin," J. Virol., 86(21): 11686-22697.
Schulze, 1997, "Effects of Glycosylation on the Properites and Functions of Influenza Virus Hemagglutinin", The Journal of Infectious Diseases, 176(S1):S24-S28.
Shoji et al., 2008, "Plant-expressed HA as a seasonal influenza vaccine candidate", Vaccine, 26(23):2930-2934.
Simmons et al., 2007. "Prophylactic and therapeutic efficacy of human monoclonal antibodies against H5N1 Influenza", PLOS Medicine; 4(5):928-936.
Song et al., 2007, "Influenza A Virus Hemagglutinin Protein, H1PR8," GENESEQ, XP002595511.
Stech et al., 2005, "A new approach to an influenza live vaccine: modification of the cleavage site of hemagglutinin", Nature Med. 11(6):683-689.
Steel et al., 2010. "Influenza Virus Vaccine Based on the Conserved Hemagglutinin Stalk Domain," mBIO, 1(0:1-9, pii: e00018-10.
Stephenson et al., 2005, "Cross-reactivity to highly pathogenic avian influenza H5N1 viruses alter vaccination with nonadjuvantcd and MF59-adjuvanted influenza A/Duck/Singapore/97 (H5N3) vaccine: a potential priming strategy." J Infect Dis., 191(8):1210-1215.
Stevens et al., 2006, "Structure and Receptor Specificity of the Hemagglutinin from an H5N1 Influenza Virus" Science, 312:404-409.
Strobel et al., 2000, "Efficient Expression of the Tumor-Associated Antigen MAGE-3 in Human Dendritic Cells, Using an Avian Influenza Virus Vector", Human Gene Therapy 11:2207-2218.
Sui et al.. 2009, "Structural and functional bases for broad-spectrum neutralization of avian and human influenza A viruses", Nat Struct Mol Biol; 16(3):265-273.
Sui et al.. 2009, "Structural and functional bases for broad-spectrum neutralization of avian and human influenza A viruses", Nat Struct Mol Biol; 16(3):265-273; Supplementary Information.
Sun et al., 2011, "Glycosylation Site Alteration in the Evolution of Influenza A (H1N1) Viruses." PLoS Pathogens, 6(7):e22844.
Talaat et al., 2014, "A Live Attenuated Influenza A(H5N1) Vaccine Induces Long-Term Immunity in the Absence of a Primary Antibody Response," Journal of Infectious Disease; 208:1860-1869.
Tamura et al., 1998, "Definition of amino acid residues on the epitope responsible for recognition by influenza A virus H1-specific, H2-specific, and H1- and H2-cross-reactive murine cytotoxic T-lymphocyte clones", J. Virol. 72:9404-9406.
Tan et al., 2012, "A pan-H1 anti-hemagglutinin monoclonal antibody with potent broad-spectrum efficacy in vivo", J. Virol. 86:6179-6188.
Tao et al., 2009, "Enhanced protective immunity against H5N1 influenza virus challenge by vaccination with DNA expressing a chimeric hemagglutinin in combination with an MHC class I-restricted epitope of nucleoprotein in mice", Antiviral research. 2009; 81(3); 253-260.
Tate, et al., 2001, "Specific Sites of N-Linked Glycosylation on the Hemagglutinin of H1N1 Subtype Influenza A Virus Determine Sensitivity to Inhibitors of the Innate Immune Systema nd Virulence in Mice." Journal of Immunology, 187(4):1884-1894.
Thoennes et al., 2008, "Analysis of residues near the fusion peptide in the influenza hemagglutinin structure for roles in triggering membrane fusion", Virology; 370(2):403-414.
Thomson et al., 2012, "Pandemic H1N1 Influenza Infection and Vaccination in Humans Induces Cross-Protective Antibodies that Target the Hemagglutinin Stem", Front. Immunol. 3:87.

Throsby et al., 2008, "Heterosubtypic neutralizing monoclonal antibodies cross-protective against H5N1 and H1N1 recovered from human IgM+ memory B cells", PLoS One; 3(12):e3942.
Tran et al., 2016, "Cryo-electron microscopy structures of chimeric hemagglutinin displayed on a universal influenza vaccine candidate", MBio, 7(2): e00257-16.
Vajdos et al., 2002, "Comprehensive Functional Maps of the Antigenbinding Site of an Anti-ErbB2 Antibody Obtained with Shotgun Scanning Mutagenesis," Journal of Molecular Biology, 320:415-428.
Vanlandschoot et al., 1995. "A fairly conserved epitope on the hemagglutinin of influenza A (H3N2) virus with variable accessibility to neutralizing antibody." Virology, 212(2)526-34.
Vanlandschoot et al., 1998. "An antibody which binds to the membrane-proximal end of influenza virus haemagglutinin (1-13 subtype) inhibits the low-pH-induced conformational change and cell-cell fusion but does not neutralize virus", Journal of General Virology; 79:1781-1791.
Vareckova et al., 2008, "HA2-specific monoclonal antibodies as tools for differential recognition of influenza A virus antigenic subtypes," Virus Research, 132:181-186.
Vigerust et al., 2007, "N-Linked Glycosylation Attenuates H3N2 Influenza Viruses", Journal of Virology, 81(16): 8593-8600.
Wang et al., 2007, "Incorporation of High Levels of Chimeric Human Immunodeficiency Virus Envelope Glycoproteins into Virus-Like Particles", J. Virol., 81(20):10869-10878.
Wang et al., 2008, "Simplified recombinational approach for influenza A virus reverse genetics", J. Virol. Methods 151:74-78.
Wang et al., 2009, "Characterization of cross-reactive antibodies against the influenza virus hemagglutinin", American Society for Virology 28th Annual Meeting, University of British Columbia, Vancouver, BC, Canada dated Jul. 11-15, 2009; Abstract W30-6.
Wang et al., 2009, "Glycans on influenza hemagglutinin affect receptor binding and immune response." PNAS, 106(43): 18137-18142.
Wang et al., 2009, "Universal epitopes of influenza virus hemagglutinins?", Nature Structural and Molecular Biology; 16(3):233-234.
Wang et al., 2010, "Broadly protective monoclonal antibodies against H3 influenza viruses following sequential immunization with different hemagglutinins", PLOS Pathogens; 6(2):1-9.
Wang et al., 2010, "Vaccination with a synthetic peptide from the influenza virus hemagglutinin provides protection against distinct viral subtypes". PNAS. 107(44): 18979-18984.
Wang et al., 2012, "Generation of recombinant pandemic H1N1 influenza virus with the HA cleavable by bromelain and identification of the residues influencing HA bromelain cleavage." Vaccine, 30(4):872-8.
Webby et al., 2010, Hemagglutinin [Influenza A virus (A/Brisbane/59/2007(H1N1))]. GenBank Acc. No. ADE28750.1. Dep. Mar. 29, 2010.
Wei et al., 2010, "Induction of Broadly Neutralizing H1N1 Influenza Antibodies by Vaccination," Science; 329: 1060-1064.
Weis and Brunger, 1990, "Refinement of the Influenza Virus Hemagglutinin by Simulated Annealing." J. Mol. Biol. 212:737-761.
Weis et al., 1988, "Structure of the influenza virus haemagglutinin complexed with its receptor, sialic acid." Nature, 333:426-431.
Weldon et al., 2010, "Enhanced immunogenicity of stabilized trimeric soluble influenza hemagglutinin", PLoSONE 5(9): e12466.
Wiley and Skehel, 1983, "The three-dimensional structure and antigenic variation of the influenza virus haemagglutinin." Division of Virology, 107-111.
Wiley, 1987, "The Structure and Function of the Hemagglutinin Membrane Glycoprotein of Influenza Virus." Ann. Rev. Biochem., 56:365-94.
Wilson et al., 1981, "Structure of the haemagglutinin membrane glycoprotein of influenza virus at 3 A resolution." Nature, 289:366-373.
Winter et al., 1981, "Nucleotide Sequence of the Haemagglutinin Gene of a Human Influenza Virus H1 Subtype" Nature, 292:72-75.

(56) References Cited

OTHER PUBLICATIONS

Wohlbold et al., 2015, "Vaccination with soluble headless hemagglutinin protects mice from challenge with divergent influenza viruses." Vaccine, 33(29):3314-3321.
Wohlbold et al., 2015, "Vaccination with adjuvanted recombinant neuraminidase induces broad heterologous, but not heterosubtypic, cross-protection against influenza virus infection in mice." MBio, 6(2):e02556.
Worobey et al., 2002, "Questioning the Evidence for Genetic Recombination in the 1918 "Spanish Flu" Virus", Science, 296(5566): 211a.
Wrammert et al., 2011, "Broadly cross-reactive antibodies dominate the human B cell response against 2009 pandemic H1N1 influenza virus infection", J. Exp. Med. 208:181-193.
Written Opinion dated Feb. 19, 2013 for PCT Application No. PCT/US2012/056122, Published as WO 2013/043729.
Written Opinion dated Apr. 28, 2014 for PCT Application No. PCT/US2013/075697, Published as WO 2014/099931.
Written Opinion dated Jun. 26, 2014 for PCT Application No. PCT/US2014/025526, Published as WO 2014/159960.
Written Opinion dated Jul. 13, 2011 for PCT Application No. PCT/US2011/030441, Published as WO 2011/123495.
Written Opinion dated Sep. 30, 2011 for PCT Application No. PCT/US2010/029202, Published as WO 2010/117786.
Written Opinion of International application No. PCT/US2010/036170, dated Aug. 17, 2010.
Written Opinion of International application No. PCT/US2011/25467, dated Oct. 19, 2011.
Yang et al., 2006, "Targeting lentiviral vectors to specific cell types in vivo", PNAS 103: 11479-11484.
Yang et al., 2007, "Immunization by Avian H5 Influenza Hemagglutinin Mutants with Altered Receptor Binding Specificity", Science, 317(5839):825-828.
Yang et al., 2014, "Structural stability of influenza A(H1N1)pdm09 virus hemagglutinins." J. Virol., 88(9):4828-38.
Yassine et al., 2015, "Hemagglutinin-stem nanoparticles generate heterosubtypic influenza protection." Nat. Med. 21(9):1065-70.
Yasugi et al., 2013, "Human monoclonal antibodies broadly neutralizing against influenza B virus", PLoS Pathog. 9(2): e1003150.
Yoshida et al., A. "Cross-protective potential of a novel monoclonal antibody directed against antigenic site B of the hemagglutinin of influenza A viruses." PLoS Pathog. 2009; 5(3);e1000350.
Zamarin et al., 2006, "Influenza A virus PB1-F2 protein contributes to viral pathogenesis in mice". J Virol. 80(16):7976-7983.
Zhang et al., 2011, "Determination of serum neutralization antibodies against seasonal influenza A strain H3N2 and the emerging strains 2009 H1N1 and avian H5N1". Scandinavian Journal of Infectious Diseases, 43:216-220.
Zheng, et al., 1996, "Nonconserved nucleotides at the 3' and 5' ends of an influenza A virus RNA play an important role in viral RNA replication", Virology 217:242-251.
Centers for Disease Control and Prevention Metropolitan Atlanta Congenital Defects Program (CDC MACDP) guidelines. Birth defects and genetic diseases branch 6-digit code for reportable congenital anomalies; http://www.cdc.gov/ncbddd/birthdefects/documents/MACDPcode0807.pdf, (2007).
EMA Guideline on the exposure to medicinal products during pregnancy: need for post-authorization data (Doc. Ref. EMEA/CHMP/313666/2005) adopted at Community level in May 2006); http://www.ema.europa.eu/docs/en_GB/document_library/Regulatory_and_procedural_guideline/2009/11/WC500011303.pdf.
Goff et al., 2013, "Induction of cross-reactive antibodies to novel H7N9 influenza virus by recombinant Newcastle disease virus expressing a North American lineage H7 subtype hemagglutinin," J. Virol., 87 (14): 8235-40.
Heaton et al., "In Vivo Bioluminescent Imaging of Influenza A Virus Infection and Characterization of Novel Cross-Protective Monoclonal Antibodies," J. Virol. 87(15):8272-8281 (2013).
Izurieta et al., 2000, "Influenza and the rates of hospitalization for respiratory disease among infants and young children," NEJM,342(4):232-239.
Krammer and Palese, 2013, "Influenza virus hemagglutinin stalk-based antibodies and vaccines," Curr. Opin. Virol., 3, 521-530.
Montplaisir et al., 2009, "Risk of narcolepsy associated with inactivated adjuvanted (AS03) A/H1N1 (2009) pandemic influenza vaccine in Quebec," PLoS One, 9 (9): e108489. doi: 10.1371/journal.pone.0108489.
Nachbagauer et al., 2014, "Induction of broadly reactive anti-hemagglutinin stalk antibodies by an H5N1 vaccine in humans," J. Virol., 88 (22): 13260-8.
Nachbagauer et al., 2016, "A chimeric haemagglutinin-based influenza split virion vaccine adjuvanted with AS03 induces protective stalk-reactive antibodies in mice." Nature Partner Journals (NPJ) Vaccines, Article No. 16015 (2016) doi:10.1038/npjvaccines.2016.15.
NCT01676402, Clinical Trial, "Seasonal Influenza HA DNA With Trivalent Inactivated Vaccine (TIV) Administered ID or IM in Healthy Adults 18-70 Years," (last updated Jul. 17, 2014).
O'Brien MA, Uyeki TM, Shay DK, Thompson WW, Kleinman K, McAdam A, Yu Xj, Platt R, Lieu TA. Incidence of Outpatient visits and hospitalizations related to influenza in infants and young children. Pediatrics. 2004; 113: 585-93.
Jerricone et al., 2013, "Autoimmune/inflammatory syndrome induced by adjuvants (ASIA) 2013: Unveiling the pathogenic, clinical and diagnostic aspects," J Autoimmun., 47:1-16.
Tete et al., 2016, "Dissecting the hemagglutinin head and stalk-specific IgG antibody response in healthcare workers following pandemic H1N1 vaccination," Nature Partner Journals (NPJ) Vaccine, Article No. 16001 doi:10.1038/npjvaccines.2016.1.
Tong et al., 2013. "New world bats harbor diverse influenza A viruses," PLoS Pathog. 9: e1003657.
Vincent et al., 2008, "Failure of protection and enhanced pneumonia with a US H1N2 swine influenza virus in pigs vaccinated with an inactivated classical swine H1N1 vaccine," Vet Microbial., 126 (4): 310-23.
WHO World Health Organization Factsheet No. 211. Influenza Nov. 2016. https://www.who.int/mediacentre/factsheets/fs211/en.
Hong et al., "Antibody recognition of the pandemic H1N1 Influenza virus hemagglutinin receptor binding site," J. Virol. 87(22):12471-12480 (2013) (Epub Sep. 11, 2013).
Zhang et al., "Crystal structure of the swine-origin A (H1N1)-2009 influenza A virus hemagglutinin (HA) reveals similar antigenicity to that of the 1918 pandemic virus," Protein Cell 1(5):459-467 (2010) (Epub Jun. 4, 2010).
Centers for Disease Control and Prevention Metropolitan Atlanta Congenital Defects Program (CDC MACDP) guidelines. Birth defects and genetic diseases branch 6-digit code for reportable congenital anomalies; http://www.cdc.gov/ncbddd/birthdefects/documents/MACDPcode0807.pdf (2007).
Cox and Fukuda, 1998, "Influenza," Infect. Dis. Clin. North Am., 12:27-38.
Crotty et al., 2004, "Tracking human antigen-specific memory B cells: a sensitive and generalized ELISPOT system," J. Immunol. Methods, 286 (1-2): 111-122.
EMA Guideline on the exposure to medicinal products during pregnancy: need for post-authorization data (Doc. Ref. EMEA/CHMP/313666/2005) adopted at Community level in May 2006); http://www.ema.europa.eu/docs/en_GB/document_library/Regulatory_and_procedural_guideline/2009/11/WC500011303.pdf.
Gauger et al., 2011, "Enhanced pneumonia and disease in pigs vaccinated with an inactivated human-like (δ-cluster) H1N2 vaccine and challenged with pandemic 2009 H1N1 influenza virus." Vaccine., 29 (15): 2712-2719.

* cited by examiner

```
                          <-------------------------------------- FR1 - IMGT
                          1           5              10             15
                          Q  I  Q  L  V  Q  S  G  P     E  L  K  K  P
GG3_Heavy_2_T3            cag atc cag ttg gtg cag tct gga cct ... gag ctg aag aag cct AJ851868 Musmus IGHV9-1*02 F   --- --- --- --- --- --- --- --- --- ... --- --- --- --- ---

--------------------------------------->
                                        20             25             30
                          G  E  T  V  K  I  S  C  K  A  S  G  Y  T  F
GG3_Heavy_2_T3            gga gag aca gtc aag atc tcc tgc aag gct tct ggg tat acc ttc AJ851868 Musmus IGHV9-1*02 F   --- --- --- --- --- --- --- --- --- --- --- --- --- --- ---

..... CDR1 - IMGT ............... <------------------------
                                         35             40             45
                                         T  N  Y  G  M  N  W  V  K  Q  A
GG3_Heavy_2_T3            ... ... ... ... aca aac tat gga atg aac tgg gtg aag cag gct AJ851868 Musmus IGHV9-1*02 F   ... ... ... ... --- --- --- --- --- --- --- --- --- --- ---

FR2 - IMGT ............................>  ........ CDR2
                                        50             55             60
                          P  G  K  G  L  K  W  M  G  W  I  N  I  Y
GG3_Heavy_2_T3            cca ggc aag ggt tta aag tgg atg ggc tgg ata aac atc tac ...
                                                                      T
AJ851868 Musmus IGHV9-1*02 F   --- --- --- --- --- --- --- --- --- --- -c- --- --- ...

- IMGT ........... <------------------------------------
                                        65             70             75
                          S  G  E  S  T  Y  V  D  D  F  T      G  R
GG3_Heavy_2_T3            ... agt gga gag tca aca tat gtt gat gac ttc acg ... gga cgg
                                T              P           A           K
AJ851868 Musmus IGHV9-1*02 F   ... -c- --- --- c-- --- --- -c- --- --- --- -a- ... --- ---

------------------------------ FR3 - IMGT -----------------
                                        80             85             90
                          F  A  F  S  L  E  T  S  A  S  T  A  Y  L  Q
GG3_Heavy_2_T3            ttt gcc ttc tct ttg gaa acc tct gcc agc act gcc tat ttg cag AJ851868 Musmus IGHV9-1*02 F   --- --- --- --- --- --- --- --- --- --- --- --- --- --- ---

------------------------------------------>
                                        95             100            104
                          I  N  N  L  K  N  E  D  M  A  T  Y  F  C  A
GG3_Heavy_2_T3            atc aac aac ctc aaa aat gag gac atg gct aca tat ttc tgt gca AJ851868 Musmus IGHV9-1*02 F   --- --- --- --- --- --- --- --- --- --- --- --- --- --- ---

....................... CDR3 - IMGT ..................

R  S  G  D  T  M  I  T  A  G  R  S  F  F
GG3_Heavy_2_T3            aga tct ggg gat act atg att acg gcg gga cgg tcc ttc ttt gct AJ851868 Musmus IGHV9-1*02 F   ---            <------ FR4 ------>

M  D  Y  W  G  Q  G  T  S  V  T  V  S  S  A
GG3_Heavy_2_T3            atg gac tac tgg ggt caa gga acc tca gtc acc gtc tcc tca gcc AJ851868 Musmus IGHV9-1*02 F
```

FIG. 1A

```
                                    K   T   T   A   P   S   V   Y   P   L   A   P   V   C   G
GG3_Heavy_2_T3                      aaa aca aca gcc cca tcg gtc tat cca ctg gcc cct gtg tgt gga AJ851868 Musmus IGHV9-1*02 F D   T   T   G   S   S   V   T   L   G   C   L   V   K   E
GG3_Heavy_2_T3                      gat aca act ggc tcc tcg gtg act cta gga tgc ctg gtc aag gaa AJ851868 Musmus IGHV9-1*02 F G   R   I   P   Q   W   I   S   S   L   S   I   P   S   T
GG3_Heavy_2_T3                      ggg cga att cca cag tgg ata tca agc tta tcg ata ccg tcg acn AJ851868 Musmus IGHV9-1*02 F S   R   G   A   X   D   P   R
GG3_Heavy_2_T3                      tcg agg ggg gcc nnn gac cca cgt ct AJ851868 Musmus IGHV9-1*02 F
```

FIG. 1B

```
                                <------------------------------------------ FR1 - IMGT
                                1           5              10             15
                                D   T   Q   M   T   Q   S   P   S   S   L   S   A   S   L
GG3_5_T3                        gac atc cag atg acc cag tct cca tcc tcc tta tct gcc tct ctg AF003294 Musmus IGKV9-124*01 F  --- --- --- --- --- --- --- --- --- --- --- --- --- --- ---

---------------------------------------->
                                                20              25             30
                                G   E   R   V   S   I   T   C   R   A   S   Q   E   I
GG3_5_T3                        gga gaa aga gtc agt ctc act tgt cgg gca agt cag gaa att ...

AF003294 Musmus IGKV9-124*01 F  --- --- --- --- --- --- --- --- --- --- --- --- --- --- ...

CDR1 - IMGT                <------------------------------
                                                    35              40             45
                                                    S   G   Y   L   S   W   L   Q   Q   K
GG3_5_T3                        ... ... ... ... ... agt ggt tac tta agc tgg ctt cag cag aaa AF003294 Musmus IGKV9-124*01 F  ... ... ... ... ... --- --- --- --- --- --- --- --- --- ---

FR2 - IMGT ------------------------>                CDR2
                                                50              55             60
                                P   D   G   T   I   K   R   L   I   Y   A   A
GG3_5_T3                        cca gat gga act att aaa cgc ctg atc tac gcc gca ... ... ...

AF003294 Musmus IGKV9-124*01 F  --- --- --- --- --- --- --- --- --- --- --- --- ... ... ...

- IMGT           <------------------------------------------
                                                65              70             75
                                                S   T   L   D   S   G   V   P       K   R
GG3_5_T3                        ... ... ... ... tcc act tta gat tct ggt gtc cca ... aaa agg AF003294 Musmus IGKV9-124*01 F  ... ... ... ... --- --- --- --- --- --- --- --- ... --- ---

------------------------------ FR3 - IMGT ---------------
                                                80              85             90
                                F   S   G   S   R           S   G   S   D   Y   S   L   S
GG3_5_T3                        ttc agt ggc agt agg ... ... tct ggg tca gat tat tct ctc tcc
                                                                                        T
AF003294 Musmus IGKV9-124*01 F  --- --- --- --- --- ... ... --- --- --- --- --- --- --- a--

---------------------------------------------------->
                                                95              100            104
                                I   S   S   L   E   S   E   D   F   A   D   Y   Y   C   L
GG3_5_T3                        atc agc agc ctt gag tct gaa gat ttt gca gac tat tac tgt ctt AF003294 Musmus IGKV9-124*01 F  --- --- --- --- --- --- --- --- --- --- --- --- --- --- --a
                                    CDR3 - IMGT
```

Fig. 2A

IMGT/V-QUEST                                           ←——— FR4 ———→

Q   Y   A   N   Y   P   W   S   F   G   G   T   K   L
GG3_5_T3     caa tat gct aat tat ccg tgg tcg ttc ggt gga ggc acc aag ctg
                             S
AF003294 Musmus IGKV9-124*01 F  --- --- --- -ga --- --t →
             E   I   K   R   A   D   A   A   P   T   V   S   I   F   P
GG3_5_T3     gaa atc aaa cgg gct gat gct gca cca act gta tcc atc ttc cca AF003294 Musmus IGKV9-124*01 F P   S   S   E   Q   L   T   S   G   G   A   S   V   V   C
GG3_5_T3     cca tcc agt gag cag tta aca tct gga ggt gcc tca gtc gtg tgc AF003294 Musmus IGKV9-124*01 F F   L   N   K   G   E   F   H   S   G   Y   Q   A   Y   R
GG3_5_T3     ttc ctg aac aag ggc gaa ttc cac agt gga tat caa gct tat cga AF003294 Musmus IGKV9-124*01 F Y   R   R   P   R   G   G   P   X   X   X
GG3_5_T3     tac cgt cga cct cga ggg ggg ccn nnn ncc nnn tt AF003294 Musmus IGKV9-124*01 F

FIG. 2B

Pre-exposure Prophylaxis - Weight Curve
GG3 - rVN04 (H5N1)

- ■ 15 mg/kg
- □ 7.5 mg/kg
- ● 3 mg/kg
- ○ 1 mg/kg
- ▲ PBS

FIG. 7A

Survival Curve
GG3 - rVN04 (H5N1)

FIG. 7B

ANTIBODIES AGAINST INFLUENZA VIRUS HEMAGGLUTININ AND USES THEREOF

This application is a national stage entry of International Patent Application No. PCT/US2014/025526, filed Mar. 13, 2014, which claims benefit of U.S. Provisional Application No. 61/783,532, filed Mar. 14, 2013, each of which is herein incorporated by reference in its entirety.

This invention was made with government support under P01 AI097092 and HHSN266200700010C awarded by the National Institutes of Health (NIH). The government has certain rights in this invention.

This application includes a Sequence Listing submitted via EFS-Web as an ASCII text file named 6923-215-999_Sequence_Listing.txt, created Aug. 2, 2017, and being 16,463 bytes in size, which is hereby incorporated by reference in its entirety.

1. INTRODUCTION

Provided herein are antibodies that cross-react with hemagglutinin from strains of influenza virus of the same subtype or different subtypes, host cells for producing such antibodies, and kits comprising such antibodies. Also provided herein are compositions comprising antibodies that cross-react with hemagglutinin from strains of influenza virus of the same subtype or different subtypes and methods of using such antibodies to diagnose, prevent or treat influenza virus disease.

2. BACKGROUND

Influenza viruses are enveloped RNA viruses that belong to the family of Orthomyxoviridae (Palese and Shaw (2007) Orthomyxoviridae: The Viruses and Their Replication, 5th ed. Fields' Virology, edited by B. N. Fields, D. M. Knipe and P. M. Howley. Wolters Kluwer Health/Lippincott Williams & Wilkins, Philadelphia, USA, p 1647-1689). The natural host of influenza viruses are avians, but influenza viruses (including those of avian origin) also can infect and cause illness in humans and other animal hosts (canines, pigs, horses, sea mammals, and mustelids). For example, the H5N1 avian influenza virus circulating in Asia has been found in pigs in China and Indonesia and has also expanded its host range to include cats, leopards, and tigers, which generally have not been considered susceptible to influenza A (CIDRAP—Avian influenza: Agricultural and Wildlife Considerations). The occurrence of influenza virus infections in animals could potentially give rise to human pandemic influenza strains.

Influenza A and B viruses are major human pathogens, causing a respiratory disease that ranges in severity from sub-clinical infection to primary viral pneumonia which can result in death. The clinical effects of infection vary with the virulence of the influenza strain and the exposure, history, age, and immune status of the host. The cumulative morbidity and mortality caused by seasonal influenza is substantial due to the relatively high rate of infection. In a normal season, influenza can cause between 3-5 million cases of severe illness and is associated with 200,000 to 500,000 deaths worldwide (World Health Organization (April, 2009) influenza (Seasonal) Fact Sheet 211). In the United States, influenza viruses infect an estimated 10-15% of the population (Glezen and Couch R B (1978) Interpandemic influenza in the Houston area, 1974-76. N Engl J Med 298: 587-592; Fox et al. (1982) influenza virus infections in Seattle families, 1975-1979. II. Pattern of infection in invaded households and relation of age and prior antibody to occurrence of infection and related illness. Am J Epidemiol 116: 228-242) and are associated with approximately 30,000 deaths each year (Thompson W W et al. (2003) Mortality Associated With influenza and Respiratory Syncytial Virus in the United States. JAMA 289: 179-186; Belshe (2007) Translational research on vaccines: influenza as an example. Clin Pharmacol Ther 82: 745-749).

In addition to annual epidemics, influenza viruses are the cause of infrequent pandemics. For example, influenza A viruses can cause pandemics such as those that occurred in 1918, 1957 and 1968. Due to the lack of pre-formed immunity against the major viral antigen, hemagglutinin (HA), pandemic influenza viruses can affect greater than 50% of the population in a single year and often cause more severe disease than seasonal influenza viruses. A stark example is the pandemic of 1918, in which an estimated 50-100 million people were killed (Johnson and Mueller (2002) Updating the Accounts: Global Mortality of the 1918-1920 "Spanish" influenza Pandemic Bulletin of the History of Medicine 76: 105-115). Since the emergence of the highly pathogenic avian H5N1 influenza virus in the late 1990s (Claas et al. (1998) Human influenza A H5N1 virus related to a highly pathogenic avian influenza virus. Lancet 351: 472-7), there have been concerns that the virus may become transmissible between humans and cause a major pandemic.

An effective way to protect against influenza virus infection is through vaccination; however, current vaccination approaches rely on achieving a good match between circulating strains and the isolates included in the vaccine formulation. Such a match is often difficult to attain due to a combination of factors. First, influenza viruses are constantly undergoing change: every 3-5 years the predominant strain of influenza A virus is replaced by a variant that has undergone sufficient antigenic drift to evade existing antibody responses. Isolates to be included in vaccine preparations must therefore be selected each year based on the intensive surveillance efforts of the World Health Organization (WHO) collaborating centers. Second, to allow sufficient time for vaccine manufacture and distribution, strains must be selected approximately six months prior to the initiation of the influenza season. Occasionally, the predictions of the vaccine strain selection committee are inaccurate, resulting in a substantial drop in the efficacy of vaccination.

The possibility of a novel subtype of influenza A virus entering the human population also presents a significant challenge to current vaccination strategies. Since it is impossible to predict what subtype and strain of influenza virus will cause the next pandemic, current, strain-specific approaches cannot be used to prepare a pandemic influenza vaccine.

3. SUMMARY

In one aspect, provided herein is an antibody (or an antigen-binding fragment thereof), which binds to an influenza virus hemagglutinin (e.g., a hemagglutinin from an influenza A virus strain of the H1 subtype and/or the H5 subtype), comprising: a variable light (VL) domain or light chain comprising a VL complementarity determining region (CDR)1, VL CDR2, and VL CDR3 having the amino acid sequences of SEQ ID NOs: 27, 29, and 31, respectively; and a variable heavy (VH) domain or heavy chain comprising a VH CDR1, VH CDR2, and VH CDR3 having the amino acid sequences of SEQ ID NOs: 19, 21 and 23, respectively. In one embodiment, provided herein is an antibody (or an antigen-binding fragment thereof), which binds to an influenza virus hemagglutinin (e.g., a hemagglutinin from an influenza A virus strain of the H1 subtype and/or the H5 subtype), comprising a light chain or VL domain comprising VL CDR1, VL CDR2, and VL CDR3 having the amino acid sequences of SEQ ID NO: 27, 29 and 31, respectively. In certain embodiments, the light chain or VL domain comprises one, two or three of framework region (FR)1, FR2, FR3, and FR4 having the amino acid sequences of SEQ ID NO: 26, 28, 30 and 32, respectively. In some embodiments, the light chain or VL domain comprises FR1, FR2, FR3, and FR4 having the amino acid sequences of SEQ ID NO: 26, 28, 30, and 32 respectively. In other embodiments, the light chain or VL domain comprises the human framework regions.

In another embodiment, provided herein is an antibody (or an antigen-binding fragment thereof), which binds to an influenza virus hemagglutinin (e.g., a hemagglutinin from an influenza A virus strain of the H1 subtype and/or the H5 subtype), wherein the heavy chain or VH domain comprises VH CDR1, VH CDR2, and VH CDR3 having the amino acid sequences of SEQ ID NO: 19, 21 and 23, respectively. In certain embodiments, the heavy chain or VH domain comprises one, two or three of FR1, FR2, FR3, and FR4 having the amino acid sequences of SEQ ID NO: 18, 20, 22 and 24, respectively. In some embodiments, the heavy chain or VH domain comprises FR1, FR2, FR3, and FR4 having the amino acid sequences of SEQ ID NO: 18, 20, 22 and 24, respectively. In other embodiments, the heavy chain or VH domain comprises the human framework regions.

In another aspect, provided herein is an antibody (or an antigen-binding fragment thereof), which binds to an influenza virus hemagglutinin (e.g., a hemagglutinin from an influenza A virus strain of the H1 subtype and/or the H5 subtype), comprising a VL domain comprising an amino acid sequence that is at least 85%, 90%, 95% or 98% identical to the amino acid sequence of SEQ ID NO: 25. In another aspect, provided herein is an antibody (or an antigen-binding fragment thereof), which binds to an influenza virus hemagglutinin (e.g., a hemagglutinin from an influenza A virus strain of the H1 subtype and/or the H5 subtype), comprising VH domain comprising an amino acid sequence that is at least 85%, 90%, 95% or 98% identical to the amino acid sequence of SEQ ID NO:17.

In another aspect, provided herein is an antibody (or an antigen-binding fragment thereof), which binds to an influenza virus hemagglutinin (e.g., a hemagglutinin from an influenza A virus strain of the H1 subtype and/or the H5 subtype), comprising a VL domain comprising the amino acid sequence of SEQ ID NO:25. In another aspect, provided herein is an antibody (or an antigen-binding fragment thereof), which binds to an influenza virus hemagglutinin (e.g., a hemagglutinin from an influenza A virus strain of the H1 subtype), comprising VH domain comprising the amino acid sequence of SEQ ID NO:17.

In another aspect, provided herein is an antibody (or an antigen-binding fragment thereof), which binds to an influenza virus hemagglutinin (e.g., a hemagglutinin from an influenza A virus strain of the H1 subtype and/or the H5 subtype), comprising: a VL domain comprising an amino acid sequence that is at least 85%, 90%, 95% or 98% identical to the amino acid sequence of SEQ ID NO:25; and VH domain comprising an amino acid sequence that is at least 85%, 90%, 95% or 98% identical to the amino acid sequence of SEQ ID NO:17. In another aspect, provided herein is an antibody (or antigen-binding fragment thereof, which binds to an influenza virus hemagglutinin (e.g., a hemagglutinin from an influenza A virus strain of the H1 subtype and/or the H5 subtype), comprising a VL domain comprising the amino acid sequence of SEQ ID NO:25; and VH domain comprising the amino acid sequence of SEQ ID NO:17.

In another aspect, provided herein is an antibody (or an antigen-binding fragment thereof), which binds to an influenza virus hemagglutinin (e.g., a hemagglutinin from an influenza A virus strain of the H1 subtype and/or the H5 subtype), comprising a light chain comprising an amino acid sequence that is at least 85%, 90%, 95% or 98% identical to the amino acid sequence of SEQ ID NO:25. In another aspect, provided herein is an antibody (or an antigen-binding fragment thereof), which binds to an influenza virus hemagglutinin (e.g., a hemagglutinin from an influenza A virus strain of the H1 subtype and/or the H5 subtype), comprising heavy chain comprising an amino acid sequence that is at least 85%, 90%, 95% or 98% identical to the amino acid sequence of SEQ ID NO:17.

In another aspect, provided herein is an antibody (or an antigen-binding fragment thereof), which binds to an influenza virus hemagglutinin (e.g., a hemagglutinin from an influenza A virus strain of the H1 subtype and/or the H5 subtype), comprising a light chain comprising the amino acid sequence of SEQ ID NO:25. In another aspect, provided herein is an antibody (or an antigen-binding fragment thereof), which binds to an influenza virus hemagglutinin (e.g., a hemagglutinin from an influenza A virus strain of the H1 subtype and/or the H5 subtype), comprising heavy chain comprising the amino acid sequence of SEQ ID NO:17.

In a particular aspect, provided herein is an antibody (or an antigen-binding fragment thereof), which binds to an influenza virus hemagglutinin (e.g., a hemagglutinin from an influenza A virus strain of the H1 subtype and/or the H5 subtype), comprising: a light chain comprising an amino acid sequence that is at least 85%, 90%, 95% or 98% identical to the amino acid sequence of SEQ ID NO:25; and heavy chain comprising an amino acid sequence that is at least 85%, 90%, 95% or 98% identical to the amino acid sequence of SEQ ID NO:17. In another aspect, provided herein is an antibody (or antigen-binding fragment thereof, which binds to an influenza virus hemagglutinin (e.g., a hemagglutinin from an influenza A virus strain of the H1 subtype and/or the H5 subtype), comprising a light chain comprising the amino acid sequence of SEQ ID NO:25; and heavy chain comprising the amino acid sequence of SEQ ID NO:17.

In another aspect, provided herein is an antibody (or antigen-binding fragment thereof), which binds to an influenza virus hemagglutinin (e.g., a hemagglutinin from an influenza A virus strain of the H1 subtype and/or the H5 subtype), wherein said antibody (or antigen-binding fragment thereof) competes (e.g., in a dose-dependent manner) for binding to the influenza virus hemagglutinin with a reference antibody comprising: a VL domain or light chain comprising a VL CDR1, VL CDR2, and VL CDR3 having the amino acid sequences of SEQ ID NOs: 27, 29, and 31, respectively; and a VH domain or heavy chain comprising a VH CDR1, VH CDR2, and VH CDR3 having the amino acid sequences of SEQ ID NOs: 19, 21 and 23, respectively. In certain embodiments, the light chain or VL domain comprises framework regions for the antibody GG3 or human framework regions and/or the heavy chain or VH domain comprises framework regions for the antibody GG3 or human framework regions. In another aspect, provided herein is an antibody (or antigen-binding fragment thereof), which binds to an influenza virus hemagglutinin (e.g., a hemagglutinin from an influenza A virus strain of the H1 subtype and/or the H5 subtype), wherein said antibody (or antigen-binding fragment thereof) competes (e.g., in a dose-dependent manner) for binding to the influenza virus hemagglutinin with a reference antibody comprising a VL domain comprising the amino acid sequence of SEQ ID NO:25; and VH domain comprising the amino acid sequence of SEQ ID NO:17.

In a specific aspect, provided herein is an antibody (or an antigen-binding fragment thereof), which binds to an influenza virus hemagglutinin (e.g., a hemagglutinin from an influenza A virus strain of the H1 subtype and/or the H5 subtype), wherein said antibody binds to the same epitope as the epitope of a reference antibody comprising: a VL domain or light chain comprising a VL CDR1, VL CDR2, and VL CDR3 having the amino acid sequences of SEQ ID NOs: 27, 29, and 31, respectively; and a VH domain or heavy chain comprising a VH CDR1, VH CDR2, and VH CDR3 having the amino acid sequences of SEQ ID NOs: 19, 21 and 23, respectively. In another specific aspect, provided herein is an antibody (or an antigen-binding fragment thereof), which binds to an influenza virus hemagglutinin (e.g., a hemagglutinin from an influenza A virus strain of the H1 subtype and/or the H5 subtype), wherein said antibody binds to the same epitope as the epitope of a reference antibody comprising a VL domain comprising the amino acid sequence of SEQ ID NO:25; and VH domain comprising the amino acid sequence of SEQ ID NO:17.

In a particular embodiment, the antibody described herein (or an antigen-binding fragment thereof) is a monoclonal antibody, e.g., a murine, chimeric, or humanized monoclonal antibody. In another embodiment, the antibody described herein is a humanized monoclonal antibody. In yet another embodiment, the antibody described herein is a Fab antibody. In yet another embodiment, the antibody described herein is a human IgG1 or IgG4 antibody. In yet another embodiment, the antibody described herein comprises a light chain constant region and a heavy chain constant region. In a further embodiment, the antibody described herein comprises a light chain constant region and a heavy chain constant region, wherein the light chain constant region is a human kappa light chain constant region. In another further embodiment, the antibody described herein comprises a light chain constant region and a heavy chain constant region, wherein the heavy chain constant region is a human gamma heavy chain constant region.

In specific embodiments, an antibody described herein or an antigen-binding fragment thereof binds to an HA from an influenza virus strain of a particular subtype (e.g., an HA from an influenza A virus strain of the H1 subtype, such as A/USSR/92/77 (H1), A/Texas/36/91 (H1), A/New Caledonia/20/99 (H1), rA/California/04/09 (H1), or A/Solomon Islands/06 (H1)) and does not bind to an HA from an influenza virus strain of another subtype (e.g., an HA from an influenza virus strain of the H3 subtype, such as A/Hong Kong/1/68 (H3)) as assessed by a technique known to one of skill in the art and/or a technique described herein (e.g., an ELISA or immunofluorescence assay such as described in Section 6, infra.).

In certain embodiments, an antibody described herein or an antigen-binding fragment thereof binds to an influenza virus HA and neutralizes the influenza virus. In specific embodiments, an antibody described herein or an antigen-binding fragment thereof binds to an HA from an influenza virus strain of a particular subtype (e.g., an HA from an influenza A virus strain of the H1 subtype, such as A/USSR/92/77 (H1), A/Texas/36/91 (H1), A/New Caledonia/20/99 (H1), rA/California/04/09 (H1), or A/Solomon Islands/06 (H1)) and neutralizes the influenza virus strain as assessed by a technique known to one of skill in the art and/or a technique described herein.

In one embodiment, an antibody described herein or an antigen-binding fragment thereof binds to an HA from an influenza virus strain of the H5 subtype (e.g., rA/Vietnam/1203/04 (H5)) and does not bind to an HA from an influenza virus strain of another subtype (e.g., an HA from an influenza virus strain of the H3 subtype, such as A/Hong Kong/1/68 (H3)) as assessed by a technique known to one of skill in the art and/or a technique described herein (e.g., an ELISA or immunofluorescence assay such as described in Section 6, infra.). In one embodiment, an antibody described herein or an antigen-binding fragment thereof binds to an HA from an influenza virus strain of the H1 subtype (e.g., A/USSR/92/77 (H1), A/Texas/36/91 (H1), A/New Caledonia/20/99 (H1), rA/California/04/09 (H1), or A/Solomon Islands/06 (H1)) and does not bind to an HA from an influenza virus strain of another subtype (e.g., an HA from an influenza virus strain of the H3 subtype, such as A/Hong Kiong/1/68 (H3)) as assessed by a technique known to one of skill in the art and/or a technique described herein (e.g., an ELISA or immunofluorescence assay such as described in Section 6, infra.). In another embodiment, an antibody described herein or an antigen-binding fragment thereof binds to an HA from an influenza virus strain of a particular subtype (e.g., an HA from an influenza A virus strain of the H5 subtype, such as rA/Vietnam/1203/04 (H5)) and an HA from an influenza virus strain of a second subtype (e.g., an HA from an influenza A virus of the H1 subtype, such as A/USSR/92/77 (H1), A/Texas/36/91 (H1), A/New Caledonia/20/99 (H1), rA/California/04/09 (H1), or A/Solomon Islands/06 (H1)), and does not bind to an HA from an influenza virus strain of another subtype (e.g., an HA from an influenza virus strain of the H3 subtype, such as A/Hong Kong/1/68 (H3)) as assessed by a technique known to one of skill in the art and/or a technique described herein (e.g., an ELISA or immunofluorescence assay such as described in Section 6, infra.).

In a particular embodiment, the antibody described herein (or an antigen-binding fragment thereof) which binds to an influenza virus hemagglutinin (e.g., a hemagglutinin from an influenza A virus strain of the H1 subtype and/or the H5 subtype) is conjugated to an agent (e.g., a therapeutic agent, a toxic agent, a detectable agent). In a specific embodiment, the conjugate described herein comprises an antibody described herein (e.g., antibody GG3, or an antigen-binding fragment thereof, or an antibody comprising CDRs of antibody GG3) and a therapeutic agent.

In another aspect, provided herein is an isolated polynucleotide encoding an antibody described herein (or antigen-binding fragment thereof). In one embodiment, provided herein is an isolated polynucleotide comprising nucleotide sequences encoding a VH domain, a VL domain, or both a VL domain and a VH domain, of an antibody described herein (e.g., antibody GG3, or an antigen-binding fragment thereof, or an antibody comprising CDRs of antibody GG3) or an antigen-binding fragment thereof. In another embodiment, the isolated polynucleotide described herein encodes a VL domain of an antibody (or an antigen-binding binding fragment thereof), which binds to an influenza virus hemagglutinin (e.g., a hemagglutinin from an influenza A virus strain of the H1 subtype and/or the H5 subtype), wherein the polynucleotide comprises the nucleotide sequence of SEQ ID NO:9. In another embodiment, the isolated polynucleotide described herein encodes a VH domain of an antibody (or antigen-binding fragment thereof), which binds to an influenza virus hemagglutinin (e.g., a hemagglutinin from an influenza A virus strain of the H1 subtype and/or the H5 subtype), wherein the polynucleotide comprises the nucleotide sequence of SEQ ID NO:1. In another embodiment, the isolated polynucleotide described herein comprises (i) the nucleotide sequence of SEQ ID NO:9 encoding a VL domain of an antibody which binds to an influenza virus hemagglutinin (e.g., a hemagglutinin from an influenza A virus strain of the H1 subtype and/or the H5 subtype), and (ii) the nucleotide sequence of SEQ ID NO:1 encoding a VH domain of the antibody.

In another embodiment, provided herein is an isolated polynucleotide comprising nucleotide sequences encoding a light chain, a heavy chain, or both a light chain and a heavy chain, of an antibody described herein (e.g., antibody GG3, or an antigen-binding fragment thereof, or an antibody comprising CDRs of antibody GG3) or an antigen-binding fragment thereof. In another embodiment, the isolated polynucleotide described herein encodes a light chain of an antibody (or an antigen-binding binding fragment thereof), which binds to an influenza virus hemagglutinin (e.g., a hemagglutinin from an influenza A virus strain of the H1 subtype and/or the H5 subtype), wherein the polynucleotide comprises the nucleotide sequence of SEQ ID NO:9. In another embodiment, the isolated polynucleotide described herein encodes a heavy chain of an antibody (or antigen-binding fragment thereof), which binds to an influenza virus hemagglutinin (e.g., a hemagglutinin from an influenza A virus strain of the H1 subtype and/or the H5 subtype), wherein the polynucleotide comprises the nucleotide sequence of SEQ ID NO:1. In another embodiment, the isolated polynucleotide described herein comprises (i) the nucleotide sequence encoding a light chain of an antibody which binds to an influenza virus hemagglutinin (e.g., a hemagglutinin from an influenza A virus strain of the H1 subtype), wherein the nucleotide comprises SEQ ID NO:9; and (ii) the nucleotide sequence encoding a heavy chain of the antibody, wherein the nucleotide sequence comprises SEQ ID NO:1.

In another embodiment, provided herein is an isolated polynucleotide comprising nucleotide sequences encoding a light chain or VL domain of an antibody (or an antigen-binding fragment thereof) which binds to an influenza virus hemagglutinin (e.g., a hemagglutinin from an influenza A virus strain of the H1 subtype), wherein the light chain or VL domain comprises VL CDR1, VL CDR2, and VL CDR3 having the amino acid sequences of SEQ ID NO: 27, 29 and 31, respectively. In certain embodiments, the light chain or VL domain comprises one, two or more of framework region (FR)1, FR2, FR3, and FR4 having the amino acid sequences of SEQ ID NO: 26, 28, 30 and 32, respectively. In some embodiments, the light chain or VL domain comprises framework region (FR)1, FR2, FR3, and FR4 having the amino acid sequences of SEQ ID NO: 26, 28, 30, and 32, respectively. In other embodiments, the light chain or VL domain comprises the human framework regions.

In another embodiment, provided herein is an isolated polynucleotide comprising nucleotide sequences encoding a heavy chain or VH domain of an antibody (or an antigen-binding fragment thereof) which binds to an influenza virus hemagglutinin (e.g., a hemagglutinin from an influenza A virus strain of the H1 subtype), wherein the heavy chain or VH domain comprises VH CDR1, VH CDR2, and VH CDR3 having the amino acid sequences of SEQ ID NO: 19, 21 and 23, respectively. In certain embodiments, the heavy chain or VH domain comprises one, two or more of framework region (FR)1, FR2, FR3, and FR4 having the amino acid sequences of SEQ ID NO: 18, 20, 22 and 24, respectively. In some embodiments, the heavy chain or VH domain comprises framework region (FR)1, FR2, FR3, and FR4 having the amino acid sequences of SEQ ID NO: 18, 20, 22 and 24, respectively. In other embodiments, the heavy chain or VH domain comprises the human framework regions.

In a particular aspect, provided herein is a vector, e.g., a mammalian expression vector, comprising one or more polynucleotides (or isolated polynucleotides) comprising nucleotide sequences encoding an antibody described herein (e.g. antibody GG3, or an antigen-binding fragment thereof, or an antibody comprising CDRs of antibody GG3). In a further embodiment, the vector described herein is a mammalian expression vector.

In a particular embodiment, provided herein is a host cell (e.g., mammalian host cell) comprising the isolated polynucleotide described herein. In another embodiment, provided herein is a hybridoma cell producing an antibody described herein (e.g. antibody GG3, or an antigen-binding fragment thereof, or an antibody comprising CDRs of antibody GG3).

In another aspect, provided herein is a method for producing an antibody (or an antigen-binding fragment thereof) which binds to an influenza virus hemagglutinin, comprising culturing a cell described herein (e.g., host cell). In a further embodiment, the method described herein for producing an antibody (or an antigen-binding fragment thereof) further comprises the step of purifying the antibody expressed by the cell. In another further embodiment, the method described herein is for large scale production.

In a particular aspect, provided herein is a composition comprising an antibody (e.g., isolated antibody or monoclonal antibody) described herein (e.g., antibody GG3, or an antigen-binding fragment thereof, or an antibody comprising CDRs of antibody GG3). In another aspect, provided herein is a composition comprising a conjugate described herein.

In a particular aspect, provided herein is a pharmaceutical composition comprising an isolated antibody described herein (e.g. antibody GG3 or an antibody comprising CDRs of antibody GG3) or an antigen-binding fragment thereof and a pharmaceutically acceptable carrier.

In another aspect, provided herein is a kit comprising an antibody described herein (e.g. antibody GG3, or an antigen-binding fragment thereof, or an antibody comprising CDRs of antibody GG3) or an antigen-binding fragment thereof.

In another aspect, provided herein are methods of preventing and/or treating an influenza virus disease comprising administering to a subject an antibody described herein or an antigen-binding fragment thereof, or a pharmaceutical composition thereof. In a specific embodiment, provided herein are methods for preventing and/or treating influenza virus infection comprising administering to a subject an antibody described herein or an antigen-binding fragment thereof, or a pharmaceutical composition thereof.

In another aspect, provided herein are methods of preventing and/or treating an influenza virus disease comprising administering to a subject a conjugate described herein or a pharmaceutical composition thereof. In a specific embodiment, provided herein are methods for preventing and/or treating influenza virus infection comprising administering to a subject a conjugate described herein or a pharmaceutical composition thereof.

In another aspect, provided herein are methods for detecting an influenza virus, or detecting, diagnosing or monitoring an influenza virus infection in a subject using an antibody described herein or an antigen-binding fragment thereof. In a specific embodiment, a method of detecting a strain of influenza A virus comprises: (a) assaying for the level of an influenza virus hemagglutinin (HA) in cells or a tissue sample of a subject using an antibody or antigen-binding fragment thereof; and (b) comparing the level of the influenza virus HA assayed in (a) with the level of the influenza virus HA in cells or tissue samples not infected with influenza virus (e.g., a control level), wherein an increase in the assayed level of influenza virus HA compared to the control level of the influenza virus antigen is indicative of the presence of a strain of influenza A virus. In specific embodiments, the strain of influenza A virus detected belongs to the H1 subtype. In some embodiments, the strain of influenza A virus detected belongs to the H5 subtype.

3.1 Terminology

As used herein, the term "about" or "approximately" when used in conjunction with a number refers to any number within 0.25%, 0.5%, 1%, 5% or 10% of the referenced number.

"Affinity" of an antibody described herein for an epitope (e.g., an influenza virus HA epitope) is a term well understood in the art and refers to the extent, or strength, of binding of an antibody to an epitope. Affinity can be measured and/or expressed in a number of ways known in the art, including, but not limited to, equilibrium dissociation constant ($K_D$ or $K_d$), apparent equilibrium dissociation constant ($K_D'$ or $K_d'$), and $IC_{50}$ (amount needed to affect 50% inhibition in a competition assay). It is understood that, for purposes described herein, an affinity is an average affinity for a given population of antibodies which bind to an epitope. Values of $K_D$ or $K_D'$ described herein are generally in terms of molar concentration (mol/liter or M), e.g., molar concentration of serum (or plasma). When antibody affinity is used as a basis for administration of the treatment methods described herein, or selection for the treatment methods described herein, antibody affinity can be measured before and/or during treatment, and the values obtained can be used by a clinician in assessing whether a human patient is an appropriate candidate for treatment.

Antibodies encompassed herein include, but are not limited to, synthetic antibodies, monoclonal antibodies, recombinantly produced antibodies, monospecific antibodies, multispecific antibodies (including bispecific antibodies), human antibodies, humanized antibodies, chimeric antibodies, synthetic antibodies, tetrameric antibodies, comprising two heavy chain and two light chain molecules, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single-chain Fvs (scFv) (e.g., including monospecific, bispecific, etc.), camelized antibodies, affybodies, Fab fragments, F(ab') fragments, disulfide-linked Fvs (sdFv), anti-idiotypic (anti-Id) antibodies (including, e.g., anti-anti-Id antibodies), and epitope-binding or antigen-binding fragments of any of the above. In particular, antibodies encompassed herein include immunoglobulin molecules and immunologically active portions of immunoglobulin molecules, i.e., antigen binding domains or molecules that contain an antigen-binding site that binds to an influenza virus HA (e.g., one, two or more complementarity determining regions (CDRs) of an anti-influenza virus HA antibody). The antibodies encompassed herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule.

As used herein, a "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve one, two, three, four, or more of the following effects: (i) reduction or amelioration the severity of an influenza virus infection, an influenza virus disease or a symptom associated therewith; (ii) reduction in the duration of an influenza virus infection, an influenza virus disease or a symptom associated therewith; (iii) prevention of the progression of an influenza virus infection, an influenza virus disease or a symptom associated therewith; (iv) regression of an influenza virus infection, an influenza virus disease or a symptom associated therewith; (v) prevention of the development or onset of an influenza virus infection, an influenza virus disease or a symptom associated therewith; (vi) prevention of the recurrence of an influenza virus infection, an influenza virus disease or a symptom associated therewith; (vii) reduction or prevention of the spread of an influenza virus from one cell to another cell, one tissue to another tissue, or one organ to another organ; (viii) prevention or reduction of the spread/transmission of an influenza virus from one subject to another subject; (ix) reduction in organ failure associated with an influenza virus infection or influenza virus disease; (x) reduction in the hospitalization of a subject; (xi) reduction in the hospitalization length; (xii) an increase in the survival of a subject with an influenza virus infection or a disease associated therewith; (xiii) elimination of an influenza virus infection or a disease associated therewith; (xiv) inhibition or reduction in influenza virus replication; (xv) inhibition or reduction in the binding or fusion of influenza virus to a host cell(s); (xvi) inhibition or reduction in the entry of an influenza virus into a host cell(s); (xvii) inhibition or reduction of replication of the influenza virus genome; (xviii) inhibition or reduction in the synthesis of influenza virus proteins; (xix) inhibition or reduction in the assembly of influenza virus particles; (xx) inhibition or reduction in the release of influenza virus particles from a host cell(s); (xxi) reduction in influenza virus titer; (xxii) the reduction in the number of symptoms associated with an influenza virus infection or an influenza virus disease; (xxiii) enhancement, improvement, supplementation, complementation, or augmentation of the prophylactic or therapeutic effect(s) of another therapy; (xxiv) prevention of the onset or progression of a secondary infection associated with an influenza virus infection; and/or (xxv) prevention of the onset or diminution of disease severity of bacterial pneumonias occurring secondary to influenza virus infections. In some embodiments, the "effective amount" of a therapy has a beneficial effect but does not cure an influenza virus infection or a disease associated therewith. In certain embodiments, the "effective amount" of a therapy may encompass the administration of multiple doses of a therapy at a certain frequency to achieve an amount of the therapy that has a prophylactic and/or therapeutic effect. In other situations, the "effective amount" of a therapy may encompass the administration of a single dose of a therapy at a certain amount. Exemplary doses of an effective amount are provided in Section 5.5.2, infra.

In certain embodiments, the effective amount does not result in complete protection from an influenza virus disease, but results in a lower titer or reduced number of influenza viruses compared to an untreated subject. In certain embodiments, the effective amount results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, the effective amount results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 5 logs, 2 to 10 logs, 2 to 5 logs, or 2 to 10 logs. Benefits of a reduction in the titer, number or total burden of influenza virus include, but are not limited to, less severe symptoms of the infection, fewer symptoms of the infection, reduction in the length of the disease associated with the infection, and prevention of the onset or diminution of disease severity of bacterial pneumonias occurring secondary to influenza virus infections.

As used herein, the term "elderly human" refers to a human 65 years or older.

As used herein, an "epitope" is a term in the art and refers to a localized region of an antigen to which an antibody, or an antigen-binding fragment thereof, can bind. A region or a polypeptide contributing to an epitope can be contiguous amino acids of the polypeptide or an epitope can come together from two or more non-contiguous regions of the polypeptide. In a specific embodiment, an epitope is a conformational epitope.

As used herein, the term "fragment" refers to a sequence comprising at least 2 consecutive amino acids or nucleotides from a parent sequence. In a specific embodiment, it refers to 2 to 10, 2 to 15, 2 to 30, 5 to 30, 10 to 60, 25 to 50, 25 to 100, 100 to 175, 150 to 250, 150 to 300 or more consecutive amino acids or nucleotides from a parent sequence.

The term "heavy chain" when used in reference to an antibody generally refers to any distinct types, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4. In a specific embodiment, the heavy chain is a human heavy chain. In specific embodiments, the heavy chain is a murine heavy chain. In specific embodiments, the heavy chain is a rodent heavy chain, e.g., *rattus* light chain.

As used herein, the terms "hemagglutinin" and "HA" refer to any influenza virus hemagglutinin known to those of skill in the art. In certain embodiments, the influenza virus hemagglutinin is an influenza A virus hemagglutinin, an influenza B virus hemagglutinin or an influenza C virus hemagglutinin. A typical hemagglutinin comprises domains known to those of skill in the art including a signal peptide, a stem domain, a globular head domain, a luminal domain, a transmembrane domain and a cytoplasmic domain. In certain embodiments, a hemagglutinin consists of a single polypeptide chain, such as HA0. In certain embodiments, a hemagglutinin consists of more than one polypeptide chain in quaternary association, e.g. HA1 and HA2. In certain embodiments, a hemagglutinin consists of a hemagglutinin monomer (HA0 or HA1/HA2). In certain embodiments, a hemagglutinin consists of a trimeric hemagglutinin molecule as it is expressed on the viral surface. Those of skill in the art will recognize that an immature HA0 might be cleaved to release a signal peptide (approximately 20 amino acids) yielding a mature hemagglutinin HA0. A hemagglutinin HA0 might be cleaved at another site to yield HA1 polypeptide (approximately 320 amino acids, including the globular head domain and a portion of the stem domain) and HA2 polypeptide (approximately 220 amino acids, including the remainder of the stem domain, a luminal domain, a transmembrane domain and a cytoplasmic domain). In certain embodiments, a hemagglutinin comprises a signal peptide, a transmembrane domain and a cytoplasmic domain. In certain embodiments, a hemagglutinin lacks a signal peptide, i.e. the hemagglutinin is a mature hemagglutinin. In certain embodiments, a hemagglutinin lacks a transmembrane domain or cytoplasmic domain, or both. As used herein, the terms "hemagglutinin" and "HA" encompass hemagglutinin polypeptides that are modified by post-translational processing such as signal peptide cleavage, disulfide bond formation, glycosylation (e.g., N-linked glycosylation), protease cleavage and lipid modification (e.g. S-palmitoylation).

As used herein, the term "host cell" refers to any type of cell, e.g., a primary cell or a cell from a cell line. In specific embodiments, the term "host cell" refers a cell transfected with a polynucleotide and the progeny or potential progeny of such a cell. Progeny of such a cell may not be identical to the parent cell transfected with the polynucleotide due to mutations or environmental influences that may occur in succeeding generations or integration of the polynucleotide into the host cell genome.

As used herein, the term "human adult" refers to a human that is 18 years or older.

As used herein, the term "human child" refers to a human that is 1 year to 18 years old.

As used herein, the term "human infant" refers to a newborn to 1 year old human.

As used herein, the term "human toddler" refers to a human that is 1 years to 3 years old.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating.

As used herein, the terms "influenza virus disease" and a disease associated with an influenza virus infection refer to the pathological state resulting from the presence of an influenza virus (e.g., influenza A or B virus) in a cell or subject or the invasion of a cell or subject by an influenza virus. In specific embodiments, the term refers to a respiratory illness caused by an influenza virus.

An "isolated" nucleic acid, polynucleotide or nucleotide sequence, such as a cDNA molecule, is substantially free of other cellular material, or culture medium when produced by recombinant techniques, or substantially free of chemical precursors or other chemicals when chemically synthesized. The term "substantially free of cellular material" includes preparations of the nucleic acid, polynucleotide or nucleotide sequence in which the nucleic acid, polynucleotide or nucleotide sequence is separated from cellular components of the cells from which it is isolated or recombinantly produced. Thus, nucleic acid, polynucleotide or nucleotide sequence that is substantially free of cellular material includes preparations of the nucleic acid, polynucleotide or nucleotide sequence having less than about 30%, 20%, 10%, or 5% (by dry weight) of other nucleic acid, polynucleotide or nucleotide sequences. The term "substantially free of culture medium" includes preparations of the nucleic acid, polynucleotide or nucleotide sequence in which the culture medium represents less than about 50%, 20%, 10%, or 5% of the volume of the preparation. The term "substantially free of chemical precursors or other chemicals" includes preparations in which the nucleic acid, polynucleotide or nucleotide sequence is separated from chemical precursors or other chemicals which are involved in the synthesis of the nucleic acid, polynucleotide or nucleotide sequence. In specific embodiments, such preparations of the nucleic acid, polynucleotide or nucleotide sequence have less than about 50%, 30%, 20%, 10%, 5% (by dry weight) of chemical precursors or compounds other than the nucleic acid of interest.

The terms "Kabat numbering," and like terms are recognized in the art and refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad. Sci.* 190:382-391 and, Kabat et al. (1991) *Sequences of Proteins of Immunological Interest*, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3. For the light chain variable region, the hypervariable region typically ranges from amino acid positions 24 to 34 for CDR1, amino acid positions 50 to 56 for CDR2, and amino acid positions 89 to 97 for CDR3.

The term "light chain" when used in reference to an antibody generally refers to any distinct types, e.g., kappa (κ) of lambda (λ), based on the amino acid sequence of the constant domains. Light chain amino acid sequences are well known in the art. In specific embodiments, the light chain is a human light chain. In specific embodiments, the light chain is a murine light chain. In specific embodiments, the light chain is a rodent light chain, e.g., *Rattus* light chain.

As used herein, the numeric term "log" refers to $\log_{10}$.

As used herein, the terms "manage," "managing," and "management" refer to the beneficial effects that a subject derives from a therapy (e.g., a prophylactic or therapeutic agent), which does not result in a cure of the infection or disease associated therewith. In certain embodiments, a subject is administered one or more therapies (e.g., prophylactic or therapeutic agents, such as an antibody encompassed herein) to "manage" an influenza virus disease, or one or more symptoms thereof, so as to prevent the progression or worsening of the disease.

As used herein, the term "monoclonal antibody" is a term of the art and generally refers to an antibody obtained from a population of homogenous or substantially homogeneous antibodies, and each monoclonal antibody will typically recognize a single epitope (e.g., single conformation epitope) on the antigen. In specific embodiments, a "monoclonal antibody," as used herein, is an antibody produced by a single hybridoma or other cell (e.g., host cell producing a recombinant antibody), wherein the antibody binds to an influenza virus HA epitope as determined, e.g., by ELISA or other antigen-binding or competitive binding assay known in the art. Generally, a population of monoclonal antibodies can be generated by cells, a population of cells, or a cell line. The term "monoclonal" is not limited to any particular method for making the antibody. For example, monoclonal antibodies described herein can be made by the hybridoma method as described in Kohler et al.; Nature, 256:495 (1975) or can be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel et al., eds., John Wiley and Sons, New York). In specific embodiments, a monoclonal antibody is an antibody produced by a single hybridoma or other cell, wherein the antibody binds to an influenza virus HA epitope as determined, e.g., by ELISA or other antigen-binding or competitive binding assay known in the art.

As used herein, the terms "polynucleotides" "nucleic acid" and "nucleotide" include deoxyribonucleotides, deoxyribonucleic acids, ribonucleotides, and ribonucleic acids, and polymeric forms thereof, and includes either single- or double-stranded forms. In certain embodiments, the terms "polynucleotides" "nucleic acid" and "nucleotide" include known analogues of natural nucleotides, for example, peptide nucleic acids ("PNA" s), that have similar binding properties as the reference nucleic acid. In some embodiments, the terms "polynucleotides" "nucleic acid" and "nucleotide" refer to deoxyribonucleic acids (e.g., cDNA or DNA). In other embodiments, the terms "polynucleotides" "nucleic acid" and "nucleotide" refer to ribonucleic acids (e.g., mRNA or RNA).

As used herein, the terms "prevent," "preventing" and "prevention" in the context of the administration of a therapy(ies) to a subject to prevent an influenza virus disease or influenza virus infection refers to the prophylactic effect resulting from the administration of the therapy(ies). In a specific embodiment, the terms "prevent," "preventing" and "prevention" in the context of the administration of a therapy(ies) to a subject to prevent an influenza virus disease refer to one or more of the following effects resulting from the administration of a therapy or a combination of therapies: (i) the inhibition or reduction in the development or onset of an influenza virus disease or a symptom thereof (e.g., fever, myalgia, edema, inflammatory infiltrates); (ii) the inhibition or reduction in the recurrence of an influenza virus disease or a symptom associated therewith; and (iii) the reduction or inhibition in influenza virus infection and/or replication. In another specific embodiment, the terms "prevent", "preventing" and "prevention" in the context of the administration of a therapy(ies) to a subject to prevent an influenza virus infection refer to one or more of the following: (i) the reduction or inhibition of the spread of influenza virus from one cell to another cell; (ii) the reduction or inhibition of the spread of influenza virus from one organ or tissue to another organ or tissue; (iii) the reduction or inhibition of the spread of influenza virus from one region of an organ or tissue to another region of the organ or tissue (e.g., the reduction in the spread of influenza virus from the upper to lower respiratory tract); (iv) the prevention of an initial infection after exposure to an influenza virus; and/or (v) prevention of the onset or development of one or more symptoms associated with influenza virus disease or infection.

As used herein, the terms "subject" and "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In another embodiment, a subject is a human. In another embodiment, a subject is a human infant. In another embodiment, a subject is a human child. In another embodiment, the subject is a human adult. In another embodiment, a subject is an elderly human.

As used herein, the terms "therapies" and "therapy" can refer to any protocol(s), method(s), compound(s), composition(s), formulation(s), and/or agent(s) that can be used in the prevention or treatment of a viral infection or a disease or symptom associated therewith. In certain embodiments, the terms "therapies" and "therapy" refer to biological therapy, supportive therapy, and/or other therapies useful in treatment or prevention of a viral infection or a disease or symptom associated therewith known to one of skill in the art. In some embodiments, the term "therapy" refers to an antibody that binds an influenza virus HA. In other embodiments, the term "therapy" refers to an immunogenic composition (e.g., an influenza virus vaccine).

As used herein, the terms "treat," "treatment," and "treating" in the context of administration of a therapy(ies) to a subject to treat an influenza virus disease or influenza virus infection refer to a beneficial or therapeutic effect of a therapy or a combination of therapies. In specific embodiments, such terms refer to one, two, three, four, five or more of the following effects resulting from the administration of a therapy or a combination of therapies: (i) reduction or amelioration in the severity of an influenza virus infection, an influenza virus disease or a symptom associated therewith; (ii) reduction in the duration of an influenza virus infection, an influenza virus disease or a symptom associated therewith; (iii) prevention of the progression of an influenza virus infection, an influenza virus disease or a symptom associated therewith; (iv) regression of an influenza virus infection, an influenza virus disease or a symptom associated therewith; (v) prevention of the development or onset of an influenza virus infection, an influenza virus disease or a symptom associated therewith; (vi) prevention of the recurrence of an influenza virus infection, an influenza virus disease or a symptom associated therewith; (vii) reduction or prevention of the spread of an influenza virus from one cell to another cell, one tissue to another tissue, or one organ to another organ; (viii) prevention or reduction of the spread/transmission of an influenza virus from one subject to another subject; (ix) reduction in organ failure associated with an influenza virus infection or influenza virus disease; (x) reduction in the hospitalization of a subject; (xi) reduction in the hospitalization length; (xii) an increase in the survival of a subject with an influenza virus infection or a disease associated therewith; (xiii) elimination of an influenza virus infection or a disease associated therewith; (xiv) inhibition or reduction in influenza virus replication; (xv) inhibition or reduction in the binding or fusion of influenza virus to a host cell(s); (xvi) inhibition or reduction in the entry of an influenza virus into a host cell(s); (xvii) inhibition or reduction of replication of the influenza virus genome; (xviii) inhibition or reduction in the synthesis of influenza virus proteins; (xix) inhibition or reduction in the assembly of influenza virus particles; (xx) inhibition or reduction in the release of influenza virus particles from a host cell(s); (xxi) reduction in influenza virus titer; (xxii) the reduction in the number of symptoms associated with an influenza virus infection or an influenza virus disease; (xxiii) enhancement, improvement, supplementation, complementation, or augmentation of the prophylactic or therapeutic effect(s) of another therapy; (xxiv) prevention of the onset or progression of a secondary infection associated with an influenza virus infection; and/or (xxv) prevention of the onset or diminution of disease severity of bacterial pneumonias occurring secondary to influenza virus infections.

4 DESCRIPTION OF THE FIGURES

FIGS. 1A-1B. The nucleotide and amino acid sequences of the variable heavy chain region of the monoclonal antibody GG3 are depicted in FIGS. 1A-1B. The CDRs and framework regions of antibody GG3 are indicated. The variable heavy chain region of antibody GG3 is compared to GenBank Accession No. AJ851868, Mus musculus immunoglobin heavy chain locus constant region and partial variable region. The heavy chain of antibody GG3 is a member of the IgG HV9-1*02 family. From top to bottom, the sequences depicted are the amino acid sequence of SEQ ID NO: 33 and the nucleotide sequence of SEQ ID NO: 34.

FIGS. 2A-2B. The nucleotide and amino acid sequences of the variable light chain region of the monoclonal antibody GG3 are depicted in FIGS. 2A-2B. The CDRs and framework regions of antibody GG3 are indicated. The variable light chain region of antibody GG3 is compared to GenBank Accession No. AF003294.1, mus musculus Ig Kappa light chain variable region gene. The light chain of antibody GG3 is a member of the IgG KV9-124*01 family. From top to bottom, the sequences depicted are the amino acid sequence of SEQ ID NO: 35 and the nucleotide sequence of SEQ ID NO: 36.

FIG. 3. The reactivity of the monoclonal antibody GG3 against Madin-Darby kidney (MDCK) cells uninfected or infected with either A/USSR/92/77 (H1) (USSR77 (H1)), A/Texas/36/91 (H1) (TX91 (H1)), A/New Caledonia/20/99 (H1) (N. Cal99 (H1)), A/Brisbane/59/07 (H1) (Brisbane07 (H1)), rA/California/04/09 (H1) (Cal09 (H1)), or A/Hong Kong/1/68 (H3) (HK68 (H3)) or rA/Vietnam/1203/04 (H5) (VN04 (H5)). The reactivity of the monoclonal antibody E10, which is specific for the influenza virus M2 protein, was used as a control.

Figure 4:
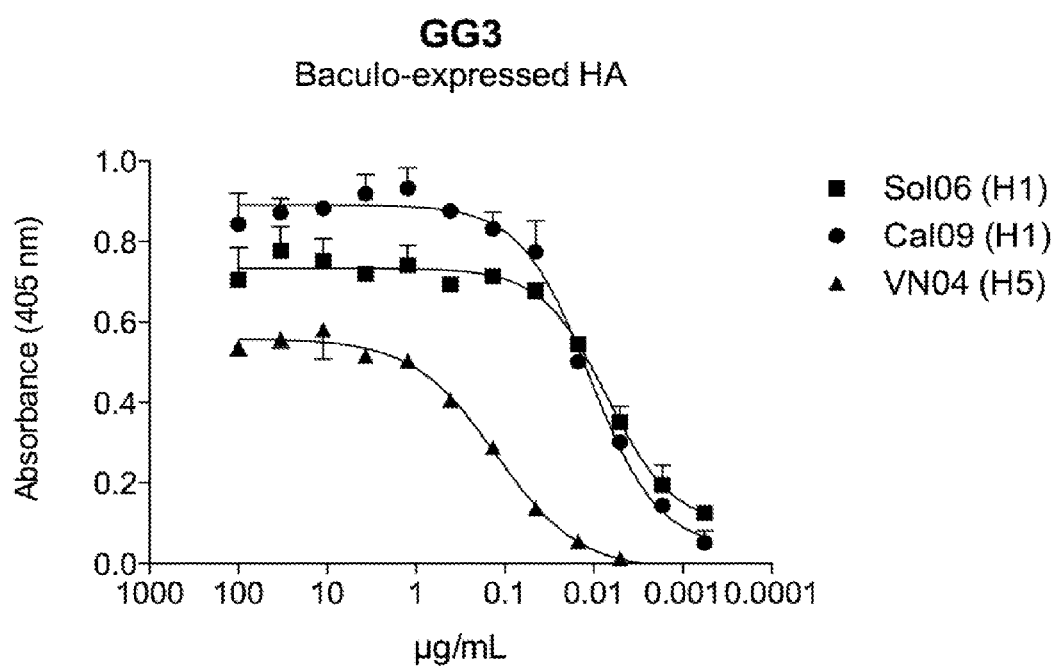

FIG. 4. The reactivity of the monoclonal antibody GG3 with baculovirus-expressed hemagglutinin from influenza virus A/Solomon Islands/06 (H1) (Sol06 (H1)), A/California/04/09 (H1) (Cal09 (H1)), or A/Vietnam/1203/04 (H5) (VN04 (H5)) as measured by ELISA.

Figure 5:
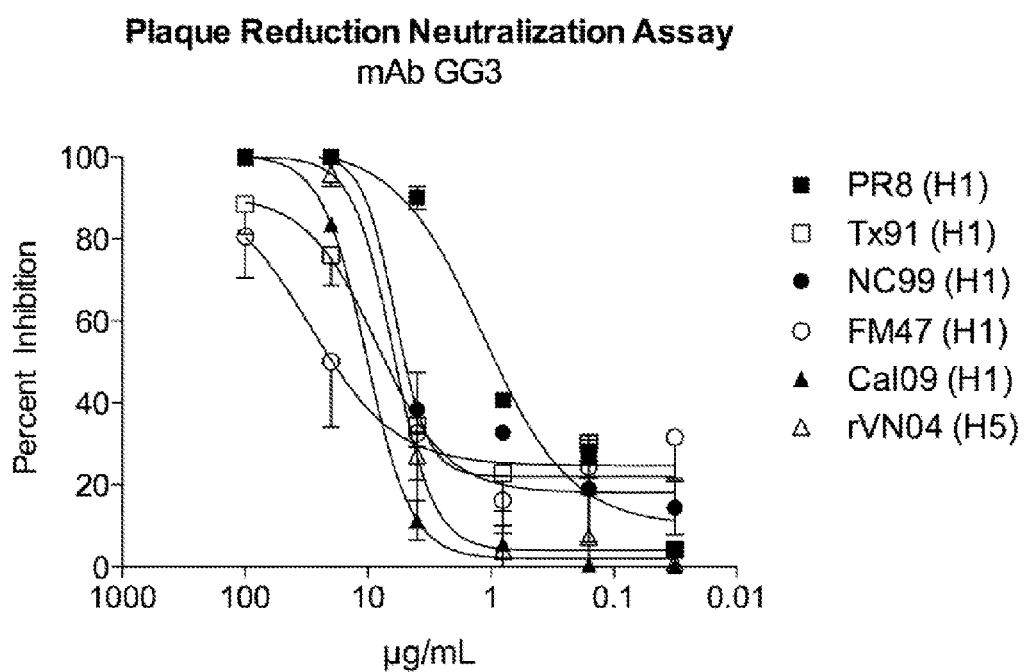

FIG. 5. Neutralization of influenza A virus strains (either A/Puerto Rico/8/34 (PR8), A/Texas/36/91 (H1) (Tx 91 (H1)), A/New Caledonia/20/99 (H1) (NC99 (H1)), A/Fort Monmouth/1/47 ((FM47) (H1)), rA/California/04/09 (H1) (Cal09 (H1)), or rANietnam/1203/04 (H5) (rVN04 (H5))) by monoclonal antibody GG3 as measured by plaque reduction assay.

Figure 6A:
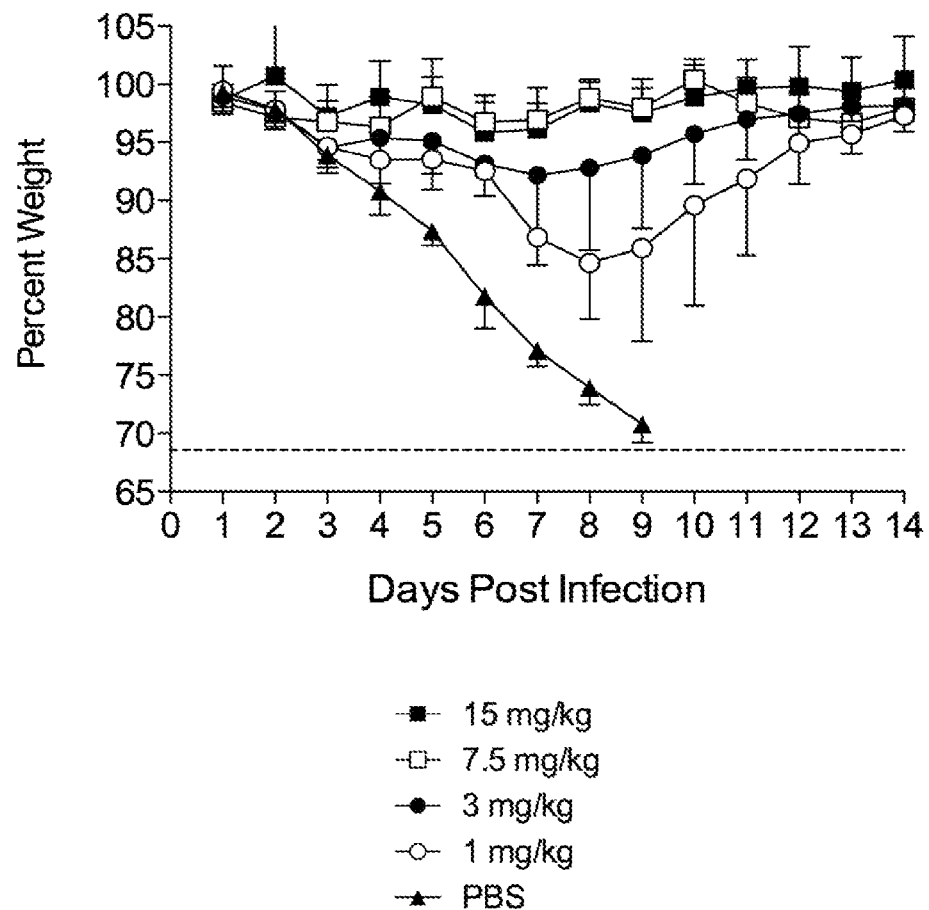
Figure 6B:
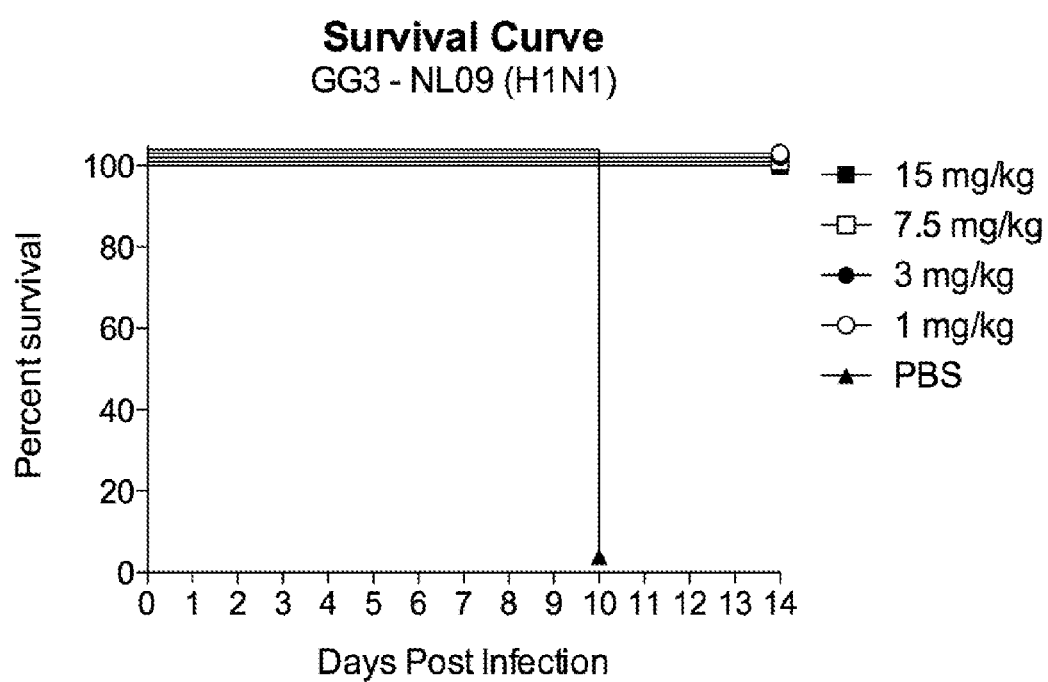

FIGS. 6A-6B. A) Passive transfer of the monoclonal antibody GG3 results in decreased weight loss in mice challenged with influenza A virus strain A/Netherlands/602/2009 (NL09) (H1) as compared to mice administered PBS alone. B) Mice injected with the monoclonal antibody GG3 two hours prior to challenge with influenza virus strain A/Netherlands/602/2009 (NL09) (H1) survive fourteen days after viral challenge, whereas mice injected with PBS alone die ten days after viral challenge.

Figure 7B:
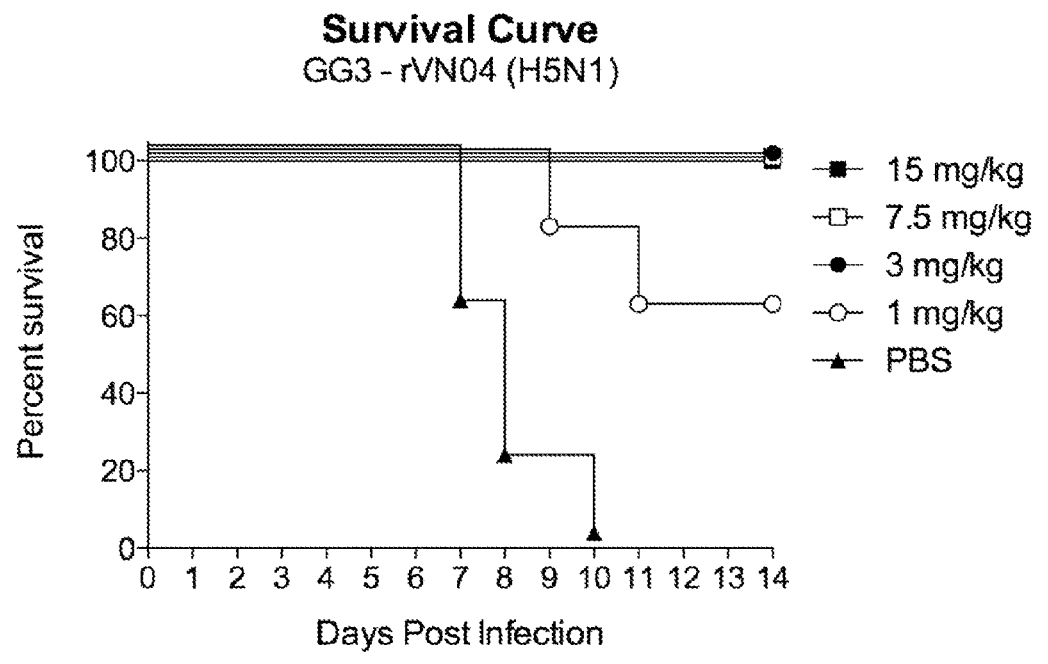

FIGS. 7A-7B. A) Passive transfer of the monoclonal antibody GG3 results in decreased weight loss in mice challenged with influenza A virus strain rA/Vietnam/1203/04 (rVN04) (H3) as compared to mice administered PBS alone. B) Mice injected with the monoclonal antibody GG3 two hours prior to challenge with influenza virus strain rA/Vietnam/1203/04 (rVN04) (H3) survive fourteen days after viral challenge, whereas mice injected with PBS alone die ten days after viral challenge.

5. DETAILED DESCRIPTION

5.1 Antibodies

Provided herein are antibodies that bind to an influenza virus hemagglutinin. In a specific embodiment, provided herein is an antibody that binds to the HA of a certain group, cluster or subtype of influenza virus, e.g., a Group 1 influenza virus, the H1 subtype of the influenza A virus, or the H5 subtype of the influenza A virus. In certain embodiments, an antibody described herein has a higher affinity for a certain group, cluster or subtype of influenza virus (e.g., a Group 1 influenza virus or the H1 subtype of the influenza A virus) than to another group or subtype of influenza virus. In specific embodiments, the affinity of an antibody described herein for a certain group, cluster or subtype of influenza virus (e.g., a Group 1 influenza virus, the H1 subtype of the influenza A virus, or the H5 subtype of the influenza A virus) is 1-fold, 1.5-fold, 2-fold, 3-fold, 4-fold, 5-fold, 6-fold, 7-fold, 8-fold, 9-fold, 10-fold, greater than 10-fold, 1- to 2-fold, 1- to 5-fold, 1- to 10-fold, 2- to 5-fold, 2- to 10-fold, 5- to 10-fold, 10- to 15-fold, or 10- to 20-fold greater than the affinity of the antibody to another group, cluster or subtype of influenza virus. In specific embodiments, the affinity of an antibody described herein for a certain group, cluster or subtype of influenza virus (e.g., a Group 1 influenza virus, the H1 subtype of the influenza A virus, or the H5 subtype of the influenza A virus) is 0.5 log, 1 log, 1.5 log, 2 log, 2.5 log, 3 log, 3.5 log, or 4 log greater than the affinity of the antibody to another group, cluster or subtype of influenza virus.

In a specific embodiment, provided herein is an antibody that selectively binds to hemagglutinin from one, two, three or more strains of influenza virus of a particular subtype (e.g., H1 and/or H5) relative to hemagglutinin of an influenza virus strain of a different subtype (e.g., H3) as assessed by techniques known in the art, e.g., ELISA, Western blot, FACs or BIACore. In other words, the antibody binds to hemagglutinin from one, two, three or more strains of influenza virus of a particular subtype (e.g., H1) with a higher affinity than the antibody binds to hemagglutinin of an influenza virus strain of a different subtype (e.g., H3) as assessed by techniques known in the art, e.g., ELISA, Western blot, FACs or BIACore. In specific embodiments, an antibody described herein binds to hemagglutinin from one, two, three or more strains of influenza virus of a particular subtype (e.g., H1 and/or H5) with a 1-fold, 1.5-fold, 2-fold, 3-fold, 4-fold, 5-fold, 6-fold, 7-fold, 8-fold, 9-fold, 10-fold, greater than 10-fold, 1-to 2-fold, 1- to 5-fold, 1- to 10-fold, 2- to 5-fold, 2- to 10-fold, 5- to 10-fold, 10- to 15-fold, or 10- to 20-fold greater affinity than that which they bind to a hemagglutinin of an influenza virus strain of a different subtype (e.g., H3). In specific embodiments, an antibody described herein binds to hemagglutinin from one, two, three or more strains of influenza virus of a particular subtype (e.g., H1 and/or H5) with a 0.5 log, 1 log, 1.5 log, 2 log, 2.5 log, 3 log, 3.5 log, or 4 log greater affinity than that which they bind to hemagglutinin of an influenza virus strain of a different subtype (e.g., H3).

In another embodiment, provided herein is an antibody that selectively binds to hemagglutinin from one, two, three or more strains of influenza virus relative to a non-influenza virus hemagglutinin antigen as assessed by techniques known in the art, e.g., ELISA, Western blot, FACs or BIACore. In other words, the antibody binds to hemagglutinin from one, two, three or more strains of influenza virus with a higher affinity than the antibody binds to a non-influenza virus hemagglutinin antigen as assessed by techniques known in the art, e.g., ELISA, Western blot, FACs or BIACore. In specific embodiments, an antibody described herein binds to hemagglutinin from one, two, three or more strains of influenza virus with a 1-fold, 1.5-fold, 2-fold, 3-fold, 4-fold, 5-fold, 6-fold, 7-fold, 8-fold, 9-fold, 10-fold, greater than 10-fold, 1- to 2-fold, 1- to 5-fold, 1- to 10-fold, 2- to 5-fold, 2- to 10-fold, 5- to 10-fold, 10- to 15-fold, or 10- to 20-fold greater affinity than that which they bind to a non-influenza virus hemagglutinin antigen. In specific embodiments, an antibody described herein binds to hemagglutinin from one, two, three or more strains of influenza virus with a 0.5 log, 1 log, 1.5 log, 2 log, 2.5 log, 3 log, 3.5 log, or 4 log greater affinity than that which they bind to a non-influenza virus hemagglutinin antigen.

In a specific embodiment, an antibody described herein binds to and neutralizes two or more strains of influenza viruses that express antigenically distinct HA. In another embodiment, an antibody described herein binds to and neutralizes two or more strains of an influenza A virus hemagglutinin (HA) subtype. In a specific embodiment, an antibody described herein binds to two or more strains of an influenza A virus H1 subtype. In another specific embodiment, an antibody described herein binds to two or more strains of an influenza A virus H5 subtype. In another embodiment, an antibody described herein binds to and neutralizes strains of influenza A virus of two or more HA subtypes. In a specific embodiment, an antibody described herein binds to and neutralizes influenza A viruses of the H1 and H5 subtypes.

In a specific embodiment, an antibody provided herein is the antibody designated GG3 or an antigen-binding fragment thereof. The GG3 antibody is a murine IgG2a antibody. The deduced nucleotide sequences of the VH and VL domains of the antibody GG3 are shown in FIGS. 1 and 2. The deduced amino acid sequences of the VH and VL domains of the antibody GG3 are shown in FIGS. 1 and 2. The CDRs and framework regions of the VH domain and VL domain are indicated in FIGS. 1 and 2. In addition, Table 1, infra, sets forth the nucleic acid and amino acid sequences of the CDRs and framework regions of the variable regions of the antibody GG3. The CDRs and framework regions were determined using the International ImMunoGeneTics ("IMGT") numbering system. See Lefranc et al., Dev. Comp. Immunol. 27:55-77 (2003), which is incorporated herein by reference in its entirety, for a description of the IMGT numbering system. As an alternative to the IMGT numbering system, the Kabat numbering system can be used. Table 2 of Lefranc et al. shows the correspondence between the IMGT and the Kabat numberings. Another alternative to the IMGT numbering system is Chothia. See Chothia and Lesk, J. Mol. Biol. 196:901-917 (1987), which is incorporated herein by reference in its entirety. Further, Oxford's AbM system may be used instead of the IMGT numbering system. A person of ordinary skill in the art would be able to determine the CDRs and framework regions of the variable regions of the GG3 antibody sequence based on the Kabat numbering system, Chothia system, and/or Oxford's AbM system.

TABLE 1

| Region of GG3 | Sequence (nucleic acid or amino acid) |
|---|---|
| VH SEQ ID NO: 1 | cagatccagttggtgcagtctggacctgagctgaagaagcctggagagacagtca<br>agatctcctgcaaggcttctgggtataccttcacaaactatggaatgaactgggtga<br>agcaggctccaggaaagggtttaaagtggatgggctggataaacatctacagtgg<br>agagtcaacatatgttgatgacttcacgggacggtttgccttctctttggaaacctctg<br>ccagcactgcctatttgcagatcaacaacctcaaaaatgaggacatggctacatatt<br>tctgtgcaagatctggggatactatgattacggcgggacggtccttctttgctatgga<br>ctactggggtcaaggaacctcagtcaccgtctcctcagcc |
| VH FR 1 SEQ ID NO: 2 | cagatccagttggtgcagtctggacctgagctgaagaagcctggagagacagtca<br>agatctcctgcaaggcttct |
| VH CDR1 SEQ ID NO: 3 | gggtataccttcacaaactatgga |
| VH FR 2 SEQ ID NO: 4 | atgaactgggtgaagcaggctccaggaaagggtttaaagtggatgggctgg |
| VH CDR2 SEQ ID NO: 5 | ataaacatctacagtggagagtca |
| VH FR 3 SEQ ID NO: 6 | acatatgttgatgacttcacgggacggtttgccttctctttggaaacctctgccagca<br>ctgcctatttgcagatcaacaacctcaaaaatgaggacatggctacatatttctgt |
| VH CDR3 SEQ ID NO: 7 | gcaagatctggggatactatgattacggcgggacggtccttctttgctatggactac |
| VH FR4 SEQ ID NO: 8 | tggggtcaaggaacctcagtcaccgtctcctcagcc |
| VL SEQ ID NO: 9 | gacatccagatgacccagtctccatcctccttatctgcctctctgggagaaagagtc<br>agtctcacttgtcgggcaagtcaggaaattagtggttacttaagctggcttcagcag<br>aaaccagatggaactattaaacgcctgatctacgccgcatccactttagattctggt<br>gtcccaaaaaggttcagtggcagtaggtctgggtcagattattctctctccatcagc<br>agccttgagtctgaagattttgcagactattactgtcttcaatatgctaattatccgtgg<br>tcgttcggtggaggcaccaagctggaaatcaaac |
| VL FR 1 SEQ ID NO: 10 | gacatccagatgacccagtctccatcctccttatctgcctctctgggagaaagagtc<br>agtctcacttgtcgggcaagt |
| VL CDR1 SEQ ID NO: 11 | caggaaattagtggttac |
| VL FR 2 SEQ ID NO: 12 | ttaagctggcttcagcagaaaccagatggaactattaaacgcctgatctac |
| VL CDR2 SEQ ID NO: 13 | gccgcatcc |
| VL FR 3 SEQ ID NO: 14 | actttagattctggtgtcccaaaaaggttcagtggcagtaggtctgggtcagattatt<br>ctctctccatcagcagccttgagtctgaagattttgcagactattactgt |
| VL CDR3 SEQ ID NO: 15 | cttcaatatgctaattatccgtggtcg |
| VH FR4 SEQ ID NO: 16 | ttcggtggaggcaccaagctggaaatcaaac |
| VH SEQ ID NO: 17 | QIQLVQSGPELKKPGETVKISCKASGYTFTNYGMNW<br>VKQAPGKGLKWMGWINIYSGESTYVDDFTGRFAFS<br>LETSASTAYLQINNLKNEDMATYFCARSGDTMITAG<br>RSFFAMDYWGQGTSVTVSSA |
| VH FR1 SEQ ID NO: 18 | Q I Q L V Q S G P E L K K P G E T V K I S C K A S |
| VH CDR1 SEQ ID NO: 19 | G Y T F T N Y G |
| VH FR2 SEQ ID NO: 20 | M N W V K Q A P G K G L K W M G W |
| VH CDR2 SEQ ID NO: 21 | I N I Y S G E S |
| VH FR3 SEQ ID NO: 22 | T Y V D D F T G R F A F S L E T S A S T A Y L Q I N N<br>L K N E D M A T Y F C |
| VH CDR3 SEQ ID NO: 23 | A R S G D T M I T A G R S F F A M D Y |
| VH FR4 SEQ ID NO: 24 | W G Q G T S V T V S S A |
| VL SEQ ID NO: 25 | DIQMTQSPSSLSASLGERVSLTCRASQEISGYLSWLQ<br>QKPDGTIKRLIYAASTLDSGVPKRFSGSRSGSDYSLSI<br>SSLESEDFADYYCLQYANYPWSFGGGTKLEIK |
| VL FR1 SEQ ID NO: 26 | DIQMTQSPSSLSASLGERVSLTCRAS |
| VL CDR1 SEQ ID NO: 27 | QEISGY |
| VL FR2 SEQ ID NO: 28 | LSWLQQKPDGTIKRLIY |
| VL CDR2 SEQ ID NO: 29 | AAS |

TABLE 1-continued

| Region of GG3 | Sequence (nucleic acid or amino acid) |
|---|---|
| VL FR3 SEQ ID NO: 30 | TLDSGVPKRFSGSRSGSDYSLSISSLESEDFADYYC |
| VL CDR3 SEQ ID NO: 31 | LQYANYPWS |
| VL FR4 SEQ ID NO: 32 | FGGGTKLEIK |

In a specific embodiment, the position of a CDR along the VH and/or VL domain of an antibody described herein may vary by one, two, three or four amino acid positions so long as binding to influenza virus HA (e.g., HA of an influenza A virus strain of the H1 subtype, such as HA from A/USSR/92/77 (H1), A/Texas/36/91 (H1), A/New Caledonia/20/99 (H1), A/Brisbane/59/07 (H1), rA/California/04/09 (H1)) is maintained (e.g., substantially maintained, for example, by at least 50%, at least 60%, at least 70%, at least 80%, at least 90%, at least 95% in an assay known in the art or described herein, such as an ELISA). For example, in one embodiment, the position defining a CDR of antibody GG3 may vary by shifting the N-terminal and/or C-terminal boundary of the CDR by one, two, three, or four amino acids, relative to the CDR position depicted in FIGS. 1 and 2, so long as binding to influenza virus HA (e.g., HA of an influenza A virus strain of the H1 subtype, such as HA from A/USSR/92/77 (H1), A/Texas/36/91 (H1), A/New Caledonia/20/99 (H1), A/Brisbane/59/07 (H1), rA/California/04/09 (H1)) is maintained (e.g., substantially maintained, for example, by at least 50%, at least 60%, at least 70%, at least 80%, at least 90%, at least 95% in an assay known in the art or described herein, such as an ELISA).

Provided herein are antibodies that bind to an influenza virus HA comprising one, two or three complementarity determining regions (CDRs) of the variable heavy chain region of the antibody GG3 and one, two or three CDRs of the variable light chain region of the antibody GG3. In certain embodiments, an antibody that binds to an influenza virus HA (e.g., HA of an influenza A virus strain of the H1 or H5 subtype), comprises (or alternatively, consists of) a VH CDR1 and a VL CDR1; a VH CDR1 and a VL CDR2; a VH CDR1 and a VH CDR3; a VH CDR2 and a VL CDR1; VH CDR2 and a VL CDR2; a VH CDR2 and a VL CDR3; a VH CDR3 and a VL CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1; a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2 and a VH CDR3 and a VL CDR1; a VH CDR1, a VH CDR2 and a VH CDR3 and a VL CDR2; a VH CDR1, a VH CDR2 and a VH CDR3 and a VL CDR3; a VH CDR1, a VH CDR2 and a VL CDR1 and a VL CDR2; a VH CDR1, a VH CDR2 and a VL CDR1 and a VL CDR3; a VH CDR1, a VH CDR3, a VL CDR1 and a VL CDR2; a VH CDR1, a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; a VH CDR1, VH CDR2, a VH CDR3, a VL CDR1, a VL CDR2, and a VL CDR3; or any combination thereof of the VH CDRs and VL CDRs of the antibody GG3. In specific embodiments, such antibodies bind to HA from a strain of the H1 subtype of influenza A virus and in certain embodiments, such antibodies neutralize a strain of the H1 subtype of influenza A virus. In some embodiments, such antibodies bind to HA from a strain of the H5 subtype of influenza A virus and in certain embodiments, such antibodies neutralize a strain of the H5 subtype of influenza A virus. In certain embodiments, such antibodies bind to HA from a strain from each of the H1 and H5 subtypes of influenza A virus and in certain embodiments, such antibodies neutralize a strain from each of the H1 and H5 subtypes of influenza A virus.

In another embodiment, an antibody (or antigen-binding fragment thereof), which binds to an influenza virus hemagglutinin (e.g., HA of an influenza A virus strain of the H1 or H5 subtype), comprises one, two, three, four, five or all six complementarity determining regions (CDRs) of the antibody GG3. In certain embodiments, an antibody (or an antigen-binding fragment thereof), which binds to an influenza virus hemagglutinin (e.g., HA of an influenza A virus strain of the H1 or H5 subtype), comprises: a variable light (VL) domain or light chain comprising a VL complementarity determining region (CDR)1, VL CDR2, and VL CDR3 having the amino acid sequences of SEQ ID NOs: 27, 29, and 31, respectively; and a variable heavy (VH) domain or heavy chain comprising a VH CDR1, VH CDR2, and VH CDR3 having the amino acid sequences of SEQ ID NOs: 19, 21 and 23, respectively.

In one embodiment, provided herein is an antibody (or an antigen-binding fragment thereof), which binds to an influenza virus hemagglutinin (e.g., HA of an influenza A virus strain of the H1 or H5 subtype), comprising a light chain or VL domain comprising VL CDR1, VL CDR2, and VL CDR3 having the amino acid sequences of SEQ ID NO: 27, 29 and 31, respectively. In certain embodiments, the light chain or VL domain comprises one, two or three of framework region (FR)1, FR2, FR3, and FR4 having the amino acid sequences of SEQ ID NO: 26, 28, 30 and 32, respectively. In some embodiments, the light chain or VL domain comprises FR1, FR2, FR3, and FR4 having the amino acid sequences of SEQ ID NO: 26, 28, 30, and 32, respectively. In other embodiments, the light chain or VL domain comprises the human framework regions.

In another embodiment, provided herein is an antibody (or an antigen-binding fragment thereof), which binds to an influenza virus hemagglutinin (e.g., HA of an influenza A virus strain of the H1 or H5 subtype), wherein the heavy chain or VH domain comprises VH CDR1, VH CDR2, and VH CDR3 having the amino acid sequences of SEQ ID NO:19, 21 and 23, respectively. In certain embodiments, the heavy chain or VH domain comprises one, two or three of FR1, FR2, FR3, and FR4 having the amino acid sequences of SEQ ID NO: 18, 20, 22 and 24, respectively. In some embodiments, the heavy chain or VH domain comprises FR1, FR2, FR3, and FR4 having the amino acid sequences of SEQ ID NO: 18, 20, 22 and 24, respectively. In other embodiments, the heavy chain or VH domain comprises the human framework regions.

In some embodiments, an antibody (or an antigen-binding fragment thereof) described herein, which binds to an influenza virus hemagglutinin (e.g., HA of an influenza A virus strain of the H1 or H5 subtype), comprises a VL domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO:25. In certain embodiments, an antibody (or antigen-binding fragment thereof) described herein, which binds to an influenza virus HA (e.g., HA of an influenza A virus strain of the H1 or H5 subtype), comprises a VH domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO:17. In some embodiments, an antibody (or an antigen-binding fragment thereof), which binds to an influenza virus hemagglutinin (e.g., HA of an influenza A virus strain of the H1 or H5 subtype), comprises a VL domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO:25; and a VH domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO:17. In accordance with these embodiments, the CDRs of the antibody or an antigen-binding fragment thereof are, in certain embodiments, identical to the CDRs of the antibody GG3.

In some embodiments, an antibody (or an antigen-binding fragment thereof) described herein, which binds to an influenza virus hemagglutinin (e.g., HA of an influenza A virus strain of the H1 or H5 subtype), comprises a VL domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO:25; and VH domain comprising the amino acid sequence of SEQ ID NO:17. In some embodiments, an antibody (or an antigen-binding fragment thereof) described herein, which binds to an influenza virus hemagglutinin (e.g., HA of an influenza A virus strain of the H1 or H5 subtype), comprises a VL domain comprising the amino acid sequence of SEQ ID NO:25; and a VH domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO:17. In accordance with these embodiments, the CDRs of the antibody or an antigen-binding fragment thereof are, in certain embodiments, identical to the CDRs of the antibody GG3.

In specific embodiments, an antibody (or antigen-binding fragment thereof) described herein, which binds to an influenza virus hemagglutinin, comprises a VL domain comprising the amino acid sequence of SEQ ID NO:25; and/or a VH domain comprising the amino acid sequence of SEQ ID NO:17.

In some embodiments, an antibody (or an antigen-binding fragment thereof) described herein, which binds to an influenza virus hemagglutinin (e.g., HA of an influenza A virus strain of the H1 or H5 subtype), comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO:25. In certain embodiments, an antibody (or antigen-binding fragment thereof) described herein, which binds to an influenza virus HA (e.g., HA of an influenza A virus strain of the H1 or H5 subtype), comprises a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO:17. In some embodiments, an antibody (or an antigen-binding fragment thereof), which binds to an influenza virus hemagglutinin, comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO:25; and a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO:17. In accordance with these embodiments, the CDRs of the antibody or an antigen-binding fragment thereof are, in certain embodiments, identical to the CDRs of the antibody GG3.

In some embodiments, an antibody (or an antigen-binding fragment thereof) described herein, which binds to an influenza virus hemagglutinin (e.g., HA of an influenza A virus strain of the H1 or H5 subtype), comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO:25; and a heavy chain comprising the amino acid sequence of SEQ ID NO:17. In some embodiments, an antibody (or an antigen-binding fragment thereof) described herein described herein, which binds to an influenza virus hemagglutinin (e.g., HA of an influenza A virus strain of the H1 or H5 subtype), comprises a light chain comprising the amino acid sequence of SEQ ID NO:25; and a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO:17. In accordance with these embodiments, the CDRs of the antibody or an antigen-binding fragment thereof are, in certain embodiments, identical to the CDRs of the antibody GG3.

In specific embodiments, an antibody (or antigen-binding fragment thereof) described herein, which binds to an influenza virus hemagglutinin (e.g., HA of an influenza A virus strain of the H1 or H5 subtype), comprises a light chain comprising the amino acid sequence of SEQ ID NO:25; and/or a heavy chain comprising the amino acid sequence of SEQ ID NO:17.

Techniques known to one of skill in the art can be used to determine the percent identity between two amino acid sequences or between two nucleotide sequences. Generally, to determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/ total number of positions×100%). In one embodiment, the two sequences are the same length. In a certain embodiment, the percent identity is determined over the entire length of an amino acid sequence or nucleotide sequence.

The determination of percent identity between two sequences (e.g., amino acid sequences or nucleic acid sequences) can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In some embodiments, an antibody described herein (or an antigen-binding fragment thereof), which binds to an influenza virus HA (e.g., HA of an influenza A virus strain of the H1 or H5 subtype), comprises one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO:17 or 25. In a specific embodiment, an antibody described herein (or an antigen-binding fragment thereof), which binds to an influenza virus HA (e.g., HA of an influenza A virus strain of the H1 or H5 subtype), comprises one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 17 or 25. In certain embodiments, an antibody described herein (or an antigen-binding fragment thereof), which binds to an influenza virus HA (e.g., HA of an influenza A virus strain of the H1 or H5 subtype), comprises one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 17 or 25, wherein the one or more amino acid substitutions is in one, two, three or more of the framework regions. In specific embodiments, none of the amino acid substitutions are located within the CDRs (e.g., SEQ ID NO: 19, 21, 23, 27, 29, or 31). In specific embodiments, all of the amino acid substitutions are in the framework regions.

In certain embodiments, an antibody (or an antigen-binding fragment thereof) described herein, which binds to an influenza virus HA (e.g., HA of an influenza A virus strain of the H1 or H5 subtype), comprises one or more (e.g., 1, 2, 3, 4, 5 or 6) amino acid substitutions (e.g., conservative amino acid substitutions) in the amino acid sequence of one, two or more of the following: the VL CDR1, the VL CDR2, the VL CDR3, the VL CDR1 and VL CDR2, the VL CDR2 and VL CDR3, the VL CDR1 and VL CDR3, or the VL CDR1, VL CDR2 and VL CDR3 of the antibody GG3. In some embodiments, an antibody (or an antigen-binding fragment thereof) described herein, which binds to an influenza virus HA (e.g., HA of an influenza A virus strain of the H1 or H5 subtype), comprises one or more (e.g., 1, 2, 3, 4, 5 or 6) amino acid substitutions (e.g., conservative amino acid substitutions) in the amino acid sequence of one, two or more of the following: the VH CDR1, the VH CDR2, the VH CDR3, the VH CDR1 and VH CDR2, the VH CDR2 and VH CDR3, the VH CDR1 and VH CDR3, or the VH CDR1, VH CDR2 and VH CDR3 of the antibody GG3. In certain embodiments, an antibody (or an antigen-binding fragment thereof) described herein, which binds to an influenza virus HA (e.g., HA of an influenza A virus strain of the H1 or H5 subtype), comprises one or more (e.g., 1, 2, 3, 4, 5 or 6) amino acid substitutions (e.g., conservative amino acid substitutions) in the amino acid sequence of one, two or more of the following: the VL CDR1; the VL CDR2; the VL CDR3; the VH CDR1; the VH CDR2; and/or the VH CDR3 of the antibody GG3.

Also provided herein are antibodies that bind the same or an overlapping epitope as an antibody described herein (e.g., antibody GG3), i.e., antibodies that compete for binding to influenza virus HA (e.g., an HA of an influenza A virus strain of the H1 or H5 subtype), or bind epitopes which overlap with epitopes bound by the antibodies described herein. Antibodies that recognize such epitopes can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as influenza virus HA. Numerous types of competitive binding assays are known, for example: solid phase direct or indirect radioimmunoassay (RIA), solid phase direct or indirect enzyme immunoassay (EIA), sandwich competition assay (see Stahli et al., (1983) Methods in Enzymology 9:242); solid phase direct biotin-avidin EIA (see Kirkland et al., (1986) J. Immunol. 137:3614); solid phase direct labeled assay, solid phase direct labeled sandwich assay (see Harlow and Lane, (1988) Antibodies: A Laboratory Manual, Cold Spring Harbor Press); solid phase direct label RIA using I-125 label (see Morel et al., (1988) Mol. Immunol. 25(1):7); solid phase direct biotin-avidin EIA (Cheung et al., (1990) Virology 176:546); and direct labeled RIA. (Moldenhauer et al., (1990) Scand J. Immunol. 32:77). Typically, such an assay involves the use of purified antigen (e.g., influenza virus HA) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener et al., J. Immunol., 1983, 130:2308-2315; Wagener et al., J. Immunol. Methods, 1984, 68:269-274; Kuroki et al., Cancer Res., 1990, 50:4872-4879; Kuroki et al., Immunol. Invest., 1992, 21:523-538; Kuroki et al., Hybridoma, 1992, 11:391-407, and *Using Antibodies: A Laboratory Manual*, Ed Harlow and David Lane editors (Cold Springs Harbor Laboratory Press, Cold Springs Harbor, N. Y., 1999), pp. 386-389.

In certain aspects, competition binding assays can be used to determine whether an antibody is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with an antibody described herein, e.g., antibody GG3, an antibody comprising VH CDRs and VL CDRs of antibody GG3, or a humanized monoclonal antibody comprising VH CDRs and VL CDRs of antibody GG3. In a particular embodiment, a humanized antibody derived from a mouse monoclonal antibody is able to compete (e.g., in a dose dependent manner) with the mouse monoclonal antibody.

In certain aspects, epitope mapping assays, well known to one of skill in the art, can be performed to ascertain the epitope (e.g., conformational epitope) to which an antibody described herein specifically binds. Examples of such epitope mapping assays described in the art include crystallography (see, e.g., Blechman et al., 1993, J. Biol. Chem. 268:4399-4406; Cho et al., 2003, Nature, 421:756-760), deuterium exchange, and alanine-scanning mutagenesis (see, e.g., Vajdos et al., 2002, J Mol Biol. 320(2):415-28; Nisihara et al., 2001, J Immunol. 167(6):3266-75; and Zhang et al., 1999, Int Immunol. 11(12):1935-44).

In a specific embodiment, provided herein is an antibody (or antigen-binding fragment thereof), which binds to an influenza virus hemagglutinin (e.g., HA from A/USSR/92/77 (H1), A/Texas/36/91 (H1), A/New Caledonia/20/99 (H1), A/Brisbane/59/07 (H1), rA/California/04/09 (H1), or rA/Vietnam/1203/04 (H5)), wherein said antibody (or antigen-binding fragment thereof) competes (e.g., in a dose-dependent manner) for binding to the influenza virus hemagglutinin (e.g., HA from A/USSR/92/77 (H1), A/Texas/36/91 (H1), A/New Caledonia/20/99 (H1), A/Brisbane/59/07 (H1), rA/California/04/09 (H1), or rA/Vietnam/1203/04 (H5)) with a reference antibody comprising: a VL domain or light chain comprising a VL CDR1, VL CDR2, and VL CDR3 having the amino acid sequences of SEQ ID NOs: 27, 29, and 31, respectively; and a VH domain or heavy chain comprising a VH CDR1, VH CDR2, and VH CDR3 having the amino acid sequences of SEQ ID NOs: 19, 21 and 23, respectively. In another embodiment, provided herein is an antibody (or antigen-binding fragment thereof), which binds to an influenza virus hemagglutinin (e.g., HA from A/USSR/92/77 (H1), A/Texas/36/91 (H1), A/New Caledonia/20/99 (H1), A/Brisbane/59/07 (H1), rA/California/04/09 (H1), or rA/Vietnam/1203/04 (H5)), wherein said antibody (or antigen-binding fragment thereof) competes (e.g., in a dose-dependent manner) for binding to the influenza virus hemagglutinin (e.g., HA from A/USSR/92/77 (H1), A/Texas/36/91 (H1), A/New Caledonia/20/99 (H1), A/Brisbane/59/07 (H1), rA/California/04/09 (H1), or rA/Vietnam/1203/04 (H5)) with a reference antibody comprising a VL domain comprising the amino acid sequence of SEQ ID NO:25; and VH domain comprising the amino acid sequence of SEQ ID NO:17. In another embodiment, provided herein is an antibody (or antigen-binding fragment thereof), which binds to an influenza virus hemagglutinin (e.g., HA from A/USSR/92/77 (H1), A/Texas/36/91 (H1), A/New Caledonia/20/99 (H1), A/Brisbane/59/07 (H1), rA/California/04/09 (H1), or rA/Vietnam/1203/04 (H5)), wherein said antibody (or antigen-binding fragment thereof) competes (e.g., in a dose-dependent manner) for binding to the influenza virus hemagglutinin (e.g., HA from A/USSR/92/77 (H1), A/Texas/36/91 (H1), A/New Caledonia/20/99 (H1), A/Brisbane/59/07 (H1), rA/California/04/09 (H1), or rA/Vietnam/1203/04 (H5)) with a reference antibody comprising a light chain comprising the amino acid sequence of SEQ ID NO:25; and a heavy chain comprising the amino acid sequence of SEQ ID NO:17.

In a specific embodiment, provided herein is an antibody (or an antigen-binding fragment thereof), which binds to an influenza virus hemagglutinin (e.g., HA from A/USSR/92/77 (H1), A/Texas/36/91 (H1), A/New Caledonia/20/99 (H1), A/Brisbane/59/07 (H1), rA/California/04/09 (H1), or rA/Vietnam/1203/04 (H5)), wherein said antibody binds to the same epitope as the epitope of a reference antibody comprising: a VL domain or light chain comprising a VL CDR1, VL CDR2, and VL CDR3 having the amino acid sequences of SEQ ID NOs: 27, 29, and 31, respectively; and a VH domain or heavy chain comprising a VH CDR1, VH CDR2, and VH CDR3 having the amino acid sequences of SEQ ID NOs: 19, 21 and 23, respectively. In another specific embodiment, provided herein is an antibody (or an antigen-binding fragment thereof), which binds to an influenza virus hemagglutinin (e.g., HA from A/USSR/92/77 (H1), A/Texas/36/91 (H1), A/New Caledonia/20/99 (H1), A/Brisbane/59/07 (H1), rA/California/04/09 (H1), or rA/Vietnam/1203/04 (H5)), wherein said antibody binds to the same epitope as the epitope of a reference antibody comprising a VL domain comprising the amino acid sequence of SEQ ID NO:25; and a VH domain comprising the amino acid sequence of SEQ ID NO:17. In another specific embodiment, provided herein is an antibody (or an antigen-binding fragment thereof), which binds to an influenza virus hemagglutinin (e.g., HA from A/USSR/92/77 (H1), A/Texas/36/91 (H1), A/New Caledonia/20/99 (H1), A/Brisbane/59/07 (H1), rA/California/04/09 (H1), or rA/Vietnam/1203/04 (H5)), wherein said antibody binds to the same epitope as the epitope of a reference antibody comprising a light chain comprising the amino acid sequence of SEQ ID NO:25; and a heavy chain comprising the amino acid sequence of SEQ ID NO:17.

In specific aspects, provided herein are antibodies (e.g., antibodies comprising the CDRs of antibody GG3 or an antibody which binds to the same epitope as that of antibody GG3) that have a high binding affinity (e.g., antibodies having a $K_D$ of less than 100 nM, 50 nM, 10 nM, 1 nM, 500 pM, 200 pM, 100 pM, or 50 pM) for an influenza virus HA (e.g., an HA of influenza A virus strain of the H1 and/or H5 subtypes). In a specific embodiment, an antibody described herein has an association rate constant or $k_{on}$ rate (antibody (Ab)+antigen (Ag)$\xrightarrow{k_{on}}$Ab-Ag) of at least $2\times10^5 M^{-1} s^{-1}$, at least $5\times10^5 M^{-1} s^{-1}$, at least $10^6 M^{-1} s^{-1}$, at least $5\times10^6 M^{-1} s^{-1}$, at least $10^7 M^{-1} s^{-1}$, at least $5\times10^7 M^{-1} s^{-1}$, or at least $10^8 M^{-1} s^{-1}$. In a certain embodiment, an antibody described herein has a $k_{on}$ of at least $2\times10^5 M^{-1} s^{-1}$, at least $5\times10^5 M^{-1} s^{-1}$, at least $10^6 M^{-1} s^{-1}$, at least $5\times10^6 M^{-1} s^{-1}$, at least $10^7 M^{-1} s^{-1}$, at least $5\times10^7 M^{-1} s^{-1}$, or at least $10^8 M^{-1} s^{-1}$.

In another embodiment, an antibody described herein has a $k_{off}$ rate ((Ab-Ag)$\xrightarrow{k_{off}}$antibody (Ab)+antigen) of less than $10^{-1} s^{-1}$, less than $5\times10^{-1} s^{-1}$, less than $10^{-2} s^{-1}$, less than $5\times10^{-2} s^{-1}$, less than $10^{-3} s^{-1}$, less than $5\times10^{-3} s^{-1}$, less than $10^{-4} s^{-1}$, less than $5\times10^{-4} s^{-1}$, less than $10^{-5} s^{-1}$, less than $5\times10^{-5} s^{-1}$, less than $10^{-6} s^{-1}$, less than $5\times10^{-6} s^{-1}$, less than $10^{-7} s^{-1}$, less than $5\times10^{-7} s^{-1}$, less than $10^{-8} s^{-1}$, less than $5\times10^{-8} s^{-1}$, less than $10^{-9} s^{-1}$, less than $5\times10^{-9} s^{-1}$, or less than $10^{-10} s^{-1}$. In a specific embodiment, an antibody described herein has a $k_{on}$ of less than $5\times10^{-4} s^{-1}$, less than $10^{-5} s^{-1}$, less than $5\times10^{-5} s^{-1}$, less than $10^{-6} s^{-1}$, less than $5\times10^{-6} s^{-1}$, less than $10^{-7} s^{-1}$, less than $5\times10^{-7} s^{-1}$, less than $10^{-8} s^{-1}$, less than $5\times10^{-8} s^{-1}$, less than $10^{-9} s^{-1}$, less than $5\times10^{-9} s^{-1}$, or less than $10^{-10} s^{-1}$.

In another embodiment, an antibody described herein has an affinity constant or $K_a$ ($k_{on}/k_{off}$) of at least $10^2 M^{-1}$, at least $5\times10^2 M^{-1}$, at least $10^3 M^{-1}$, at least $5\times10^3 M^{-1}$, at least $10^4 M^{-1}$, at least $5\times10^4 M^{-1}$, at least $10^5 M^{-1}$, at least $5\times10^5 M^{-1}$, at least $10^6 M^{-1}$, at least $5\times10^6 M^{-1}$, at least $10^7 M^{-1}$, at least $5\times10^7 M^{-1}$, at least $10^8 M^{-1}$, at least $5\times10^8 M^{-1}$, at least $10^9 M^{-1}$, at least $5\times10^9 M^{-1}$, at least $10^{10} M^{-1}$, at least $5\times10^{10} M^{-1}$, at least $10^{11} M^{-1}$, at least $5\times10^{11} M^{-1}$, at least $10^{12} M^{-1}$, at least $5\times10^{12} M^{-1}$, at least $10^{13} M^{-1}$, at least $5\times10^{13} M^{-1}$, at least $10^{14} M^{-1}$, at least $5\times10^{14} M^{-1}$, at least $10^{15} M^{-1}$, or at least $5\times10^{15} M^{-1}$.

In a particular embodiment, an antibody described herein has a dissociation constant or $K_D$ ($k_{off}/k_{on}$) of less than $10^{-2}$ M, less than $5\times10^{-2}$ M, less than $10^{-3}$ M, less than $5\times10^{-3}$ M, less than $10^{-4}$ M, less than $5\times10^{-4}$ M, less than $10^{-5}$ M, less than $5\times10^{-5}$ M, less than $10^{-6}$ M, less than $5\times10^{-6}$ M, less than $10^{-7}$ M, less than $5\times10^{-7}$ M, less than $10^{-8}$ M, less than $5\times10^{-8}$ M, less than $10^{-9}$ M, less than $5\times10^{-9}$ M, less than $10^{-10}$ M, less than $5\times10^{-10}$ M, less than $10^{-11}$ M, less than $5\times10^{-11}$ M, less than $10^{-12}$ M, less than $5\times10^{-12}$ M, less than $10^{-13}$ M, less than $5\times10^{-13}$ M, less than $10^{-14}$ M, less than $5\times10^{-14}$ M, less than $10^{-15}$ M, or less than $5\times10^{-15}$ M.

In specific embodiments, an antibody (e.g., antibody comprising the CDRs of antibody GG3 or an antibody which binds to the same epitope as that of antibody GG3) binds to an influenza virus HA (e.g., an HA of influenza A virus strain of the H1 and/or H5 subtypes), and has a dissociation constant ($K_D$) of less than 500,000 pM (500 nM), less than 100,000 pM (100 nM), less than 50,000 pM (50 nM), less than 10,000 pM (10 nM), less than 3,000 pM (3 nM), less than 2,500 pM (2.5 nM), less than 2,000 pM, less than 1,500 pM, less than 1,000 pM, less than 750 pM, less than 500 pM, less than 250 pM, less than 200 pM, less than 150 pM, less than 100 pM, less than 75 pM as assessed using an assay described herein or known to one of skill in the art (e.g., a Biacore™ assay) (Biacore™ International AB, Uppsala, Sweden). In a specific embodiment, an antibody described herein (e.g., antibody comprising the CDRs of antibody GG3 or an antibody which binds to the same epitope as that of antibody GG3) binds to an influenza virus HA (e.g., an HA of influenza A virus strain of the H1 and/or H5 subtypes), and has a $K_D$ in the range of from 100 to 100,000 pM, 100 to 75,000 pM, 100 to 50,000 pM, 100 to 40,000 pM, 100 to 30,000 pM, 100 to 20,000 pM, 100 to 10,000 pM, 25 to 1,000 pM, 25 to 500 pM, 25 to 250 pM, 25 to 100 pM, or 25 to 50 pM as assessed using methods described herein or known to one of skill in the art (e.g., a Biacore™ assay, assay using KinExA 3000 instrument). In a particular embodiment, an antibody described herein (e.g., antibody comprising the CDRs of antibody GG3 or an antibody which binds to the same epitope as that of antibody GG3) binds to an influenza virus HA (e.g., an HA of influenza A virus strain of the H1 and/or H5 subtypes), and has a $K_D$ of about 1 nM to about 25 nM, or any value in between, as assessed using methods described herein or known to one of skill in the art (e.g., a Biacore™ assay, assay using KinExA 3000 instrument). In a particular embodiment, an antibody described herein (e.g., antibody comprising the CDRs of antibody GG3 or an antibody which binds to the same epitope as that of antibody GG3) binds to an influenza virus HA (e.g., an HA of influenza A virus strain of the H1 and/or H5 subtypes), and has a $K_D$ of about 1 nM, 1.5 nM, 2 nM, 2.5 nM, 3 nM, 3.5 nM, 4 nM, 4.5 nM, 5 nM, 5.5 nM, 6 nM, 6.5 nM, 7 nM, 8 nM, 9 nM, 10 nM, 11 nM, 12 nM, 13 nM, 14 nM, 15 nM, 16 nM, 17 nM, 18 nM, 19 nM, 20 nM, or 21 nM, as assessed using methods described herein or known to one of skill in the art (e.g., a Biacore™ assay, assay using KinExA 3000 instrument).

In specific embodiments, an antibody described herein, which binds to a an influenza virus HA (e.g., HA of an influenza A virus strain of the H1 or H5 subtype), and has a concentration at 50% binding to HA of less than 500 nM, less than 250 nM, less than 100 nM, less than 50 nM, less than 1000 pM, less than 750 pM, less than 500 pM, less than 250 pM, less than 200 pM, less than 150 pM, less than 100 pM, less than 75 pM as assessed using an assay described herein or known to one of skill in the art (e.g., an ELISA such as described in Section 6, infra). In a specific embodiment, an antibody described herein, which binds to an influenza virus HA (e.g., HA of an influenza A virus strain of the H1 or H5 subtype), and has a concentration at 50% binding to antigen in the range of from 1 to 500 nM, 1 to 250 nM, 1 to 100 nM, 1 to 75 nM, 1 to 50 nM, 1 to 40 nM, 1 to 30 nM, 1 to 20 nM, 0.1 to 50 nM, or 0.5 to 50 nM as assessed using methods described herein or known to one of skill in the art (e.g., an ELISA such as described in section 6, infra). In a particular embodiment, an antibody described herein, which binds to an influenza virus HA (e.g., HA of an influenza A virus strain of the H1 or H5 subtype), and has a concentration at 50% binding to HA of about 1 nM to about 50 nM, or any value in between, as assessed using methods described herein or known to one of skill in the art (e.g., an ELISA such as described in Section 6, infra). In a particular embodiment, an antibody described herein, which binds to an influenza virus HA (e.g., HA of an influenza A virus strain of the H1 or H5 subtype), and has a concentration at 50% binding of about 0.5 nM, 1 nM, 1.5 nM, 2 nM, 2.5 nM, 3 nM, 3.5 nM, 4 nM, 4.5 nM, 5 nM, 5.5 nM, 6 nM, 6.5 nM, 7 nM, 8 nM, 9 nM, 10 nM, 11 nM, 12 nM, 13 nM, 14 nM, 15 nM, 16 nM, 17 nM, 18 nM, 19 nM, 20 nM, 30 nM, 40 nM, 50 nM, 60 nM, 70 nM, 80 nM, 90 nM, 100 nM, 150 nM, 200 nM, 250 nM, 300 nM, 350 nM, 400 nM, or 500 nM, or less, as assessed using methods described herein or known to one of skill in the art (e.g., an ELISA, such as described in Section 6, infra).

In specific embodiments, an antibody which is an antigen-binding fragment of a whole or entire antibody, e.g., Fab fragment, has comparable affinity to an influenza virus HA (e.g., HA of an influenza A virus strain of the H1 or H5 subtype) relative to the affinity of the whole or entire antibody. In certain embodiments, an antibody which is an antigen-binding fragment of a whole or entire antibody, e.g., Fab fragment, binds to an influenza virus HA (e.g., HA of an influenza A virus strain of the H1 or H5 subtype) and has a $K_D$ that is comparable to the $K_D$ of the whole or entire antibody as assessed using methods described herein or known to one of skill in the art (e.g., a Biacore™ assay, assay using KinExA 3000 instrument). In certain embodiments, an antibody which is an antigen-binding fragment of a whole or entire antibody, e.g., Fab fragment, binds to an influenza virus HA (e.g., HA of an influenza A virus strain of the H1 or H5 subtype) and has a $K_D$ that is less than the $K_D$ of the whole or entire antibody as assessed using methods described herein or known to one of skill in the art (e.g., a Biacore™ assay, assay using KinExA 3000 instrument). In particular embodiments, an antibody which is an antigen-binding fragment of a whole or entire antibody, e.g., Fab fragment, binds to an influenza virus HA (e.g., HA of an influenza A virus strain of the H1 or H5 subtype) and has a $K_D$ that is about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 75%, or 85%, less than the $K_D$ of the whole or entire antibody as assessed using methods described herein or known to one of skill in the art (e.g., a Biacore™ assay, assay using KinExA 3000 instrument). In particular embodiments, an antibody which is an antigen-binding fragment of a whole or entire antibody, e.g., Fab fragment, binds to an influenza virus HA (e.g., HA of an influenza A virus strain of the H1 or H5 subtype) and has a $K_D$ that is at most about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 65% or 75% less than the $K_D$ of the whole or entire antibody as assessed using methods described herein or known to one of skill in the art (e.g., a Biacore™ assay, assay using KinExA 3000 instrument).

Methods for determining affinity of an antibody to its target antigen are readily available and described in the art. For example, the affinities and binding properties of an antibody for its target antigen, can be determined by a variety of in vitro assay methods (biochemical or immunological based assays) known in the art such as equilibrium methods (e.g., enzyme-linked immunoabsorbent assay (ELISA), or radioimmunoassay (RIA)), or kinetics (e.g., Biacore™ analysis), and other methods such as indirect binding assays, competitive inhibition assays, fluorescence resonance energy transfer (FRET), immunoprecipitation, gel electrophoresis and chromatography (e.g., gel filtration). These and other methods can utilize a label on one or more of the components being examined and/or employ a variety of detection methods including but not limited to chromogenic, fluorescent, luminescent, or isotopic labels. In certain embodiments, use of labels is not necessary, e.g., Biacore™ systems utilize the natural phenomenon of surface plasmon resonance (SPR) to deliver data in real time, without the use of labels. A detailed description of binding affinities and kinetics can be found in Paul, W. E., ed., *Fundamental Immunology*, 4th Ed. (Lippincott-Raven, Philadelphia 1999), which focuses on antibody-immunogen interactions.

In certain embodiments, an antibody (or an antigen-binding fragment thereof) described herein, which binds to an influenza virus HA, comprises a VH domain or heavy chain comprising FR1, FR2, FR3 and FR4 of the antibody GG3. In some embodiments, an antibody (or an antigen-binding fragment thereof) described herein, which binds to an influenza virus HA, comprises a VL domain or light chain comprising FR1, FR2, FR3 and FR4 of the antibody GG3. In a specific embodiment, an antibody (or an antigen-binding fragment thereof) described herein, which binds to an influenza virus HA, comprises framework regions of the antibody GG3.

In specific embodiments, an antibody (or an antigen-binding fragment thereof) described herein, which binds to an influenza virus HA, comprises framework regions (e.g., framework regions of the VL domain and/or VH domain) that are human framework regions or derived from human framework regions. The framework region may be naturally occurring or consensus framework regions (see, e.g., Sui et al., 2009, Nature Structural & Molecular Biology 16:265-273). Non-limiting examples of human framework regions are described in the art, e.g., see Kabat et al. (1991) *Sequences of Proteins of Immunological Interest*, Fifth Edition, U.S. Department of Health and Human Services, NIH Publication No. 91-3242). In certain embodiment, an antibody described herein comprises framework regions (e.g., framework regions of the VL domain and/or VH domain) that are primate (e.g., non-human primate) framework regions or derived from primate (e.g., non-human primate) framework regions.

For example, CDRs from antigen-specific non-human antibodies, typically of rodent origin (e.g., mouse or rat), are grafted onto homologous human or non-human primate acceptor frameworks. In one embodiment, the non-human primate acceptor frameworks are from Old World apes. In a specific embodiment, the Old World ape acceptor framework is from *Pan troglodytes, Pan paniscus* or *Gorilla gorilla*. In a particular embodiment, the non-human primate acceptor frameworks are from the chimpanzee *Pan troglodytes*. In a particular embodiment, the non-human primate acceptor frameworks are Old World monkey acceptor frameworks. In a specific embodiment, the Old World monkey acceptor frameworks are from the genus *Macaca*. In a certain embodiment, the non-human primate acceptor frameworks are is derived from the cynomolgus monkey *Macaca cynomolgus*. Non-human primate framework sequences are described in U.S. Patent Application Publication No. US 2005/0208625.

In specific aspects, provided herein is an antibody comprising an antibody light chain and heavy chain, e.g., a separate light chain and heavy chain.

With respect to the light chain, in a specific embodiment, the light chain of an antibody described herein is a kappa light chain. In another specific embodiment, the light chain of an antibody described herein is a lambda light chain. In yet another specific embodiment, the light chain of an antibody described herein is a human kappa light chain or a human lambda light chain. In a particular embodiment, an antibody described herein, which binds to an influenza virus HA, comprises a light chain wherein the amino acid sequence of the VL domain can comprise any amino acid sequence described herein, and wherein the constant region of the light chain comprises the amino acid sequence of a human kappa or lambda light chain constant region. Non-limiting examples of human constant region sequences have been described in the art, e.g., see U.S. Pat. No. 5,693,780 and Kabat et al. (1991) *Sequences of Proteins of Immuno-* logical Interest, Fifth Edition, U.S. Department of Health and Human Services, NIH Publication No. 91-3242.

With respect to the heavy chain, in a specific embodiment, the heavy chain of an antibody described herein can be an alpha (α), delta (δ), epsilon (ε), gamma (γ) or mu (μ) heavy chain. In another specific embodiment, the heavy chain of an antibody described can comprise a human alpha (α), delta (δ), epsilon (ε), gamma (γ) or mu (μ) heavy chain. In a particular embodiment, an antibody described herein, which binds to an influenza virus HA, comprises a heavy chain wherein the amino acid sequence of the VH domain can comprise any amino acid sequence described herein, and wherein the constant region of the heavy chain comprises the amino acid sequence of a human gamma (γ) heavy chain constant region. Non-limiting examples of human constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242.

In a specific embodiment, an antibody described herein, which binds to an influenza virus HA (e.g., HA from an influenza A virus strain of the H1 subtype, such as HA from A/USSR/92/77 (H1), A/Texas/36/91 (H1), A/New Caledonia/20/99 (H1), A/Brisbane/59/07 (H1), rA/California/04/09 (H1)) comprises a VL domain and a VH domain comprising any amino acid sequences described herein, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In another specific embodiment, an antibody described herein, which binds to an influenza virus HA (e.g., HA from an influenza A virus strain of the H1 subtype, such as HA from A/USSR/92/77 (H1), A/Texas/36/91 (H1), A/New Caledonia/20/99 (H1), A/Brisbane/59/07 (H1), rA/California/04/09 (H1)) comprises a VL domain and a VH domain comprising any amino acid sequences described herein, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. In a particular embodiment, the constant regions comprise the amino acid sequences of the constant regions of a human IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule.

In particular embodiments, an antibody described herein is an IgG2a antibody, and optionally comprises a kappa light chain.

The antibodies described herein can be affinity matured using techniques known to one of skill in the art. The antibodies described herein can be chimerized using techniques known to one of skill in the art. A chimeric antibody is a molecule in which different portions of the antibody are derived from different immunoglobulin molecules. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816, 567, 4,816,397, and 6,331,415, which are incorporated herein by reference in their entirety.

The antibodies described herein can be humanized. A humanized antibody is an antibody which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')$_2$, Fab, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. Examples of VL and VH constant domains that can be used in certain embodiments include, but are not limited to, C-kappa and C-gamma-1 (nG1m) described in Johnson et al. (1997) *J. Infect. Dis.* 176, 1215-1224 and those described in U.S. Pat. No. 5,824, 307. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework and CDR sequences, more often 90%, and most preferably greater than 95%.

The antibodies provided herein include derivatives that are chemically modified, i.e., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In particular embodiments, the glycosylation of antibodies described herein, in particular glycosylation of a variable region of an antibody described herein, is modified. For example, an aglycoslated antibody can be made (i.e., the antibody lacks glycosylation) or an antibody comprising a mutation or substitution at one or more glycosylation sites to eliminate glycosylation at the one or more glycosylation sites can be made. Glycosylation can be altered to, for example, increase the affinity of the antibody for an influenza virus HA. Such carbohydrate modifications can be accomplished by, for example, altering one or more sites of glycosylation within the antibody sequence. For example, one or more amino acid substitutions can be made that result in elimination of one or more variable region (e.g., VL and/or VH CDRs or VL and/or VH FRs) glycosylation sites to thereby eliminate glycosylation at that site. Such aglycosylation can increase the affinity of the antibody for an influenza virus HA. Such an approach is described in further detail in U.S. Pat. Nos. 5,714,350 and 6,350,861.

Glycosylation can occur via N-linked (or asparagine-linked) glycosylation or O-linked glycosylation. N-linked glycosylation involves carbohydrate modification at the side-chain $NH_2$ group of an asparagine amino acid in a polypeptide. O-linked glycosylation involves carbohydrate modification at the hydroxyl group on the side chain of a serine, threonine, or hydroxylysine amino acid.

In certain embodiments, aglycosylated antibodies can be produced in bacterial cells which lack the necessary glycosylation machinery. Cells with altered glycosylation machinery have been described in the art and can be used as host cells in which to express recombinant antibodies described herein to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 03/035835; WO 99/54342.

Antibodies with reduced fucose content have been reported to have an increased affinity for Fc receptors, such as, e.g., FcγRIIIa. Accordingly, in certain embodiments, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

In certain embodiments, one, two or more mutations (e.g., amino acid substitutions) are introduced into the Fc region of an antibody described herein or a fragment thereof (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to increase the affinity of the antibody for an Fc receptor (e.g., an activated Fc receptor) on the surface of an effector cell. Mutations in the Fc region of an antibody or fragment thereof that increase the affinity of an antibody for an Fc receptor and techniques for introducing such mutations into the Fc receptor or fragment thereof are known to one of skill in the art. Examples of mutations in the Fc receptor of an antibody that can be made to increase the affinity of the antibody for an Fc receptor are described in, e.g., Smith, P., et al. (2012) PNAS. 109:6181-6186, which is incorporated herein by reference.

5.1.1 Antibodies with Increased Half-Lives

Provided herein are antibodies, wherein said antibodies are modified to have an extended (or increased) half-life in vivo. In particular, provided herein are modified antibodies which have a half-life in a subject, preferably a mammal and most preferably a human, of from about 3 days to about 180 days (or more), and in some embodiments greater than 3 days, greater than 7 days, greater than 10 days, greater than 15 days, greater than 20 days, greater than 25 days, greater than 30 days, greater than 35 days, greater than 40 days, greater than 45 days, greater than 50 days, at least about 60 days, greater than 75 days, greater than 90 days, greater than 105 days, greater than 120 days, greater than 135 days, greater than 150 days, greater than 165 days, or greater than 180 days.

In a specific embodiment, modified antibodies having an increased half-life in vivo are generated by introducing one or more amino acid modifications (i.e., substitutions, insertions or deletions) into an IgG constant domain, or FcRn-binding fragment thereof (preferably a Fc or hinge-Fc domain fragment). See, e.g., International Publication Nos. WO 02/060919; WO 98/23289; and WO 97/34631; and U.S. Pat. No. 6,277,375; each of which is incorporated herein by reference in its entirety. In a specific embodiment, the modified antibodies may have one or more amino acid modifications in the second constant CH2 domain (residues 231-340 of human IgG1) and/or the third constant CH3 domain (residues 341-447 of human IgG1), with numbering according to the Kabat numbering system (e.g., the EU index in Kabat).

In some embodiments, to prolong the in vivo serum circulation of antibodies, inert polymer molecules such as high molecular weight polyethyleneglycol (PEG) are attached to the antibodies with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein.

In another embodiment, antibodies are conjugated to albumin in order to make the antibody more stable in vivo or have a longer half-life in vivo. The techniques are well-known in the art, see, e.g., International Publication Nos. WO 93/15199, WO 93/15200, and WO 01/77137; and European Patent No. EP 413,622, all of which are incorporated herein by reference.

5.1.2 Antibody Conjugates

In some aspects, provided herein are antibodies, or antigen-binding fragments thereof, conjugated or recombinantly fused to a diagnostic, detectable or therapeutic agent or any other molecule. The conjugated or recombinantly fused antibodies can be useful, e.g., for monitoring or prognosing the onset, development, progression and/or severity of an influenza virus disease as part of a clinical testing procedure, such as determining the efficacy of a particular therapy. In certain aspects, the conjugated or recombinantly fused antibodies can be useful in preventing, managing and/or treating an influenza virus disease or influenza virus. Antibodies described herein can also be conjugated to a molecule (e.g., polyethylene glycol) which can affect one or more biological and/or molecular properties of the antibodies, for example, stability (e.g., in serum), half-life, solubility, and antigenicity.

In specific embodiments, a conjugate comprises an antibody described herein and a molecule (e.g., therapeutic or drug moiety), wherein the antibody is linked directly to the molecule, or by way of one or more linkers. In certain embodiments, an antibody is covalently conjugated to a molecule. In a particular embodiment, an antibody is non-covalently conjugated to a molecule.

In certain embodiments, an antibody described herein, or an antigen-binding fragment thereof, is conjugated to one or more molecules (e.g., therapeutic or drug moiety) directly or indirectly via one or more linker molecules. In particular embodiments, a linker comprises 1, 2, 3, 4, 5, 6, 7, 8, 9, 10, 11, 12, 13, 14, 15, or 20 amino acid residues. In certain embodiments, a linker consists of 1 to 10 amino acid residues, 1 to 15 amino acid residues, 5 to 20 amino acid residues, 10 to 25 amino acid residues, 10 to 30 amino acid residues, or 10 to 50 amino acid residues. In particular embodiments, a linker is an enzyme-cleavable linker or a disulfide linker. In a specific embodiment, the cleavable linker is cleavable via an enzyme such an aminopeptidase, an aminoesterase, a dipeptidyl carboxy peptidase, or a protease of the blood clotting cascade.

In one embodiment, a linker is hydrolyzed at a pH in the range of 3.0 and pH 4.0 for about 1-24 hours, and at a temperature from about 20 to 50° C., preferably 37° C. In a specific embodiment, a linker is stable in the blood stream but is cleaved or hydrolyzed once it is inside the targeted cells. In certain embodiments, a linker comprises one or more triazole-containing linkers (see, e.g., International Patent Application Publication No. WO 2007/018431, which is incorporated by reference herein in its entirety). Non-limiting examples of linkers and spacers for incorporation into antibody-drug conjugates described herein are disclosed in International Patent Application Publication Nos. WO 2007/018431, WO 2004/043493, and WO 2002/083180.

In specific aspects, diagnosis and detection can be accomplished, for example, by coupling the antibody or an antigen-binding fragment thereof to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Se, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and non-radioactive paramagnetic metal ions.

Provided are antibodies described herein, or antigen-binding fragments thereof, conjugated or recombinantly fused to a therapeutic moiety (or one or more therapeutic moieties) and uses of such antibodies. The antibody can be conjugated or recombinantly fused to a therapeutic moiety, such as a cytotoxin, e.g., a cytostatic or cytocidal agent, a therapeutic agent or a radioactive metal ion, e.g., alpha-emitters.

Further, provided herein are uses of the antibodies conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, β-interferon, γ-interferon, α-interferon, interleukin-2 ("IL-2"), interleukin-4 ("IL-4"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-18 ("IL-18"), interleukin-23 ("IL-23"), granulocyte macrophage colony stimulating factor ("GM-CSF"), granulocyte colony stimulating factor ("G-CSF")), a growth factor, or a defensin. The therapeutic moiety or drug conjugated or recombinantly fused to an antibody should be chosen to achieve the desired prophylactic or therapeutic effect(s). In certain embodiments, an antibody conjugate may be used for the prophylactic or therapeutic uses described herein. In certain embodiments, the antibody is a modified antibody. A clinician or other medical personnel should consider the following when deciding on which therapeutic moiety or drug to conjugate or recombinantly fuse to an antibody: the nature of the disease, the severity of the disease, and the condition of the subject.

In addition, an antibody or an antigen-binding fragment thereof described herein can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7,10-tetraaza-cyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10): 2483-90; Peterson et al., 1999, Bioconjug. Chem. 10(4): 553-7; and Zimmerman et al., 1999, Nucl. Med. Biol. 26(8):943-50, each incorporated by reference in their entireties.

Provided herein are antibodies or antigen-binding fragments thereof recombinantly fused or chemically conjugated (including both covalent and non-covalent conjugations) to a heterologous protein or polypeptide (or fragment thereof, preferably to a polypeptide of about 10, about 20, about 30, about 40, about 50, about 60, about 70, about 80, about 90 or about 100 amino acids) to generate fusion proteins. In particular, provided herein are fusion proteins comprising an antigen-binding fragment of a monoclonal antibody (e.g., a Fab fragment, Fd fragment, Fv fragment, F(ab)$_2$ fragment, a VH domain, a VH CDR, a VL domain or a VL CDR) and a heterologous protein, polypeptide, or peptide. In a specific embodiment, the heterologous protein, polypeptide, or peptide that the antibody is fused to is useful for targeting the antibody to a particular cell type.

In one embodiment, a fusion protein provided herein comprises the antibody GG3 and a heterologous polypeptide. In another embodiment, a fusion protein provided herein comprises an antigen-binding fragment of the antibody GG3 and a heterologous polypeptide. In another embodiment, a fusion protein provided herein comprises a VH domain having the amino acid sequence of the VH domain of the antibody GG3, or a VL domain having the amino acid sequence of the VL domain of the antibody GG3 and a heterologous polypeptide. In another embodiment, a fusion protein provided herein comprises one, two, or more VH CDRs having the amino acid sequence of the VH CDRs of the antibody GG3 and a heterologous polypeptide. In another embodiment, a fusion protein comprises one, two, or more VL CDRs having the amino acid sequence of the VL CDRs of the antibody GG3 and a heterologous polypeptide. In another embodiment, a fusion protein provided herein comprises at least one VH domain and at least one VL domain of the antibody GG3 and a heterologous polypeptide. In yet another embodiment, a fusion protein provided herein comprises at least one VH CDR and at least one VL CDR of the antibody GG3 and a heterologous polypeptide. In certain embodiments, the above-referenced antibodies comprise a modified IgG (e.g., IgG1) constant domain, or FcRn binding fragment thereof (e.g., the Fc domain or hinge-Fc domain), described herein.

Moreover, antibodies can be fused to marker sequences, such as a peptide to facilitate purification. In preferred embodiments, the marker amino acid sequence is a hexa-histidine peptide (i.e., His-tag), such as the tag provided in a pQE vector (QIAGEN, Inc.), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

Methods for fusing or conjugating therapeutic moieties (including polypeptides) to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367, 166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992; which are incorporated herein by reference in their entireties.

In particular, fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of the monoclonal antibodies described herein (or an antigen-binding fragment thereof) (e.g., antibodies with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies, or the encoded antibodies, may be altered by being subjected to random mutagenesis by error-prone PCR, random nucleotide insertion or other methods prior to recombination. A polynucleotide encoding a monoclonal antibody described herein (or an antigen-binding fragment thereof) may be recombined with one or more components, motifs, sections, parts, domains, fragments, etc. of one or more heterologous molecules.

An antibody can also be conjugated to a second antibody to form an antibody heteroconjugate as described by Segal in U.S. Pat. No. 4,676,980, which is incorporated herein by reference in its entirety.

An antibody can also linked directly or indirectly to one or more antibodies to produce bispecific/multispecific antibodies.

An antibody can also be attached to solid supports, which are particularly useful for immunoassays or purification of an antigen. Such solid supports include, but are not limited to, glass, cellulose, polyacrylamide, nylon, polystyrene, polyvinyl chloride or polypropylene.

5.2 Polynucleotides

In certain aspects, provided herein are polynucleotides comprising a nucleotide sequence encoding an antibody described herein or a fragment thereof (e.g., a VL domain and/or VH domain) that binds to an influenza virus HA (e.g., HA of an influenza A virus strain of the H1 or H5 subtype), and vectors, e.g., vectors comprising such polynucleotides for recombinant expression in host cells (e.g., *E. coli* and mammalian cells).

In particular aspects, provided herein are polynucleotides comprising nucleotide sequences encoding antibodies (e.g., a murine, chimeric, or humanized antibody) or antigen-binding fragments thereof, which binds to an influenza virus HA (e.g., HA of an influenza A virus strain of the H1 or H5 subtype) and comprises an amino acid sequence as described herein, as well as antibodies which compete with such antibodies for binding to an influenza virus HA (e.g., HA of an influenza A virus strain of the H1 or H5 subtype) (e.g., in a dose-dependent manner), or which binds to the same epitope as that of such antibodies. In particular embodiments, a polynucleotide described herein encodes an antibody or an antigen-binding fragment thereof which comprises a VL domain and a VH domain of antibody GG3. In particular embodiments, a polynucleotide described herein encodes an antibody or an antigen-binding fragment thereof which comprises a VL domain comprising the amino acid sequence of SEQ ID NO:25 and/or a VH domain comprising the amino acid of SEQ ID NO:17. In certain embodiments, a polynucleotide described herein encodes such a VL domain (e.g., a VL domain comprising the amino acid sequence of SEQ ID NO:25). In certain embodiments, a polynucleotide described herein encodes such a VH domain (e.g., a VH domain comprising the amino acid sequence of SEQ ID NO:17). In some embodiments, a polynucleotide described herein encodes for an antibody that binds to influenza virus HA (e.g., HA of an influenza A virus strain of the H1 or H5 subtype), wherein the antibody comprises 1, 2, or 3 VH CDRs and/or 1, 2, or 3 VL CDRs of the antibody GG3.

In particular embodiments, a polynucleotide described herein encodes an antibody or an antigen-binding fragment thereof, which binds to an influenza virus HA (e.g., HA of an influenza A virus strain of the H1 or H5 subtype), comprising VL CDRs and/or VH CDRs of antibody GG3. For example, in a specific embodiment, a polynucleotide described herein encodes an antibody or an antigen-binding fragment thereof which comprises a VL domain comprising CDR1, CDR2, and CDR3 having the amino acid sequences of SEQ ID NOs:27, 29 and 31, respectively, and/or a VH domain comprising CDR1, CDR2, and CDR3 having the amino acid sequences of SEQ ID NOs: 19, 21, and 23, respectively. In certain aspects, provided herein are polynucleotides comprising a nucleotide sequence encoding the light chain or heavy chain of an antibody described herein. The polynucleotides can comprise nucleotide sequences encoding a light chain or a VL domain, comprising the VL FRs and CDRs of an antibody described herein. The polynucleotides can comprise nucleotide sequences encoding a heavy chain, or a VH domain, comprising the VH FRs and CDRs of antibodies described herein. In specific embodiments, a polynucleotide described herein encodes a VL domain comprising the amino acid sequence of SEQ ID NO:25. In specific embodiments, a polynucleotide described herein encodes a VH domain comprising the amino acid sequence of SEQ ID NO:17.

In particular embodiments, a polynucleotide described herein encodes a VL domain, wherein the polynucleotide comprises the nucleic acid sequence of SEQ ID NO: 9. In particular embodiments, a polynucleotide described herein encodes a VH domain, wherein the polynucleotide comprises the nucleic acid sequence of SEQ ID NO:1. In certain embodiments, a polynucleotide encodes an antibody described herein, wherein the polynucleotide comprises the nucleic acid sequence of SEQ ID NO:9 encoding a VL domain and the nucleic acid sequence of SEQ ID NO:1 encoding a VH domain.

In particular embodiments, a polynucleotide described herein encodes a VL domain, wherein the polynucleotide comprises a nucleic acid sequence that is at least 80%, 85%, 90%, 91%, 92%, 93%, 94%, 95%, 96%, 97%, or 98% identical to the nucleic acid sequence of SEQ ID NO:9. In particular embodiments, a polynucleotide described herein encodes a VH domain, wherein the polynucleotide comprises a nucleic acid sequence that is at least 80%, 85%, 90%, 91%, 92%, 93%, 94%, 95%, 96%, 97%, or 98% identical to the nucleic acid sequence of SEQ ID NO:1. In particular embodiments, a polynucleotide described herein comprises nucleic acid sequences that encode a VL domain and a VH domain, wherein the nucleic acid sequence encoding the VL domain is at least 80%, 85%, 90%, 91%, 92%, 93%, 94%, 95%, 96%, 97%, or 98% identical to the nucleic acid sequence of SEQ ID NO:9 and the nucleic acid sequence encoding the VH domain is at least 80%, 85%, 90%, 91%, 92%, 93%, 94%, 95%, 96%, 97%, or 98% identical to the nucleic acid sequence of SEQ ID NO:1.

In specific embodiments, polynucleotides described herein have at least 80%, 85%, 90%, 91%, 92%, 93%, 94%, 95%, 96%, 97%, or 98% sequence identity to a polynucleotide comprising SEQ ID NO:9 encoding a VL domain of an antibody described herein. In specific embodiments, polynucleotides described herein have at least 80%, 85%, 90%, 91%, 92%, 93%, 94%, 95%, 96%, 97%, or 98% sequence identity to a polynucleotide comprising SEQ ID NO:1 encoding a VH domain of an antibody described herein.

In particular embodiments, a polynucleotide described herein encodes a light chain, wherein the polynucleotide comprises the nucleic acid sequence of SEQ ID NO:9. In particular embodiments, a polynucleotide described herein encodes a heavy cha in, wherein the polynucleotide comprises the nucleic acid sequence of SEQ ID NO:1. In particular embodiments, a polynucleotide(s) described herein encodes a light chain and a heavy chain, wherein the polynucleotide(s) comprises the nucleic acid sequence of SEQ ID NO:9 and the nucleic acid sequence of SEQ ID NO:1. In particular embodiments, a polynucleotide described herein comprises nucleic acid sequences that encode a light chain and a heavy chain, wherein the nucleic acid sequence encoding the light chain comprises a nucleotide sequence that is at least 80%, 85%, 90%, 91%, 92%, 93%, 94%, 95%, 96%, 97%, or 98% identical to the nucleic acid sequence of SEQ ID NO:9 and/or the nucleic acid sequence encoding the heavy chain comprises a nucleotide sequence that is at least 80%, 85%, 90%, 91%, 92%, 93%, 94%, 95%, 96%, 97%, or 98% identical to the nucleic acid sequence of SEQ ID NO:1.

In specific aspects, provided herein is a polynucleotide comprising a nucleotide sequence encoding an antibody provided herein (e.g., murine, chimeric, or humanized antibody) which competitively blocks (e.g., in a dose dependent manner), antibody GG3 from specific binding to an influenza virus HA, as determined using assays known to one of skill in the art or described herein (e.g., ELISA competitive assays).

In a specific embodiment, a polynucleotide provided herein comprises a nucleotide sequence encoding a kappa light chain (e.g., human kappa light chain). In another specific embodiment, a polynucleotide provided herein comprises a nucleotide sequence encoding a lambda light chain (e.g., human lambda light chain).

In a specific embodiment, a polynucleotide provided herein comprises a nucleotide sequence encoding an IgG1 heavy chain (e.g., human IgG1 heavy chain) of an antibody described herein. In another specific embodiment, a polynucleotide provided herein comprises a nucleotide sequence encoding IgG4 heavy chain (e.g., human IgG4 heavy chain). In another specific embodiment, a polynucleotide provided herein comprises a nucleotide sequence encoding IgG2 heavy chain (e.g., human IgG2 heavy chain).

In another particular embodiment, a polynucleotide provided herein comprises a nucleotide sequence encoding an antibody described herein (or an antigen-binding fragment thereof), which binds to an influenza virus HA, wherein the antibody comprises a light chain and a heavy chain, and wherein (i) the light chain comprises a VL domain comprising a VL CDR1, VL CDR2, and VL CDR3 having the amino acid sequences of the VL CDRs of antibody GG3; (ii) the heavy chain comprises a VH domain comprising a VH CDR1, VH CDR2, and VH CDR3 having the amino acid sequences of the VH CDRs of antibody GG3; (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 heavy chain.

In another particular embodiment, a polynucleotide provided herein comprises a nucleotide sequence encoding an antibody described herein (or an antigen-binding fragment thereof), which binds to an influenza virus HA, wherein the antibody comprises a light chain and a heavy chain, and wherein (i) the light chain comprises a VL domain comprising a VL CDR1, VL CDR2, and VL CDR3 having the amino acid sequences of the VL CDRs of antibody GG3; (ii) the heavy chain comprises a VH domain comprising a VH CDR1, VH CDR2, and VH CDR3 having the amino acid sequences of the VH CDRs of antibody GG3; (iii) the light chain further comprises a constant light chain domain comprising the amino acid sequence of the constant domain of a mouse kappa light chain; and (iv) the heavy chain further comprises a constant heavy chain domain comprising the amino acid sequence of the constant domain of a mouse IgG1 heavy chain.

In certain embodiments, with respect to a polynucleotide provided herein comprising a nucleotide sequence encoding a VL domain and VH domain of any of the antibodies described herein, the polynucleotide of the VL domain further comprises primate (e.g., human) framework regions; and the VH domain further comprises primate (e.g., human) framework regions.

In a specific embodiment, provided herein are polynucleotides comprising a nucleotide sequence encoding an antibody, or a fragment or domain thereof (e.g., VL domain or VH domain), designated herein as antibody GG3.

Also provided are polynucleotides that hybridize under high stringency, intermediate or lower stringency hybridization conditions to antisense polynucleotides of polynucleotides that encode an antibody described herein or a fragment thereof (e.g., VL domain or VH domain). In specific embodiments, a polynucleotide described herein hybridizes under high stringency, or intermediate stringency hybridization conditions to an antisense polynucleotide of a polynucleotide encoding a VL domain, e.g., SEQ ID NO:9, and/or VH domain, e.g., SEQ ID NO:10, provided herein. In specific embodiments, a polynucleotide described herein hybridizes under high stringency, or intermediate stringency hybridization conditions to an antisense polynucleotide of a polynucleotide comprising SEQ ID NO:1 or 9. In specific embodiments, a polynucleotide described herein hybridizes under high stringency, or intermediate stringency hybridization conditions to an antisense polynucleotide of a polynucleotide comprising SEQ ID NO:1 or 9, provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3.

Also provided herein are polynucleotides encoding an antibody or a fragment thereof that are optimized, e.g., by codon/RNA optimization, replacement with heterologous signal sequences, and elimination of mRNA instability elements. Methods to generate optimized nucleic acids encoding an antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an antibody encoded by polynucleotides that have not been optimized.

In certain embodiments, an optimized polynucleotide sequence encoding an antibody described herein or a fragment thereof (e.g., VL region and/or VH region) can hybridize to an antisense polynucleotide of an unoptimized polynucleotide encoding an antibody described herein or a fragment thereof (e.g., VL region and/or VH region). In specific embodiments, an optimized nucleotide sequence encoding an antibody described herein or a fragment thereof (e.g., VL region and/or VH region) hybridizes under high stringency conditions to an antisense polynucleotide of an unoptimized polynucleotide encoding an antibody described herein or a fragment thereof (e.g., VL region and/or VH region). In a specific embodiment, an optimized nucleotide sequence encoding an antibody described herein or a fragment thereof (e.g., VL region and/or VH region) hybridizes under intermediate or lower stringency hybridization conditions to an antisense polynucleotide of an unoptimized polynucleotide encoding an antibody described herein or a fragment thereof (e.g., VL region and/or VH region). Information regarding hybridization conditions have been described, see, e.g., U.S. Patent Application Publication No. US 2005/0048549 (e.g., paragraphs 72-73), which is incorporated herein by reference in its entirety.

The polynucleotides can be obtained, and the nucleotide sequence of the polynucleotides determined, by any method known in the art. Nucleotide sequences encoding antibodies described herein, and modified forms of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light domain and/or the variable heavy domain of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding an antibody or an antigen-binding fragment thereof described herein can be readily isolated and sequenced using conventional procedures (e.g., by using oligonucleotide probes that are capable of binding specifically to genes encoding the heavy and light chains of the antibody). Hybridoma cells can serve as a source of such DNA. Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of antibodies in the recombinant host cells.

In phage display methods, functional antibody domains are displayed on the surface of phage particles which carry the polynucleotide sequences encoding them. In particular, a library of DNA sequences encoding VH and VL domains are generated (e.g., amplified from animal cDNA libraries such as human cDNA libraries or random libraries are generated by chemical synthesis). The DNA encoding the VH and VL domains are recombined together with an scFv linker by PCR and cloned into a phagemid vector. The vector is electroporated in *E. coli* and the *E. coli* is infected with helper phage. Phage expressing an antigen-binding domain that binds to a particular antigen can be selected or identified with antigen, e.g., using labeled antigen or antigen bound or captured to a solid surface or bead. After phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produced Fab, Fab' and F(ab')$_2$ fragments can also be employed using methods known in the art such as those disclosed in PCT Publication No. WO 92/22324; Mullinax et al., 1992, *BioTechniques*, 12(6):864-869; Sawai et al., 1995, *AJRI*, 34:26-34; and Better et al., 1988, *Science*, 240:1041-1043.

Antibodies can be isolated from antibody phage libraries generated using the techniques described in McCafferty et al., *Nature*, 348:552-554 (1990). Clackson et al., *Nature*, 352:624-628 (1991). Marks et al., *J. Mol. Biol.*, 222:581-597 (1991) describe the isolation of murine and human antibodies, respectively, using phage libraries. Chain shuffling can be used in the production of high affinity (nM range) human antibodies (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable domain, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

In a non-limiting example, the Dyax (Cambridge, Mass.) technology platform can be used to convert Fab-phage or Fabs to complete IgG antibodies, such as the Dyax pR rapid reformatting vectors (RR). Briefly, by PCR, a Fab-encoding DNA fragment is inserted into a Dyax pR-RRV between a eukaryotic leader sequence and an IgG heavy chain constant region cDNA. Antibody expression is driven by the human cytomegalovirus (hCMV). In a second cloning step, bacterial regulatory elements are replaced by the appropriate eukaryotic sequences (i.e., the IRES (internal ribosome entry site) motif). The expression vector can also include the SV40 origin of replication. The Dyax pRh1(a,z), pRh1(f), pRh4 and pRm2a are expression vectors allowing expression of reformatted FAbs as human IgG1 (isotype a,z), human IgG1 (isotype F), human IgG4, and mouse IgG2a, respectively. Expressing vectors can be introduced into a suitable host cell (e.g., HEK293T cells, CHO cells)) for expression and purification.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

In some embodiments, a polynucleotide(s) encoding an antibody or an antigen-binding fragment provided herein is isolated. In other embodiments, a polynucleotide(s) encoding an antibody or an antigen-binding fragment provided herein is not isolated. In yet other embodiments, a polynucleotide(s) encoding an antibody or an antigen-binding fragment thereof provided herein is integrated, e.g., into chromosomal DNA or an expression vector.

5.3 Production of Antibody

Provided herein are methods for making an antibody described herein or a fragment thereof, which binds to an influenza virus HA. In certain aspects, a method for making an antibody described herein or a fragment thereof, which binds to an influenza virus HA, comprises the step of culturing a cell (e.g., host cell or hybridoma cell) that expresses the antibody. In certain embodiments, the method for making an antibody described herein further comprises the step of purifying the antibody expressed by the cell. In certain aspects, a method for making an antibody described herein or a fragment thereof, which immunospecifically binds to an influenza virus HA, comprises the step of culturing a cell (e.g., host cell or hybridoma cell) that comprises polynucleotides or vectors encoding the antibody or fragments thereof. In a particular aspect, provided herein are methods for producing an antibody described herein, comprising expressing such antibody from a host cell.

In certain aspects, provided herein are cells (e.g., host cells) expressing (e.g., recombinantly expressing) the antibodies described herein (or an antigen-binding fragment thereof) and related expression vectors. Provided herein are vectors (e.g., expression vectors) comprising polynucleotides comprising nucleotide sequences encoding antibodies or a fragment thereof for recombinant expression in host cells, preferably in mammalian cells. Also provided herein are host cells comprising such polynucleoide or such vectors for recombinantly expressing antibodies described herein (e.g., antibody GG3). In a particular aspect, provided herein are hybridoma cells expressing an antibody described herein, e.g., antibody GG3.

Antibodies described herein (or an antigen-binding fragment thereof) that bind to an influenza virus HA can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N. Y., 1981). The term "monoclonal antibody" as used herein is not limited to antibodies produced through hybridoma technology.

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., influenza virus HA) used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)). Additionally, a RIMMS (repetitive immunization multiple sites) technique can be used to immunize an animal (Kilptrack et al., 1997 Hybridoma 16:381-9, incorporated by reference in its entirety).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against an influenza virus HA. The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI 1640 medium. Alternatively, clonal cells can be isolated using a semi-solid agar supplemented with HAT (Stemcell Technologies). In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

In some embodiments, mice (or other animals, such as rats, monkeys, donkeys, pigs, sheep, goats, hamsters, or dogs) can be immunized with an antigen (e.g., an influenza virus HA) and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma clones are then assayed by methods known in the art for cells that secrete antibodies capable of binding a polypeptide of the antigen (e.g., an influenza virus HA). Ascites fluid, which generally contains high levels of antibodies, can be generated by immunizing mice with positive hybridoma clones.

Accordingly, described herein are methods of making antibodies described herein by culturing a hybridoma cell secreting an antibody. In certain embodiments, the method of making an antibody described herein further comprises the step of purifying the antibody.

In specific embodiments, the hybridoma is generated by fusing splenocytes isolated from a mouse (or other animal, such as rat, monkey, donkey, pig, sheep, or dog) immunized with an influenza virus HA with myeloma cells and then screening the hybridomas resulting from the fusion for hybridoma clones that secrete an antibody able to bind to the influenza virus HA. In certain embodiments, the hybridoma is generated by fusing lymph nodes isolated from a mouse (or other animal, such as rat, monkey, donkey, pig, sheep, or dog) immunized with an influenza virus HA with myeloma cells, and then screening the hybridomas resulting from the fusion for hybridoma clones that secrete an antibody able to bind to the influenza virus HA.

Antibodies described herein include antibody fragments which recognize an influenza virus HA and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043.

In one aspect, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it can be preferable to use human, humanized or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741.

A chimeric antibody is a molecule in which different portions of the antibody are derived from different immunoglobulin molecules. For example, a chimeric antibody can contain a variable region of a mouse monoclonal antibody fused to a constant region of a human antibody. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415.

In some embodiments, humanized antibodies are produced. A humanized antibody is capable of binding to a predetermined antigen and comprises a framework region having substantially the amino acid sequence of a human immunoglobulin and CDRs having substantially the amino acid sequence of a non-human immunoglobulin (e.g., a murine immunoglobulin). Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73

(1994). See also U.S. Patent Pub. No. US 2005/0042664 A1 (Feb. 24, 2005), which is incorporated by reference herein in its entirety.

In some embodiments, humanized antibodies are produced. In particular embodiments, an antibody described herein, which binds to the same epitope of an influenza virus HA as antibody GG3, is a humanized antibody. In particular embodiments, an antibody described herein, which competitively blocks (e.g., in a dose-dependent manner) antibody GG3 from binding to an influenza virus HA, is a humanized antibody. In certain embodiments, an antibody described herein, which binds to an influenza virus HA, is a humanized antibody derived from antibody GG3. For example, such a humanized antibody comprises a VL domain comprising VL CDR1, VL CDR2, and VL CDR3, and/or a VH domain comprising VH CDR1, VH CDR2, and VH CDR3, of the antibody from which it was derived (e.g., antibody GG3).

Human antibodies can be produced using any method known in the art. In certain embodiments, provided herein are human antibodies which can compete with antibody GG3 for specific binding to an influenza virus HA. In certain embodiments, provided herein are human antibodies which bind to the same epitope of an influenza virus HA as the epitope to which antibody GG3 binds. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., an influenza virus HA). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633, 425, 5,569,825, 5,661,016, 5,545,806, 5,814,318, and 5,939, 598.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., an influenza virus HA). Such methods are known and are described in the art, see, e.g., Shinmoto et al., Cytotechnology, 2004, 46:19-23; Naganawa et al., Human Antibodies, 2005, 14:27-31.

In some embodiments, human antibodies can be generated by inserting polynucleotides encoding human CDRs (e.g., VL CDRs and/or VH CDRs) of an antibody into an expression vector containing nucleotide sequences encoding human framework region sequences. In certain embodiments, such expression vectors further comprise nucleotide sequences encoding a constant region of a human light and/or heavy chain. In some embodiments, human antibodies can be generated by inserting human CDRs (e.g., VL CDRs and/or VH CDRs) of an antibody obtained from a phage library into such human expression vectors.

In certain embodiments, a human antibody can be generated by selecting human CDR sequences that are homologous (or substantially homologous) to non-human CDR sequences of a non-human antibody, and selecting human framework sequences that are homologous (or substantially homologous) to non-human framework sequences of a non-human antibody.

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301.

Bispecific antibodies are antibodies that have binding specificities for at least two different epitopes. Exemplary bispecific antibodies may bind to two different epitopes of an antigen or to two different epitopes of two different antigens. In specific embodiments, a bispecific antibody has two distinct antigen-binding domains, wherein each domain specifically binds to a different antigen. Other such antibodies may bind a first antigen (e.g., an influenza virus HA) and further bind a second antigen. Bispecific antibodies can be prepared as full-length antibodies or antibody fragments (e.g., F(ab'): bispecific antibodies).

Methods for making bispecific antibodies are known in the art. (See, for example, Millstein et al., Nature, 305:537-539 (1983); Traunecker et al., EMBO J., 10:3655-3659 (1991); Suresh et al., Methods in Enzymology, 121:210 (1986); Kostelny et al., J. Immunol., 148(5):1547-1553 (1992); Hollinger et al., Proc. Natl. Acad. Sci. USA, 90:6444-6448 (1993); Gruber et al., J. Immunol., 152:5368 (1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and EP 03089.)

Further, antibodies that bind to an influenza virus HA can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

Recombinant expression of an antibody described herein (e.g., a full-length antibody, heavy and/or light chain of an antibody, or a single chain antibody described herein) that binds to an influenza virus HA, can for example, involve construction of vectors (e.g., expression vectors) containing a polynucleotide that encodes the antibody or fragments thereof (e.g., VL domain and/or VH domain). Once a polynucleotide encoding an antibody molecule, heavy and/ or light chain of an antibody, or antigen-binding fragment thereof described herein has been obtained, a vector for the production of the antibody molecule can be produced by recombinant DNA technology using techniques well-known in the art. Methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and the variable domain of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or antigen-binding fragment thereof, or a single chain antibody described herein, operably linked to a promoter for expression of such sequences in the host cell. In certain embodiments, e.g., for the expression of double-chained antibodies, vectors encoding both the heavy and light chains individually can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain of an antibody described herein, or a fragment thereof, and a second vector comprising a polynucleotide encoding a light chain of an antibody described herein, or a fragment thereof. In other embodiments, a first host cell comprises a first vector comprising a polynucleotide encoding a heavy chain of an antibody described herein, or a fragment thereof, and a second host cell comprises a second vector comprising a polynucleotide encoding a light chain of an antibody described herein.

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, MDCK, HEK 293, NS0, PER.C6, VERO, CRL7O3O, HsS78Bst, HeLa, and NIH 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, a mammalian expression vector is pOptiVEC™ or pcDNA3.3. Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In certain embodiments, antibodies described herein are produced by CHO cells or NS0 cells. In a specific embodiment, the expression of nucleotide sequences encoding antibodies described herein (or fragments thereof) which immunospecifically bind to an influenza virus HA is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., 1983, EMBO 12:1791), in which the antibody coding sequence can be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, Methods in Enzymol. 153:51-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, COS, MDCK, HEK 293, NIH 3T3, W138, BT483, Hs578T, HTB2, BT2O and T47D, NS0 (a murine myeloma cell line that does not endogenously produce any immunoglobulin chains), CRL7O3O and HsS78Bst cells. In certain embodiments, humanized monoclonal antibodies described herein are produced in mammalian cells, such as CHO cells.

For long-term, high-yield production of recombinant proteins, stable expression is preferred. For example, cell lines which stably express the antibody molecule can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the antibody molecule. Such engineered cell lines can be particularly useful in screening and evaluation of compositions that interact directly or indirectly with the antibody molecule.

A number of selection systems can be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology can be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds.), Current Protocols in Human Genetics, John Wiley & Sons, NY (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody or an antigen-binding fragment thereof described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly such preparations of the antibody have less than about 30%, 20%, 10%, 5% (by dry weight) of chemical precursors or compounds other than the antibody of interest. In a specific embodiment, antibodies described herein are isolated or purified.

5.4 Compositions

Provided herein are compositions comprising an antibody having the desired degree of purity in a physiologically acceptable carrier, excipient or stabilizer (*Remington's Pharmaceutical Sciences* (1990) Mack Publishing Co., Easton, Pa.). In a specific embodiment, the compositions comprise an antibody conjugated to a moiety such as described in Section 5.1.2. In certain embodiments, the compositions comprise an antibody that has been modified to increase its half-life. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an antibody, and optionally one or more additional prophylactic or therapeutic agents, in a pharmaceutically acceptable carrier. In a specific embodiment, pharmaceutical compositions comprise an effective amount of an antibody, and optionally one or more additional prophylactic of therapeutic agents, in a pharmaceutically acceptable carrier. See Section 5.5.3, infra, for examples of prophylactic or therapeutic agents. In some embodiments, the antibody is the only active ingredient included in the pharmaceutical composition. Pharmaceutical compositions described herein can be useful in the prevention and/or treatment of influenza virus infection. Further, pharmaceutical compositions described herein can be useful in the prevention, treatment and/or management of influenza virus disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An antibody can be formulated as an aerosol for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An antibody can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

In certain embodiments, a pharmaceutical composition comprising an antibody is a lyophilized powder, which can be reconstituted for administration as solutions, emulsions and other mixtures. It may also be reconstituted and formulated as solids or gels. The lyophilized powder is prepared by dissolving an antibody provided herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

An antibody can also, for example, be formulated in liposomes. Liposomes containing the molecule of interest are prepared by methods known in the art, such as described in Epstein et al. (1985) *Proc. Natl. Acad. Sci. USA* 82:3688; Hwang et al. (1980) *Proc. Natl. Acad. Sci. USA* 77:4030; and U.S. Pat. Nos. 4,485,045 and 4,544,545. Liposomes with enhanced circulation time are disclosed in U.S. Pat. No. 5,013,556. In one embodiment, liposomal suspensions may also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound comprising an antibody described herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

An antibody can also be entrapped in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* (1990) Mack Publishing Co., Easton, Pa.

Sustained-release preparations can also be prepared. Suitable examples of sustained-release preparations include semipermeable matrices of solid hydrophobic polymers containing the antagonist, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The antibodies and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

The compositions to be used for in vivo administration can be sterile. This is readily accomplished by filtration through, e.g., sterile filtration membranes.

In a specific embodiment, nucleic acids comprising sequences encoding an antibody are administered to a subject by way of gene therapy. Gene therapy refers to therapy performed by the administration to a subject of an expressed or expressible nucleic acid. Encompassed herein are any of the methods for gene therapy available in the art. For general review of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

5.5 Prophylactic and Therapeutic Uses

In one aspect, provided herein are methods of preventing, managing, and/or treating an influenza virus disease in a subject by administering an antibody described herein or an antigen-binding fragment thereof. In a specific embodiment, a method for preventing, managing and/or treating an influenza virus disease in a subject comprises administering to a subject an effective amount of an antibody described herein or an antigen-binding fragment thereof, or a composition thereof. In another embodiment, a method for preventing, managing, and/or treating an influenza virus disease in a subject comprises administering to a subject an effective amount of an antibody described herein or an antigen-binding fragment thereof, or a composition thereof and another therapy. In particular embodiments, the antibody is a monoclonal antibody. In a specific embodiment, the influenza virus disease that is prevented, managed, and/or treated is caused by an influenza virus that is characterized as a Group 1 influenza virus. In another specific embodiment, the influenza virus disease that is prevented, managed, and/or treated is caused by an influenza virus that is characterized as an influenza virus of the H1 subtype. In another specific embodiment, the influenza virus disease that is prevented, managed, and/or treated is caused by an influenza virus that is characterized as an influenza virus of the H5 subtype.

In one aspect, provided herein are methods of preventing and/or treating an influenza virus infection in a subject by administering an antibody described herein or an antigen-binding fragment thereof. In a specific embodiment, a method for preventing and/or treating an influenza virus infection in a subject comprises administering to a subject an effective amount of an antibody described herein or an antigen-binding fragment thereof, or a composition thereof. In another embodiment, a method for preventing and/or treating an influenza virus infection in a subject comprises administering to a subject an effective amount of an antibody described herein or an antigen-binding fragment thereof, or composition thereof and another therapy. In particular embodiments, the antibody is a monoclonal antibody. In a specific embodiment, the influenza virus infection that is prevented and/or treated is caused by an influenza virus that is characterized as a Group 1 influenza virus. In another specific embodiment, the influenza virus infection that is prevented and/or treated is caused by an influenza virus that is characterized as an influenza virus of the H1 subtype. In another specific embodiment, the influenza virus infection that is prevented and/or treated is caused by an influenza virus that is characterized as an influenza virus of the H5 subtype.

In a specific embodiment, administration of an antibody(ies) prevents or inhibits influenza virus from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to influenza virus binding to its host cell receptor in the absence of said antibody(ies) or in the presence of a negative control in an assay known to one of skill in the art or described herein.

In a specific embodiment, administration of an antibody (ies) prevents or inhibits influenza virus-induced fusion by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to influenza virus-induced fusion in the absence of said antibody(ies) or in the presence of a negative control in an assay known to one of skill in the art or described herein.

In a specific embodiment, administration of an antibody(ies) prevents or inhibits influenza virus-induced fusion after viral attachment to cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to influenza virus-induced fusion after viral attachment to cells in the absence of said antibody(ies) or in the presence of a negative control in an assay known to one of skill in the art or described herein.

In a specific embodiment, administration of an antibody(ies) inhibits or reduces influenza virus replication by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to replication of influenza virus in the absence of said antibody(ies) or in the presence of a negative control in an assay known to one of skill in the art or described herein. Inhibition of influenza virus replication can be determined by detecting the influenza virus titer in a biological specimens from a subject using methods known in the art (e.g., Northern blot analysis, RT-PCR, Western Blot analysis, etc.).

In a specific embodiment, administration of an antibody(ies) results in reduction of about 1-fold, about 1.5-fold, about 2-fold, about 3-fold, about 4-fold, about 5-fold, about 8-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, about 105 fold, about 110-fold, about 115-fold, about 120 fold, about 125-fold or higher in influenza virus titer in the subject. The fold-reduction in influenza virus titer may be as compared to a negative control, as compared to another treatment, or as compared to the titer in the patient prior to antibody administration.

In a specific embodiment, administration of an antibody(ies) results in a reduction of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 5 logs, 2 to 10 logs, 2 to 5 logs, or 2 to 10 logs in influenza virus titer in the subject. The log-reduction in influenza virus titer may be as compared to a negative control, as compared to another treatment, or as compared to the titer in the patient prior to antibody administration.

In a specific embodiment, administration of an antibody(ies) inhibits or reduces influenza virus infection of a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to influenza virus infection of a subject in the absence of said antibody(ies) or in the presence of a negative control in an assay known to one of skill in the art or described herein.

In a specific embodiment, administration of an antibody(ies) inhibits or reduces the spread of influenza virus in a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the spread of influenza virus in a subject in the absence of said an antibody(ies) or in the presence of a negative control in an assay known to one of skill in the art or described herein.

In a specific embodiment, administration of an antibody(ies) inhibits or reduces the spread of influenza virus between a subject and at least one other subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the spread of influenza virus between a subject and at least one other subject in the absence of said antibody(ies) or in the presence of a negative control in an assay known to one of skill in the art or described herein.

In a specific embodiment, administration of an antibody(ies) or an antigen-binding fragment thereof to a subject reduces the number of and/or the frequency of symptoms of influenza virus disease or infection in the subject (exemplary symptoms of influenza virus disease include, but are not limited to, body aches (especially joints and throat), fever, nausea, headaches, irritated eyes, fatigue, sore throat, reddened eyes or skin, and abdominal pain).

An antibody(ies) or an antigen-binding fragment thereof may be administered alone or in combination with another/ other type of therapy known in the art to reduce influenza virus infection, to reduce titers of influenza virus in a subject, to reduce the spread of influenza virus between subjects, to inhibit influenza virus replication, to inhibit influenza virus-induced fusion, and/or to inhibit binding of influenza virus to its host cell receptor.

One or more of the antibodies (or antigen-binding fragments thereof) may be used locally or systemically in the body as a prophylactic or therapeutic agent. The antibodies (or antigen-binding fragments thereof) may also be advantageously utilized in combination with other antibodies (e.g., monoclonal or chimeric antibodies), or with lymphokines or hematopoietic growth factors (such as, e.g., IL-2, IL-3 and IL-7), which, for example, serve to increase the number or activity of effector cells which interact with the antibodies.

One or more antibodies (or antigen-binding fragments thereof) may also be advantageously utilized in combination with one or more agents used to treat influenza virus infection such as, for example anti-viral agents. Specific anti-viral agents include: oseltamavir (Tamiflu®), zanamivir (Relenza®), nucleoside analogs (e.g., zidovudine, acyclovir, gangcyclovir, vidarabine, idoxuridine, trifluridine, and ribavirin), foscarnet, amantadine, rimantadine (Flumadine®), saquinavir, indinavir, ritonavir, alpha-interferons and other interferons, AZT, influenza virus vaccines (e.g., Fluarix®, FluMist®, Fluvirin®, and Fluzone®).

In some embodiments, an antibody (or an antigen-binding fragment thereof) acts synergistically with the one or more other therapies. Generally, administration of products of a species origin or species reactivity (in the case of antibodies) that is the same species as that of the patient is preferred. Thus, in a preferred embodiment, human or humanized antibodies are administered to a human patient for treatment or prophylaxis of an influenza virus infection or a disease associated therewith.

In one embodiment, provided herein are methods of prevention, management, treatment and/or amelioration of an influenza virus disease, and/or a symptom relating thereto as alternatives to current therapies. In a specific embodiment, the current therapy has proven or may prove to be too toxic (i.e., results in unacceptable or unbearable side effects) for the patient. In another embodiment, an antibody described herein or an antigen-binding fragment thereof decreases the side effects as compared to the current therapy. In another embodiment, the patient has proven refractory to a current therapy. In such embodiments, encompassed herein is the administration of one or more antibodies described herein (or an antigen-binding fragments thereof) without any other anti-infection therapies.

Suitable regimens can be selected by one skilled in the art by considering such factors and by following, for example, dosages reported in the literature and recommended in the Physician's Desk Reference ($58^{th}$ ee., 2004). See Section 5.5.2 for exemplary dosage amounts and frequencies of administration of the monoclonal antibodies described herein (or an antigen-binding fragment thereof).

In accordance with the methods encompassed herein, an antibody described herein (or an antigen-binding fragment thereof) may be used as any line of therapy, including, but not limited to, a first, second, third, fourth and/or fifth line of therapy. Further, in accordance with the methods encompassed herein, an antibody described herein (or an antigen-binding fragment thereof) can be used before or after any adverse effects or intolerance of the therapies other than an antibody described herein (or an antigen-binding fragment thereof) occurs. Encompassed herein are methods for administering one or more antibodies described herein (or an antigen-binding fragments thereof) to prevent the onset of an influenza virus disease and/or to treat or lessen the recurrence of an influenza virus disease.

In a specific embodiment, administration of an antibody(ies) or an antigen-binding fragment thereof to a subject reduces the incidence of hospitalization by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the incidence of hospitalization in the absence of administration of said antibody(ies) or antigen-binding fragment thereof.

In a specific embodiment, administration of an antibody(ies) or an antigen-binding fragment thereof to a subject reduces mortality by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the mortality in the absence of administration of said antibody(ies).

Further encompassed herein are methods for preventing, managing, and/or treating an influenza virus disease and/or a symptom relating thereto for which no other anti-viral therapy is available.

5.5.1 Patient Population

In one embodiment, a patient treated or prevented in accordance with the methods provided herein is a naïve subject, i.e., a subject that does not have a disease caused by influenza virus infection or has not been and is not currently infected with an influenza virus infection. In another embodiment, a patient treated or prevented in accordance with the methods provided herein is a subject that is at risk of acquiring an influenza virus infection. In another embodiment, a patient treated or prevented in accordance with the methods provided herein is a naïve subject that is at risk of acquiring an influenza virus infection. In another embodiment, a patient treated or prevented in accordance with the methods provided herein is a patient suffering from or expected to suffer from an influenza virus disease. In another embodiment, a patient treated or prevented in accordance with the methods provided herein is a patient diagnosed with an influenza virus infection or a disease associated therewith. In some embodiments, a patient treated or prevented in accordance with the methods provided herein is a patient infected with an influenza virus that does not manifest any symptoms of influenza virus disease.

In a specific embodiment, a patient treated or prevented in accordance with the methods provided herein is a subject that is at risk of an infection with a Group 1 influenza virus (e.g., an influenza A virus strain of the H1 or H5 subtype). In another specific embodiment, a patient treated or prevented in accordance with the methods provided herein is a naïve subject that is at risk of an infection with a Group 1 influenza virus (e.g., an influenza A virus strain of the H1 or H5 subtype). In another specific embodiment, a patient treated or prevented in accordance with the methods provided herein is a patient suffering from or expected to suffer from an influenza virus disease caused by a Group 1 influenza virus (e.g., an influenza A virus strain of the H1 or H5 subtype). In another specific embodiment, a patient treated or prevented in accordance with the methods provided herein is a patient diagnosed with a Group 1 influenza virus (e.g., an influenza A virus strain of the H1 or H5 subtype) infection or a disease associated therewith.

In another embodiment, a patient treated or prevented in accordance with the methods provided herein is a patient experiencing one or more symptoms of influenza virus disease. Symptoms of influenza virus disease include, but are not limited to, body aches (especially joints and throat), fever, nausea, headaches, irritated eyes, fatigue, sore throat, reddened eyes or skin, and abdominal pain. In another embodiment, a patient treated or prevented in accordance with the methods provided herein is a patient with influenza virus disease who does not manifest symptoms of the disease that are severe enough to require hospitalization.

In another embodiment, a patient treated or prevented in accordance with the methods provided herein is a patient infected with an influenza A virus, an influenza B virus or influenza C virus. In another embodiment, a patient treated or prevented in accordance with the methods provided herein is a patient infected with a particular subtype of influenza A virus. In another embodiment, a patient treated or prevented in accordance with the methods provided herein is a patient infected with a Group 1 influenza virus (e.g., an influenza A virus strain of the H1 or H5 subtype). In another embodiment, a patient treated or prevented in accordance with the methods provided herein is a patient infected with an influenza virus characterized as an influenza virus of the H1 subtype or H5 subtype. In accordance with such embodiments, the patients that are infected with the virus may manifest symptoms of influenza virus disease.

In some embodiments, a patient treated or prevented in accordance with the methods provided herein is an animal. In certain embodiments, the animal is a bird. In certain embodiments, the animal is a mammal, e.g., a horse, swine, mouse, or primate, preferably a human.

In a specific embodiment, a patient treated or prevented in accordance with the methods provided herein is a human. In certain embodiments, a patient treated or prevented in accordance with the methods provided herein is a human infant. In some embodiments, a patient treated or prevented in accordance with the methods provided herein is a human toddler. In certain embodiments, a patient treated or prevented in accordance with the methods provided herein is a human child. In other embodiments, a patient treated or prevented in accordance with the methods provided herein is a human adult. In some embodiments, a patient treated or prevented in accordance with the methods provided herein is an elderly human.

In certain embodiments, a patient treated or prevented in accordance with the methods provided herein is patient that is pregnant. In another embodiment, a patient treated or prevented in accordance with the methods provided herein is a patient who may or will be pregnant during the influenza season (e.g., November to April in the Northern Hemisphere).

In some embodiments, a patient treated or prevented in accordance with the methods provided herein is any subject at increased risk of influenza virus infection or disease resulting from influenza virus infection (e.g., an immunocompromised or immunodeficient individual). In some embodiments, a patient treated or prevented in accordance with the methods provided herein is any subject in close contact with an individual with increased risk of influenza virus infection or disease resulting from influenza virus infection (e.g., immunocompromised or immunosuppressed individuals).

In some embodiments, a patient treated or prevented in accordance with the methods provided herein is a subject affected by any condition that increases susceptibility to influenza virus infection or complications or disease resulting from influenza virus infection. In other embodiments, a patient treated or prevented in accordance with the methods provided herein is a subject in which an influenza virus infection has the potential to increase complications of another condition that the individual is affected by, or for which they are at risk. In particular embodiments, such conditions that increase susceptibility to influenza virus complications or for which influenza virus increases complications associated with the condition are, e.g., conditions that affect the lung, such as cystic fibrosis, asthma, chronic obstructive pulmonary disease, emphysema, or bacterial infections; cardiovascular disease; or diabetes. Other conditions that may increase influenza virus complications include kidney disorders; blood disorders (including anemia or sickle cell disease); or weakened immune systems (including immunosuppression caused by medications, malignancies such as cancer, organ transplant, or HIV infection).

In some embodiments, a patient treated or prevented in accordance with the methods provided herein is a subject that resides in a group home, such as a nursing home or orphanage. In some embodiments, a patient treated or prevented in accordance with the methods provided herein is subject that works in, or spends a significant amount of time in, a group home, e.g., a nursing home or orphanage. In some embodiments, a patient treated or prevented in accordance with the methods provided herein is a health care worker (e.g., a doctor or nurse). In some embodiments, a patient treated or prevented in accordance with the methods provided herein resides in a dormitory (e.g., a college dormitory). In some embodiments, a patient treated or prevented in accordance with the methods provided herein is a member of the military. In some embodiments, a patient treated or prevented in accordance with the methods provided herein is a child that attends school or daycare.

In some embodiments, a patient treated or prevented in accordance with the methods provided herein is a subject at increased risk of developing complications from influenza virus infection including: any individual who can transmit influenza viruses to those at high risk for complications, such as, e.g., members of households with high-risk individuals, including households that will include infants younger than 6 months, individuals coming into contact with infants less than 6 months of age, or individuals who will come into contact with individuals who live in nursing homes or other long-term care facilities; individuals with long-term disorders of the lungs, heart, or circulation; individuals with metabolic diseases (e.g., diabetes); individuals with kidney disorders; individuals with blood disorders (including anemia or sickle cell disease); individuals with weakened immune systems (including immunosuppression caused by medications, malignancies such as cancer, organ transplant, or HIV infection); children who receive long-term aspirin therapy (and therefore have a higher chance of developing Reye syndrome if infected with influenza).

In other embodiments, a patient treated or prevented in accordance with the methods provided herein includes healthy individuals six months of age or older, who: plan to travel to foreign countries and areas where flu outbreaks may be occurring, such, e.g., as the tropics and the Southern Hemisphere from April through September; travel as a part of large organized tourist groups that may include persons from areas of the world where influenza viruses are circulating; attend school or college and reside in dormitories, or reside in institutional settings; or wish to reduce their risk of becoming ill with influenza virus disease.

In specific embodiments, a patient treated or prevented in accordance with the methods provided herein is an individual who is susceptible to adverse reactions to conventional therapies. In other embodiments, the patient may be a person who has proven refractory to therapies other than an antibody described herein (or an antigen-binding fragment thereof) but are no longer on these therapies. In certain embodiments, a patient with an influenza virus disease is refractory to a therapy when the infection has not significantly been eradicated and/or the symptoms have not been significantly alleviated. The determination of whether a patient is refractory can be made either in vivo or in vitro by any method known in the art for assaying the effectiveness of a therapy for infections, using art-accepted meanings of "refractory" in such a context. In various embodiments, a patient with an influenza virus disease is refractory when viral replication has not decreased or has increased following therapy.

In certain embodiments, patients treated or prevented in accordance with the methods provided herein are patients already being treated with antibiotics, anti-virals, anti-fungals, or other biological therapy/immunotherapy. Among these patients are refractory patients, patients who are too young for conventional therapies, and patients with reoccurring influenza virus disease or a symptom relating thereto despite treatment with existing therapies.

5.5.2 Route of Administration and Dosage

An antibody (or an antigen-binding fragment thereof) or composition described herein may be delivered to a subject by a variety of routes. These include, but are not limited to, intranasal, intratracheal, oral, intradermal, intramuscular, intraperitoneal, transdermal, intravenous, conjunctival and subcutaneous routes. Pulmonary administration can also be employed, e.g., by use of an inhaler or nebulizer, and formulation with an aerosolizing agent for use as a spray.

The amount of an antibody (or an antigen-binding fragment thereof) or composition which will be effective in the treatment and/or prevention of an influenza virus infection or an influenza virus disease will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, other medications administered, and whether treatment is prophylactic or therapeutic. Usually, the patient is a human but non-human mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

For passive immunization with an antibody (or an antigen-binding fragment thereof), the dosage ranges from about 0.0001 to 100 mg/kg, and more usually 0.01 to 5 mg/kg, of the patient body weight. For example, dosages can be 1 mg/kg body weight, 10 mg/kg body weight, or within the range of 1-10 mg/kg or in other words, 70 mg or 700 mg or within the range of 70-700 mg, respectively, for a 70 kg patient. In some embodiments, the dosage administered to the patient is about 3 mg/kg to about 60 mg/kg of the patient's body weight. Preferably, the dosage administered to a patient is between 0.025 mg/kg and 20 mg/kg of the patient's body weight, more preferably 1 mg/kg to 15 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of the antibodies described herein (or an antigen-binding fragment thereof) may be reduced by enhancing uptake and tissue penetration (e.g., into the nasal passages and/or lung) of the antibodies by modifications such as, for example, lipidation.

An exemplary treatment regime entails administration once per every two weeks or once a month or once every 3 to 6 months for a period of one year or over several years, or over several year-intervals. In some methods, two or more antibodies with different binding specificities are administered simultaneously to a subject. An antibody is usually administered on multiple occasions. Intervals between single dosages can be weekly, monthly, every 3 months, every 6 months or yearly. Intervals can also be irregular as indicated by measuring blood levels of antibody to the influenza virus antigen (e.g., hemagglutinin) in the patient.

In a specific embodiment, an antibody described herein (or an antigen-binding fragment thereof), or a composition thereof is administered once a month just prior to (e.g., within three months, within two months, within one month) or during the influenza season. In another embodiment, an antibody described herein (or an antigen-binding fragment thereof), or a composition thereof is administered every two months just prior to or during the influenza season. In another embodiment, an antibody described herein (or an antigen-binding fragment thereof), or a composition thereof is administered every three months just prior to or during the influenza season. In a specific embodiment, an antibody described herein (or an antigen-binding fragment thereof), or a composition thereof is administered once just prior to or during the influenza season. In another specific embodiment, an antibody described herein (or an antigen-binding fragment thereof), or a composition thereof is administered twice, and most preferably once, during a influenza season. In some embodiments, an antibody described herein (or an antigen-binding fragment thereof), or a composition thereof is administered just prior to the influenza season and can optionally be administered once during the influenza season. In some embodiments, an antibody described herein (or an antigen-binding fragment thereof), or a composition thereof is administered every 24 hours for at least three days, at least four days, at least five days, at least six days up to one week just prior to or during an influenza season. In specific embodiments, the daily administration of the antibody or composition thereof occurs soon after influenza virus infection is first recognized in a patient, but prior to presentation of clinically significant disease. The term "influenza season" refers to the season when influenza infection is most likely to occur. Typically, the influenza season in the northern hemisphere commences in November and lasts through April.

In some embodiments, the plasma level of an antibody described herein (or an antigen-binding fragment thereof) in a patient is measured prior to administration of a subsequent dose of an antibody described herein (or an antigen-binding fragment thereof), or a composition thereof. The plasma level of the antibody may be considered in determining the eligibility of a patient to receive a subsequent dose of an antibody described herein (or an antigen-binding fragment thereof). For example, a patient's plasma level of an antibody described herein (or an antigen-binding fragment thereof) may suggest not administering an antibody described herein (or an antigen-binding fragment thereof); alternatively, a patient's plasma level of an antibody described herein (or an antigen-binding fragment thereof) may suggest administering an antibody described herein (or an antigen-binding fragment thereof) at a particular dosage, at a particular frequency, and/or for a certain period of time.

In certain embodiments, the route of administration for a dose of an antibody described herein (or an antigen-binding fragment thereof), or a composition thereof to a patient is intranasal, intramuscular, intravenous, or a combination thereof, but other routes described herein are also acceptable. Each dose may or may not be administered by an identical route of administration. In some embodiments, an antibody described herein (or an antigen-binding fragment thereof), or composition thereof, may be administered via multiple routes of administration simultaneously or subsequently to other doses of the same or a different antibody described herein (or an antigen-binding fragment thereof).

5.5.3 Combination Therapies

In various embodiments, an antibody described herein (or an antigen-binding fragment thereof) or a nucleic acid encoding such an antibody may be administered to a subject in combination with one or more other therapies (e.g., antiviral or immunomodulatory therapies). In some embodiments, a pharmaceutical composition described herein may be administered to a subject in combination with one or more therapies. The one or more other therapies may be beneficial in the treatment or prevention of an influenza virus disease or may ameliorate a condition associated with an influenza virus disease. The one or more other therapies may be beneficial in the treatment or prevention of an influenza virus infection or a disease associated therewith.

In some embodiments, the one or more other therapies that are supportive measures, such as pain relievers, anti-fever medications, or therapies that alleviate or assist with breathing. Specific examples of supportive measures include humidification of the air by an ultrasonic nebulizer, aerolized racemic epinephrine, oral dexamethasone, intravenous fluids, intubation, fever reducers (e.g., ibuprofen, acetometaphin), and antibiotic and/or anti-fungal therapy (i.e., to prevent or treat secondary bacterial and/or fungal infections).

In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patent visit. The two or more therapies can be administered in the same composition or a different composition. Further, the two or more therapies can be administered by the same route of administration of a different route of administration.

Any anti-viral agents well-known to one of skill in the art may be used in combination with an antibody or pharmaceutical composition described herein. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, AZT, zanamivir, and oseltamivir. Other anti-viral agents include influenza virus vaccines, e.g., Fluarix® (GlaxoSmithKline), FluMist® (MedImmune Vaccines), Fluvirin® (Chiron Corporation), Fluzone® (Aventis Pasteur), or those described in Section 5.6 infra.

In specific embodiments, the anti-viral agent is an immunomodulatory agent that is specific for a viral antigen. In particular embodiments, the viral antigen is an influenza virus polypeptide other than a hemagglutinin polypeptide. In other embodiments, the viral antigen is an influenza virus hemagglutinin polypeptide.

In a specific embodiment, one or more therapies that prevent or treat secondary responses to a primary influenza virus infection are administered in combination with one or more antibodies described herein (or an antigen-binding fragment thereof). Examples of secondary responses to a primary influenza virus infection include, but are not limited to, asthma-like responsiveness to mucosal stimuli, elevated total respiratory resistance, increased susceptibility to secondary viral, bacterial, and fungal infections, and development of conditions such as, but not limited to, bronchiolitis, pneumonia, croup, and febrile bronchitis.

In a specific embodiment, one or more antibodies described herein (or antigen-binding fragment thereof) is used in combination with another antibody that binds to an influenza virus Group 1 HA to prevent and/or treat an influenza virus infection and/or influenza virus disease. In another specific embodiment, one or more antibodies described herein (or antigen-binding fragment thereof) is used in combination with an antibody that binds to an influenza virus Group 2 HA to prevent and/or treat an influenza virus infection and/or influenza virus disease. In another specific embodiment, one or more antibodies described herein (or antigen-binding fragment thereof) is used in combination with an antibody that binds to an influenza virus neuraminidase to prevent and/or treat an influenza virus infection and/or influenza virus disease. In another specific embodiment, one or more antibodies described herein (or antigen-binding fragment thereof) is used in combination with an antibody that binds to an influenza virus neuraminidase and an antibody that binds to an influenza virus Group 2 HA to prevent and/or treat an influenza virus infection and/or influenza virus disease.

In a specific embodiment, one or more antibodies described herein (or an antigen-binding fragment thereof) is used in combination with another antibody (e.g., an anti-influenza virus monoclonal antibody) or a set of other antibodies (e.g., a set of anti-influenza virus monoclonal antibodies) in order to enhance the prophylactic and/or therapeutic effect of the other antibody or set of other antibodies.

In some embodiments, a combination therapy comprises the administration of one or more antibodies described herein (or an antigen-binding fragment thereof). In some embodiments, a combination therapy comprises administration of two or more antibodies described herein (or an antigen-binding fragment thereof). In a specific embodiment, a combination therapy comprises the administration of the GG3 antibody and one or more other therapies.

5.6 Diagnostic Uses

The antibodies or antigen-binding fragments thereof described herein can be used for diagnostic purposes to detect an influenza virus as well as detect, diagnose, or monitor an influenza virus infection. In specific embodiments, the antibodies or antigen-binding fragments thereof can be used to determine whether a particular influenza virus is present or a particular influenza virus subtype is present in a biological specimen (e.g., sputum, nasal drippings, other fluids, cells, or tissue samples).

Provided herein are methods for the detection of an influenza virus infection comprising: (a) assaying the expression of an influenza virus HA in a biological specimen (e.g., sputum, nasal drippings, cells or tissue samples) from a subject using an antibody described herein (or an antigen-binding fragment thereof); and (b) comparing the level of the influenza virus HA with a control level, e.g., levels in a biological specimen from a subject not infected with influenza virus, wherein an increase in the assayed level of influenza virus antigen compared to the control level of the influenza virus HA is indicative of an influenza virus infection.

In a specific embodiment, the subtype of the influenza virus, e.g., the H1 or H5 subtype of influenza A virus, can be detected in accordance with the methods for detecting an influenza virus infection. According to this method, an antibody described herein (or an antigen-binding fragment thereof) that is used in the assay is specifically reactive to the subtype to be detected.

Provided herein is a diagnostic assay for diagnosing an influenza virus infection comprising: (a) assaying for the level of an influenza virus HA in a biological specimen from a subject using an antibody described herein (or an antigen-binding fragment thereof); and (b) comparing the level of the influenza virus HA with a control level, e.g., levels in a biological specimen from a subject not infected with influenza virus, wherein an increase in the assayed influenza virus HA level compared to the control level of the influenza virus HA is indicative of an influenza virus infection. A more definitive diagnosis of an influenza virus infection may allow health professionals to employ preventative measures or aggressive treatment earlier thereby preventing the development or further progression of the influenza virus infection.

Diagnosis of infection with a specific influenza virus subtype (by use of subtype-specific antibodies) may allow the prescription of anti-viral medications that are most appropriate for treatment of the particular subtype.

Antibodies or antigen-binding fragments thereof described herein can be used to assay influenza virus HA levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105: 3087-3096). Antibody-based methods useful for detecting protein expression include immunoassays, such as the enzyme linked immunosorbent assay (ELISA) and the radioimmunoassay (RIA). An antibody described herein or generated in accordance with the methods described herein may be labeled with a detectable label or a secondary antibody that binds to such an antibody may be labeled with a detectable label. Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$I) and technetium ($^{99}$Tc); luminescent labels, such as luminol; and fluorescent labels, such as fluorescein and rhodamine, and biotin.

Also provided herein is the detection and diagnosis of an influenza virus infection in a human. In one embodiment, diagnosis comprises: a) administering (for example, parenterally, intranasally, subcutaneously, or intraperitoneally) to a subject an effective amount of a labeled monoclonal antibody described herein (or an antigen-binding fragment thereof); b) waiting for a time interval following the administering for permitting the labeled antibody to preferentially concentrate at sites in the subject (e.g., the nasal passages, lungs, mouth and ears) where the influenza virus antigen is expressed (and for unbound labeled molecule to be cleared to background level); c) determining background level; and d) detecting the labeled antibody in the subject, such that detection of labeled antibody above the background level indicates that the subject has an influenza virus infection or a symptom relating thereto. Background level can be determined by various methods, including comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled antibody to preferentially concentrate at sites in the subject and for unbound labeled antibody to be cleared to background level is 6 to 48 hours, or 6 to 24 hours or 6 to 12 hours. In another embodiment the time interval following administration is 5 to 20 days or 5 to 10 days.

In one embodiment, monitoring of an influenza virus infection is carried out by repeating the method for diagnosing the influenza virus infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods provided herein include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

5.7 Biological Assays 5.7.1 Assays for Testing Antibody Activity

An antibody may be characterized in a variety of ways known to one of skill in the art (e.g., ELISA, surface plasmon resonance display (BIAcore kinetic), Western blot, immunofluorescence, immunostaining and/or microneutralization assays). In some embodiments, an antibody is assayed for its ability to bind to an influenza virus antigen (e.g., an hemagglutinin polypeptide), or an influenza virus.

The specificity or selectivity of an antibody for an influenza virus HA and cross-reactivity with other antigens can be assessed by any method known in the art. Immunoassays which can be used to analyze specific binding and cross-reactivity include, but are not limited to, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to an influenza virus HA and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody for an influenza virus antigen or an influenza virus and the binding off-rates can be determined from the data by Scatchard plot analysis. Competition with a second antibody can also be determined using radioimmunoassays. In this case, an influenza virus antigen or an influenza virus is incubated with the test antibody conjugated to a detectable labeled (e.g., $^3$H or $^{125}$I) in the presence of increasing amounts of an unlabeled second antibody.

In some embodiments, surface plasmon resonance (e.g., BIAcore kinetic) analysis is used to determine the binding on and off rates of an antibody to an influenza virus antigen (e.g., hemagglutinin polypeptide), or an influenza virus. BIAcore kinetic analysis comprises analyzing the binding and dissociation of influenza virus antigen from chips with immobilized antibodies to an influenza virus antigen on their surface. Briefly, a typical BIAcore kinetic study involves the injection of 250 μL of an antibody reagent (mAb, Fab) at varying concentration in HBS buffer containing 0.005% Tween-20 over a sensor chip surface, onto which has been immobilized the influenza virus hemagglutinin polypeptide. The flow rate is maintained constant at 75 μL/min. Dissociation data is collected for 15 min or longer as necessary. Following each injection/dissociation cycle, the bound antibody is removed from the influenza virus hemagglutinin polypeptide surface using brief, 1 min pulses of dilute acid, typically 10-100 mM HCl, though other regenerants are employed as the circumstances warrant. More specifically, for measurement of the rates of association, $k_{on}$, and dissociation, $k_{off}$, the polypeptide is directly immobilized onto the sensor chip surface through the use of standard amine coupling chemistries, namely the EDC/NHS method (EDC=N-diethylaminopropyl)-carbodiimide). Briefly, a 5-100 nM solution of the polypeptide in 10 mM NaOAc, pH 4 or pH 5 is prepared and passed over the EDC/NHS-activated surface until approximately 30-50 RU's worth of polypeptide are immobilized. Following this, the unreacted active esters are "capped" off with an injection of 1M Et-NH$_2$. A blank surface, containing no polypeptide, is prepared under identical immobilization conditions for reference purposes. Once an appropriate surface has been prepared, a suitable dilution series of each one of the antibody reagents is prepared in HBS/Tween-20, and passed over both the polypeptide and reference cell surfaces, which are connected in series. The range of antibody concentrations that are prepared varies, depending on what the equilibrium binding constant, $K_D$, is estimated to be. As described above, the bound antibody is removed after each injection/dissociation cycle using an appropriate regenerant.

The neutralizing activity of an antibody can be determined utilizing any assay known to one skilled in the art. Antibodies can be assayed for their ability to inhibit the binding of an influenza virus, or any other composition comprising influenza virus antigen, such as a hemagglutinin polypeptide (e.g., a virus-like particle (VLP), liposome, or detergent extract), to its host cell receptor (i.e., sialic acid) using techniques known to those of skill in the art. For example, cells expressing influenza virus receptors can be contacted with a composition comprising influenza virus HA in the presence or absence of the antibody and the ability of the antibody to inhibit the HA's binding can measured by, for example, flow cytometry or a scintillation assay. The composition comprising an influenza virus HA or the antibody can be labeled with a detectable compound such as a radioactive label (e.g., $^{32}$P, $^{35}$S, and $^{125}$I) or a fluorescent label (e.g., fluorescein isothiocyanate, rhodamine, phycoerythrin, phycocyanin, allophycocyanin, o-phthaldehyde and fluorescamine) to enable detection of an interaction between the composition comprising an influenza virus HA and a cell receptor. Alternatively, the ability of an antibody to inhibit an influenza virus HA from binding to its receptor can be determined in cell-free assays. For example, a composition comprising an influenza virus antigen (e.g., a hemagglutinin polypeptide) can be contacted with an antibody and the ability of the antibody to inhibit the composition comprising an influenza virus HA from binding to a cell receptor can be determined. In a specific embodiment, the antibody is immobilized on a solid support and the composition comprising an influenza virus HA is labeled with a detectable compound. Alternatively, a composition comprising an influenza virus antigen is immobilized on a solid support and the antibody is labeled with a detectable compound.

In a specific embodiment, the neutralizing activity of an antibody is assessed using a microneutralization assay. In another specific embodiment, the neutralizing activity of an antibody is assessed using a plaque reduction assay as such as described in Section 6, infra.

In other embodiments, an antibody suitable for use in a method described herein does not inhibit influenza virus receptor binding, yet is still found to be neutralizing in an assay described herein. In some embodiments, an antibody suitable for use in accordance with a method described herein reduces or inhibits virus-host membrane fusion in an assay known in the art or described herein.

In one embodiment, virus-host membrane fusion is assayed in an in vitro assay using an influenza virus containing a reporter and a host cell capable of being infected with the virus. An antibody inhibits fusion if reporter activity is inhibited or reduced compared to a negative control (e.g., reporter activity in the presence of a control antibody or in the absence of antibody).

In one embodiment, virus-host membrane fusion is detected using a model system of cell fusion. In an exemplary cell fusion assay, cells (e.g., HeLa cells) are transfected with a plasmid encoding an influenza virus hemagglutinin polypeptide and contacted and exposed to a buffer that allows the hemagglutinin polypeptide fusion function (e.g., pH 5.0 buffer) in the presence of an antibody. An antibody is neutralizing if it reduces or inhibits syncytia formation compared to a negative control (e.g., syncytia formation in the presence of a control antibody or in the absence of antibody).

In a specific embodiment, virus-host membrane fusion is assayed using a red blood cell fusion assay as known in the art or described herein.

In other embodiments, virus-host membrane fusion is assayed using an in vitro liposome-based assay. In an exemplary assay, the host cell receptor is reconstituted into liposomes containing one half of a reporter. influenza hemagglutinin polypeptide is reconstituted into another set of liposomes containing another half of a reporter. When the two liposome populations are mixed together, fusion is detected by reconstitution of the reporter, for example, an enzymatic reaction that can be detected colorimetrically. An antibody inhibits fusion if reporter activity is reduced or inhibited compared to reporter activity in an assay conducted in the absence of antibody or in the presence of a control antibody.

5.7.2 In Vitro Assays

An antibody or a composition thereof can be assessed in vitro for activity. In one embodiment, an antibody or composition thereof is tested in vitro for its effect on growth of an influenza virus. Growth of influenza virus can be assessed by any method known in the art or described herein (e.g. in cell culture). In a specific embodiment, cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented a monoclonal antibody described herein (or an antigen-binding fragment thereof) Viral titers are determined in the supernatant by hemagglutinin plaques or any other viral assay described herein. Cells in which viral titers can be assessed include, but are not limited to, MDCK cells, EFK-2 cells, Vero cells, primary human umbilical vein endothelial cells (HUVEC), H292 human epithelial cell line and HeLa cells. In vitro assays include those that measure altered viral replication (as determined, e.g., by plaque formation) or the production of viral proteins (as determined, e.g., by Western blot analysis) or viral RNAs (as determined, e.g., by RT-PCR or northern blot analysis) in cultured cells in vitro using methods which are well known in the art or described herein.

In one non-limiting example, a monolayer of the target mammalian cell line is infected with different amounts (e.g., multiplicity of 3 plaque forming units (pfu) or 5 pfu) of influenza virus and subsequently cultured at 37° C. in the presence or absence of various dilutions of a monoclonal antibody described herein (or an antigen-binding fragment thereof) (e.g., 0.1 µg/ml, 1 µg/ml, 5 µg/ml, or 10 µg/ml). Cultures are overlaid with agar and harvested 48 hours or 72 hours post infection and titered by standard plaque assays known in the art on the appropriate target cell line (e.g., MDCK cells).

In a non-limiting example of a hemagglutination assay, cells are contacted with an antibody and are concurrently or subsequently infected with the virus (e.g., at an MOI of 1) and the virus is incubated under conditions to permit virus replication (e.g., 20-24 hours). The antibody is preferably present throughout the course of infection. Viral replication and release of viral particles is then determined by hemagglutination assays using 0.5% chicken red blood cells. See, e.g., Kashyap et al., PNAS USA 105: 5986-5991. In some embodiments, an antibody or composition thereof is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more. In other specific embodiments, an inhibitor reduces viral titer in this assay by 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 5 logs, 2 to 10 logs, 2 to 5 logs, or 2 to 10 logs.

5.7.3 Cytotoxicity Assays

Many assays well-known in the art can be used to assess viability of cells (infected or uninfected) or cell lines following exposure to an antibody or composition thereof and, thus, determine the cytotoxicity of the antibody or composition thereof. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270: 18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes may be given a designation of T (100% toxic), PVH (partially toxic-very heavy-80%), PH (partially toxic-heavy-60%), P (partially toxic-40%), Ps (partially toxic-slight-20%), or 0 (no toxicity-0%), conforming to the degree of cytotoxicity seen. A 50% cell inhibitory (cytotoxic) concentration ($IC_{50}$) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. In certain embodiments, cytotoxicity is assessed in one or more of the following cell lines: MDCK, MEF, Huh 7.5, Detroit, or human tracheobronchial epithelial (HTBE) cells.

An antibody or composition thereof can be tested for in vivo toxicity in animal models. For example, animal models, described herein and/or others known in the art, used to test the activities of an antibody or composition thereof can also be used to determine the in vivo toxicity of these antibodies. For example, animals are administered a range of concentrations of an antibody. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of an antibody or composition thereof can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An antibody or composition thereof that exhibits large therapeutic indices is preferred. While an antibody or composition thereof that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of an antibody or composition thereof for use in humans. The dosage of such antibodies lies preferably within a range of circulating concentrations that include the $ED_{50}$ with little or no toxicity. The dosage may vary within this range depending upon the dosage form employed and the route of administration utilized. For an antibody or composition thereof used in a method described herein, the effective dose can be estimated initially from cell culture assays. A dose may be formulated in animal models to achieve a circulating plasma concentration range that includes the $IC_{50}$ (i.e., the concentration of the antibody that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided herein.

Further, any assays known to those skilled in the art can be used to evaluate the prophylactic and/or therapeutic utility of an antibody or composition thereof, for example, by measuring viral infection or a condition or symptoms associated therewith.

5.7.4 In Vivo Assays

Antibodies and compositions thereof are preferably assayed in vivo for the desired therapeutic or prophylactic activity prior to use in humans. For example, in vivo assays can be used to determine whether it is preferable to administer an antibody or composition thereof and/or another therapy. For example, to assess the use of an antibody or composition thereof to prevent an influenza virus disease, the antibody or composition can be administered before the animal is infected with influenza virus. Alternatively, or in addition, an antibody or composition thereof can be administered to the animal at the same time that the animal is infected with influenza virus. To assess the use of an antibody or composition thereof to treat an influenza virus infection or disease associated therewith, the antibody or composition may be administered after infecting the animal with influenza virus. In a specific embodiment, an antibody or composition thereof is administered to the animal more than one time.

Antibodies and compositions thereof can be tested for antiviral activity in animal model systems including, but are not limited to, rats, mice, chicken, cows, monkeys, pigs, goats, sheep, dogs, rabbits, guinea pigs, etc. In a specific embodiment, an antibody or composition thereof is tested in a mouse model system. Such model systems are widely used and well-known to the skilled artisan. Non-limiting examples of animal models for influenza virus are provided in this section.

In general, animals are infected with influenza virus and concurrently or subsequently treated with an antibody or composition thereof, or placebo. Alternatively, animals are treated with an antibody or composition thereof or placebo and subsequently infected with influenza virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for a time period (e.g., 20 minutes or 1 hour) at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of an antibody or composition thereof on the infectious disease process or pathogenicity of a given virus can also be determined using in vivo assays in which the titer of the virus in an infected subject administered an antibody or composition thereof, the length of survival of an infected subject administered an antibody or composition thereof, the immune response in an infected subject administered an antibody or composition thereof, the number, duration and/or severity of the symptoms in an infected subject administered an antibody or composition thereof, and/or the time period before onset of one or more symptoms in an infected subject administered an antibody or composition thereof, is assessed. Techniques known to one of skill in the art can be used to measure such effects.

Influenza virus animal models, such as ferret, mouse, guinea pig, and chicken, developed for use to test antiviral agents against influenza virus have been described. See, e.g., Sidwell et al., Antiviral Res., 2000, 48:1-16; Lowen A. C. et al. PNAS., 2006, 103: 9988-92; and McCauley et al., Antiviral Res., 1995, 27:179-186. For mouse models of influenza, non-limiting examples of parameters that can be used to assay antiviral activity of antibodies administered to the influenza-infected mice include pneumonia-associated death, serum al-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

In yet other assays, histopathologic evaluations are performed after infection of an animal model subject. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+(focal squamous metaplasia of the epithelial layer); 2+(diffuse squamous metaplasia of much of the epithelial layer, cilia may be evident focally); 2.5+(diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+(few infected cells); 1+(few infected cells, as widely separated individual cells); 1.5+(few infected cells, as widely separated singles and in small clusters); 2+(moderate numbers of infected cells, usually affecting clusters of adjacent cells in portions of the epithelial layer lining bronchioles, or in small sublobular foci in alveoli); 3+(numerous infected cells, affecting most of the epithelial layer in bronchioles, or widespread in large sublobular foci in alveoli).

In one example, the ability to induce lung lesions and cause infection in an animal model of virus infection is compared using wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

In one embodiment, virus is quantified in tissue samples. For example, tissue samples are homogenized in phosphate-buffered saline (PBS), and dilutions of clarified homogenates adsorbed for 1 h at 37° C. onto monolayers of cells (e.g., MDCK cells). Infected monolayers are then overlaid with a solution of minimal essential medium containing 0.1% bovine serum albumin (BSA), 0.01% DEAE-dextran, 0.1% NaHCO$_3$, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., MDCK cells) in 96-well plates are incubated with log dilutions of clarified tissue homogenates in media. Two to three days after inoculation, 0.05-ml aliquots from each well are assessed for viral growth by hemagglutination assay (HA assay).

In a specific embodiment, the ability of an antibody or composition thereof to treat an influenza virus infection or disease associated therewith is assessed by determining the ability of the antibody to confer passive immunity to an influenza virus disease in a subject. The ability of an antibody described herein (or an antigen-binding fragment thereof) to confer passive immunity to an influenza virus disease in a subject can be assessed using any methods known in the art or described herein (see, e.g., Section 6, infra).

5.7.5 Assays in Humans

In one embodiment, an antibody or composition thereof that modulates replication of an influenza virus is assessed in infected human subjects. In accordance with this embodiment, an antibody or composition thereof is administered to the human subject, and the effect of the antibody and/or composition on viral replication is determined by, e.g., analyzing the level of the virus or viral nucleic acids in a biological sample (e.g., serum or plasma). An antibody or composition thereof that alters virus replication can be identified by comparing the level of virus replication in a subject or group of subjects treated with a control antibody to that in a subject or group of subjects treated with an antibody or composition thereof. Alternatively, alterations in viral replication can be identified by comparing the level of the virus replication in a subject or group of subjects before and after the administration of an antibody or composition thereof. Techniques known to those of skill in the art can be used to obtain the biological sample and analyze the mRNA or protein expression.

In another embodiment, the effect of an antibody or composition thereof on the severity of one or more symptoms associated with an influenza virus infection/disease are assessed in an infected subject. In accordance with this embodiment, an antibody or composition thereof or a control antibody is administered to a human subject suffering from influenza virus infection and the effect of the antibody or composition on one or more symptoms of the virus infection is determined. An antibody or composition thereof that reduces one or more symptoms can be identified by comparing the subjects treated with a control antibody to the subjects treated with the antibody or composition. Techniques known to physicians familiar with infectious diseases can be used to determine whether an antibody or composition thereof reduces one or more symptoms associated with the influenza virus disease.

5.8 Kits

Provided herein is a pharmaceutical pack or kit comprising one or more containers filled with one or more of the ingredients of the pharmaceutical compositions described herein, such as one or more antibodies provided herein (or an antigen-binding fragment thereof) or one or more antibody conjugates described herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in the above methods. In one embodiment, a kit comprises an antibody described herein, preferably an isolated antibody, in one or more containers. In a specific embodiment, the kits encompassed herein contain an isolated influenza virus antigen that the antibodies encompassed herein react with (e.g., the antibody binds to the antigen) as a control. In a specific embodiment, the kits provided herein further comprise a control antibody which does not react with an influenza virus HA (e.g., the antibody does not bind to the influenza virus HA). In another specific embodiment, the kits provided herein contain a means for detecting the binding of an antibody to an influenza virus HA (e.g., the antibody may be conjugated to a detectable substrate such as a fluorescent compound, an enzymatic substrate, a radioactive compound, a luminescent compound, or another antibody that is conjugated to a detectable substrate (e.g., the antibody may be conjugated to a second antibody which recognizes/binds to the first antibody)). In certain embodiments, the kits comprise a second antibody which is labeled with a detectable substance and which binds to an antibody described herein. In specific embodiments, the kit may include a recombinantly produced or chemically synthesized influenza virus HA. The influenza virus HA provided in the kit may also be attached to a solid support. In a more specific embodiment the detecting means of the above described kit includes a solid support to which an influenza virus antigen is attached. Such a kit may also include a non-attached reporter-labeled antibody. In this embodiment, binding of the antibody to the influenza virus HA can be detected by binding of the said reporter-labeled antibody.

6. EXAMPLES

The following examples are offered by way of illustration, and not by way of limitation.

6.1. Cross-Reactivity of Antibody 6.1.1. Materials & Methods

Immunofluorescence. Madin-Darby kidney (MDCK) cells were infected at an MOI of 2 to 5 of A/USSR/92/77 (H1), A/Texas/36/91 (H1), A/New Caledonia/20/99 (H1), A/Brisbane/59/07 (H1), rA/California/04/09 (H1), A/Hong Kong/1/68 (H3) or rA/Vietnam/1203/04 (H5) for 16 to 18 hours in the absence of trypsin. The MDCK monolayer was then fixed with 0.5% paraformaldehyde for 30 minutes at room temperature (RT) and blocked with 5% non-fat milk/1×PBS for another 30 minutes at RT. mAbs GG3 and E10 were diluted to 5 µg/mL in 5% non-fat milk and incubated at RT for 2 hours. The monolayer was washed with 1×PBS thrice. A goat anti-mouse antibody labeled with alexa-fluor 488 (Invitrogen, Inc.) was used as a secondary antibody at a dilution of 1:1000 in 5% non-fat milk/1×PBS and incubated at RT for 1 hour. The monolayer was again washed thrice with 1×PBS and 50 µL of 1×PBS added back after the last wash. Reactivity of mAbs to respective sample was detected using a fluorescent microscope.

Enzyme-linked immunosorbent assay (ELISA). Fifty microliters of purified preparations of baculovirus-expressed hemagglutinins for A/Solomon Islands/06 (H1), A/California/04/09 (H1) or A/Vietnam/1203/04 (H5) (at 2.5 µg/ml) were used to coat Costar 96-well enzyme immunoassay/radioimmunoassay (EIA/RIA) high-binding plates (Corning Inc.) overnight at 4° C. The next day, plates were washed twice with 0.1% Tween 20-1×PBS (TPBS) and blocked with 5% NF milk-1×PBS for 30 minutes at RT. Starting dilutions of GG3 was at 100 µg/ml and incubated at RT for 2 hours. After the incubation, plates were washed thrice with TPBS, then incubated with a 1:5,000 dilution of a goat anti-mouse IgG γ-chain-specific antibody conjugated to HRP (Millipore), and incubated at 37° C. for 1 hour. Plates were then washed thrice with TPBS and developed with 200 µl of Sigmafast OPD peroxidase substrate (Sigma-Aldrich) for 15 to 30 min in the dark. The signal was read at an absorbance of 405 nm. All MAb and secondary antibodies were diluted in 1% bovine serum albumin (BSA)-1×PBS. A nonlinear regression curve was generated using GraphPad Prism 4.0.

Plaque reduction neutralization assay (PRNA). Dilutions of MAb were first preincubated with 60 to 80 PFU of virus (either PR8, A/Texas/36/91 (H1), A/New Caledonia/20/99 (H1), FM47 (H1), rA/California/04/09 (H1), or rANietnam/1203/04 (H5)) for 1 hour at RT on a shaker. The virus and MAb mixture was then used to infect a monolayer of MDCK cells in duplicate in a 6-well format and incubated at 37° C. for 1 hour with intermittent rocking every 10 min. The agar overlay was supplemented with corresponding MAb dilutions. At 2 days post-infection (dpi), the monolayer was fixed with 4% PFA-1×PBS for 30 min and then permeabilized with 0.5% Triton X-100 for 20 min. Cells were blocked with 5% NF milk-1×PBS for 30 min at RT and were incubated accordingly with either infected sera (1:500) or PR8 nucleoprotein-specific MAb HT103 (5 µg/ml) (21) for 1 hour at RT. An anti-mouse secondary antibody conjugated to HRP was used at a 1:1,000 dilution. Plaques were visualized using TrueBlue peroxidase substrate (KPL Inc.), and the reaction was stopped with tap water. Plaques were counted for each antibody, and the percent inhibition was calculated versus the no-MAb group value. A nonlinear regression curve was generated using GraphPad Prism 4.0, and the 50% inhibitory concentration ($IC_{50}$) was calculated using the regression curve. An anti-glutathione S-transferase (GST) MAb, 22A6 (Mount Sinai School of Medicine), with an isotype of IgG2b, was employed as an isotype MAb control and used in parallel to all the neutralization assays for each virus with no observed dose-dependent inhibition.

Animal Studies. Six- to 8-week-old female BALB/c mice (Jackson Laboratories, Inc.) were treated intraperitoneally (5 mice per group) with 15, 7.5, 3.0, 1.0 mg/kg of body weight of Mab GG3 or 200 µL mg/kg of 1×PBS for 2 h before an intranasal infection with 5 50% mouse lethal doses ($mLD_{50}$) of the following viruses: A/Netherlands/602/2009 (NL09) (H1) or rA/Vietnam/1203/04 (rVN04) (H5). All mice were monitored daily, and their weights were recorded until the end of the 2-week experiment. Death was determined by a 31.5% body weight loss cutoff was used for NL09. The latter cutoff weight was used with permission from the Institutional Animal Care and Use Committee (IACUC).

6.1.2. Results

The monoclonal antibody GG3 demonstrated broad reactivity by immunofluorescence against cells infected with influenza A virus strains of the H1 subtype and cells infected with an influenza A virus strain of the H5 subtype (FIG. 3). The monoclonal antibody GG3 demonstrated broad reactivity against cells infected with influenza A virus strains of the H1 subtype that are antigenically distinct from one another. However, the monoclonal antaibody GG3 did not demonstrate reactivity against cells infected with an influenza A virus strain of the H3 subtype, namely A/Hong Kong/1/68 (FIG. 3). The control antibody (E10), which is specific for the influenza virus M2 protein, demonstrated reactivity against cells infected with influenza A virus strains of either the H1, H3 or H5 subtype (FIG. 3).

The results in FIG. 4 demonstrate that the monoclonal antibody GG3 is able to bind to hemagglutinin from different influenza A virus strains of the H1 subtype and hemagglutinin from an influenza A virus strain of the H5 subtype. Based upon the ELISA data, a lower concentration of the monoclonal antibody GG3 is able to bind to hemagglutinin from influenza A virus strains of the H1 subtype than hemagglutinin from an influenza A virus strain of the H5 subtype (FIG. 4).

The neutralization activity of the monoclonal antibody GG3 by plaque reduction assay was evaluated. The monoclonal antibody GG3 was able to prevent infection of Madin Darby canine kidney (MDCK) cells by influenza A virus strains of the H1 subtype (FIG. 5). In addition, the monoclonal antibody GG3 was able to prevent infection of MDCK cells by an influenza A virus strain of the H5 subtype (FIG. 5).

The ability of the monoclonal antibody GG3 to confer passive immunity was determined by assessing the ability of the antibody to prolong the survival of mice infected with an influenza virus. As demonstrated in FIG. 6B, 100% of the female BALB/c mice administered 15 mg/kg, 7.5 mg/kg, 3 mg/kg, or 1 mg/kg of the monoclonal antibody GG3 by intraperitoneal injection 2 hours prior to intranasal challenge with an influenza A virus strain of the H1 subtype survive fourteen days after viral challenge, whereas mice administered PBS alone die ten days after viral challenge. In addition, mice administered 15 mg/kg, 7.5 mg/kg, or 3 mg/kg of the monoclonal antibody GG3 intraperitoneally prior to intranasal challenge with an influenza A virus strain of the H1 subtype (namely, A/Netherlands/602/2009) maintained their weight fourteen days after viral challenge (FIG. 6A). Mice administered 1 mg/kg of the monoclonal antibody GG3 intraperitoneally prior to intranasal challenge with an influenza A virus strain of the H1 subtype exhibited a slight decrease in weight between 6 and 13 days after viral challenge (FIG. 6A). In contrast, mice administered PBS alone had a dramatic loss in weight over a period of 9 days after viral challenge before they died (FIG. 6A).

As demonstrated in FIG. 7B, 100% of the female BALB/c mice administered 15 mg/kg, 7.5 mg/kg or 3 mg/kg of the monoclonal antibody GG3 by intraperitoneal injection 2 hours prior to intranasal challenge with an influenza A virus strain of the H5 subtype survive fourteen days after viral challenge, whereas mice administered PBS alone die ten days after viral challenge. Sixty percent of the female BALB/c mice administered 1 mg/kg of the monoclonal antibody GG3 by intraperitoneal injection 2 hours prior to intranasal challenge with an influenza A virus of the H5 subtype survive fourteen days after viral challenge (FIG. 7B). In addition, mice administered 15 mg/kg or 7.5 mg/kg of the monoclonal antibody GG3 intraperitoneally prior to intranasal challenge with an influenza A virus strain of the H5 subtype (namely, rA/Vietnam/1203/04) maintained their weight over a period of 14 days after viral challenge (FIG. 7A). Mice administered 3 mg/kg or 1 mg/kg of the monoclonal antibody GG3 intraperitoneally prior to intranasal challenge with an influenza A virus strain of the H1 subtype exhibited a decrease in weight between 3 and 14 days after viral challenge (FIG. 7A). In contrast, mice administered PBS alone had a dramatic loss in weight over a period of 9 days after viral challenge before they died (FIG. 7A).

The data provided herein demonstrates that the monoclonal antibody GG3 cross-reacts with hemagglutinin from influenza A virus strains of the H1 subtype that are antigenically distinct from one another and an influenza A virus strain of the H5 subtype. In addition, the monoclonal antibody GG3 is capable of neutralizing all of the influenza A virus strains of the H1 subtype tested and the influenza A virus strain of the H5 subtype tested as determined by multiple assays. Moreover, the monoclonal antibody GG3 protects mice from intranasal challenge with an influenza A virus strain of the H1 subtype and an influenza A virus of the H5 subtype.

The foregoing is not to be limited in scope by the specific embodiments described herein. Indeed, various modifications of the antibodies and methods provided herein and their equivalents, in addition to those described herein will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

We claim:

1. A monoclonal antibody that binds to a hemagglutinin of an influenza A virus strain of the H1 subtype, wherein the antibody comprises
   (a) a variable heavy (VH) domain having the amino acid sequence of SEQ ID NO:17;
   (b) a variable light (VL) domain having the amino acid sequence of SEQ ID NO:25;
   (c) a VH domain having the amino acid sequence of SEQ ID NO 17 and a VL domain having the amino acid sequence of SEQ ID NO:25; or
   (d) a VH complementarity determining region (CDR)1, VH CDR2, a VH CDR3 domain, a VL CDR1, a VL CDR2, and a VL CDR3 having the amino acid sequences of SEQ ID NO:19, 21, 23, 27, 29 and 31, respectively.

2. A humanized antibody that binds to a hemagglutinin of an influenza A virus strain of subtype H1, the antibody comprising a VH complementarity determining region (CDR)1, VH CDR2, a VH CDR3 domain, a VL CDR1, a VL CDR2, and a VL CDR3 having the amino acid sequences of SEQ ID NO:19, 21, 23, 27, 29 and 31, respectively.

3. The antibody of claim 1, wherein the influenza A virus strain is A/USSR/92/77 (H1), A/Texas/36/91 (H1), A/New Caledonia/20/99 (H1), rA/California/04/09 (H1), or A/Solomon Islands/06 (H1).

4. The antibody of claim 1, wherein the antibody binds to a hemagglutinin from an influenza A virus strain of the H5 subtype.

5. A composition comprising the antibody of claim 1.

6. A composition comprising the antibody of claim 2.

7. The antibody of claim 1, wherein the antibody is conjugated or fused to a detectable agent or therapeutic agent.

8. A kit comprising the antibody of claim 1.

9. A method of inhibiting an influenza A virus subtype H1 comprising administering to a subject the antibody of claim 1.

10. A method of detecting a strain of influenza A virus of the H1 subtype comprising: (a) assaying for the level of an influenza virus HA in cells or a tissue sample of a subject using the antibody of claim 1; and (b) comparing the level of the influenza virus HA assayed in (a) with the level of the influenza virus HA in normal tissue samples not infected with influenza virus, wherein an increase in the assayed level of influenza virus HA compared to the control level of the influenza virus antigen is indicative of the presence of a strain of influenza A virus of the H1 subtype.

11. The method of claim 9, wherein the strain of influenza A virus of the H1 subtype is A/USSR/92/77 (H1), A/Texas/36/91 (H1), A/New Caledonia/20/99 (H1), rA/California/04/09 (H1), or A/Solomon Islands/06 (H1).

12. A method of detecting a strain of influenza A virus of the H5 subtype comprising: (a) assaying for the level of an influenza virus HA in cells or a tissue sample of a subject using the antibody of claim 4; and (b) comparing the level of the influenza virus HA assayed in (a) with the level of the influenza virus HA in normal tissue samples not infected with influenza virus, wherein an increase in the assayed level of influenza virus HA compared to the control level of the influenza virus antigen is indicative of the presence of a strain of influenza A virus of the H5 subtype.

13. The method of claim 12, wherein the strain of influenza A virus of the H5 subtype is rA/Vietnam/1203/04 (H5).

14. A method for inhibiting an influenza A virus subtype H5 comprising administering to a subject the antibody of claim 1.

15. A method for inhibiting an influenza A virus subtype H1 and an influenza A virus subtype H5 comprising administering to a subject the antibody of claim 1.

16. The method of claim 9, wherein the subject is a human.

17. The method of claim 14, wherein the subject is a human.

18. The method of claim 15, wherein the subject is a human.

19. The method of claim 15, wherein the strain of influenza A virus of the H1 subtype is A/USSR/92/77 (H1), A/Texas/36/91 (H1), A/New Caledonia/20/99 (H1), rA/California/04/09 (H1), or A/Solomon Islands/06 (H1).

* * * * *

SEQUENCE LISTING

```
<160> NUMBER OF SEQ ID NOS: 36

<210> SEQ ID NO 1
<211> LENGTH: 381
<212> TYPE: DNA
<213> ORGANISM: Aritificial Sequence
<220> FEATURE:
<223> OTHER INFORMATION: variable heavy chain region of the monoclonal
      antibody GG3

<400> SEQUENCE: 1
cagatccagt tggtgcagtc tggacctgag ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ataaacatct acagtggaga gtcaacatat     180
gttgatgact tcacgggacg gtttgccttc tctttggaaa cctctgccag cactgcctat     240
ttgcagatca acaacctcaa aaatgaggac atggctacat atttctgtgc aagatctggg     300
gatactatga ttacggcggg acggtccttc tttgctatgg actactgggg tcaaggaacc     360
tcagtcaccg tctcctcagc c                                               381

<210> SEQ ID NO 2
<211> LENGTH: 75
<212> TYPE: DNA
<213> ORGANISM: Aritificial Sequence
<220> FEATURE:
<223> OTHER INFORMATION: VH FR1 region of the monoclonal antibody GG3

<400> SEQUENCE: 2
cagatccagt tggtgcagtc tggacctgag ctgaagaagc ctggagagac agtcaagatc      60
tcctgcaagg cttct                                                       75

<210> SEQ ID NO 3
<211> LENGTH: 24
<212> TYPE: DNA
<213> ORGANISM: Aritificial Sequence
<220> FEATURE:
<223> OTHER INFORMATION: VH CDR1 region of the monoclonal antibody GG3

<400> SEQUENCE: 3
gggtatacct tcacaaacta tgga                                             24

<210> SEQ ID NO 4
<211> LENGTH: 51
<212> TYPE: DNA
<213> ORGANISM: Aritificial Sequence
<220> FEATURE:
<223> OTHER INFORMATION: VH FR2 region of the monoclonal antibody GG3

<400> SEQUENCE: 4
atgaactggg tgaagcaggc tccaggaaag ggtttaaagt ggatgggctg g               51
```

```
<210> SEQ ID NO 5
<211> LENGTH: 24
<212> TYPE: DNA
<213> ORGANISM: Aritificial Sequence
<220> FEATURE:
<223> OTHER INFORMATION: VH CDR2 region of the monoclonal antibody GG3

<400> SEQUENCE: 5
ataaacatct acagtggaga gtca                                            24

<210> SEQ ID NO 6
<211> LENGTH: 114
<212> TYPE: DNA
<213> ORGANISM: Aritificial Sequence
<220> FEATURE:
<223> OTHER INFORMATION: VH FR3 region of the monoclonal antibody GG3

<400> SEQUENCE: 6
acatatgttg atgacttcac gggacggttt gccttctctt tggaaacctc tgccagcact     60
gcctatttgc agatcaacaa cctcaaaaat gaggacatgg ctacatattt ctgt          114

<210> SEQ ID NO 7
<211> LENGTH: 57
<212> TYPE: DNA
<213> ORGANISM: Aritificial Sequence
<220> FEATURE:
<223> OTHER INFORMATION: VH CDR3 region of the monoclonal antibody GG3

<400> SEQUENCE: 7
gcaagatctg gggatactat gattacggcg ggacggtcct tctttgctat ggactac        57

<210> SEQ ID NO 8
<211> LENGTH: 36
<212> TYPE: DNA
<213> ORGANISM: Aritificial Sequence
<220> FEATURE:
<223> OTHER INFORMATION: VH FR4 region of the monoclonal antibody GG3

<400> SEQUENCE: 8
tggggtcaag gaacctcagt caccgtctcc tcagcc                               36

<210> SEQ ID NO 9
<211> LENGTH: 322
<212> TYPE: DNA
<213> ORGANISM: Aritificial Sequence
<220> FEATURE:
<223> OTHER INFORMATION: variable light chain region of the monoclonal
      antibody GG3

<400> SEQUENCE: 9
gacatccaga tgacccagtc tccatcctcc ttatctgcct ctctgggaga aagagtcagt     60
ctcacttgtc gggcaagtca ggaaattagt ggttacttaa gctggcttca gcagaaacca   120
gatggaacta ttaaacgcct gatctacgcc gcatccactt tagattctgg tgtcccaaaa   180
aggttcagtg gcagtaggtc tgggtcagat tattctctct ccatcagcag ccttgagtct   240
gaagattttg cagactatta ctgtcttcaa tatgctaatt atccgtggtc gttcggtgga   300
ggcaccaagc tggaaatcaa ac                                           322

<210> SEQ ID NO 10
<211> LENGTH: 78
<212> TYPE: DNA
<213> ORGANISM: Aritificial Sequence
<220> FEATURE:
<223> OTHER INFORMATION: VL FR1 region of the monoclonal antibody GG3
```

```
<400> SEQUENCE: 10
gacatccaga tgacccagtc tccatcctcc ttatctgcct ctctgggaga aagagtcagt    60
ctcacttgtc gggcaagt                                                 78

<210> SEQ ID NO 11
<211> LENGTH: 18
<212> TYPE: DNA
<213> ORGANISM: Aritificial Sequence
<220> FEATURE:
<223> OTHER INFORMATION: VL CDR1 region of the monoclonal antibody GG3

<400> SEQUENCE: 11
caggaaatta gtggttac                                                 18

<210> SEQ ID NO 12
<211> LENGTH: 51
<212> TYPE: DNA
<213> ORGANISM: Aritificial Sequence
<220> FEATURE:
<223> OTHER INFORMATION: VL FR2 region of the monoclonal antibody GG3

<400> SEQUENCE: 12
ttaagctggc ttcagcagaa accagatgga actattaaac gcctgatcta c            51

<210> SEQ ID NO 13
<211> LENGTH: 9
<212> TYPE: DNA
<213> ORGANISM: Aritificial Sequence
<220> FEATURE:
<223> OTHER INFORMATION: VL CDR2 region of the monoclonal antibody GG3

<400> SEQUENCE: 13 gccgcatcc                                                            9

<210> SEQ ID NO 14
<211> LENGTH: 108
<212> TYPE: DNA
<213> ORGANISM: Aritificial Sequence
<220> FEATURE:
<223> OTHER INFORMATION: VL FR3 region of the monoclonal antibody GG3

<400> SEQUENCE: 14
actttagatt ctggtgtccc aaaaaggttc agtggcagta ggtctgggtc agattattct    60
ctctccatca gcagccttga gtctgaagat tttgcagact attactgt               108

<210> SEQ ID NO 15
<211> LENGTH: 27
<212> TYPE: DNA
<213> ORGANISM: Aritificial Sequence
<220> FEATURE:
<223> OTHER INFORMATION: VL CDR3 region of the monoclonal antibody GG3

<400> SEQUENCE: 15
cttcaatatg ctaattatcc gtggtcg                                       27

<210> SEQ ID NO 16
<211> LENGTH: 31
<212> TYPE: DNA
<213> ORGANISM: Aritificial Sequence
<220> FEATURE:
<223> OTHER INFORMATION: VL FR4 region of the monoclonal antibody GG3

<400> SEQUENCE: 16
```
ttcggtggag gcaccaagct ggaaatcaaa c    31

```
<210> SEQ ID NO 17
<211> LENGTH: 127
<212> TYPE: PRT
<213> ORGANISM: Artificial Sequence
<220> FEATURE:
<223> OTHER INFORMATION: variable heavy chain region of the monoclonal
      antibody GG3

<400> SEQUENCE: 17
```

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Ile Tyr Ser Gly Glu Ser Tyr Val Asp Asp Phe
    50                  55                  60

Thr Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Ser Gly Asp Thr Met Ile Thr Ala Gly Arg Ser Phe Phe Ala
            100                 105                 110

Met Asp Tyr Trp Gly Gln Gly Thr Ser Val Thr Val Ser Ser Ala
        115                 120                 125

```
<210> SEQ ID NO 18
<211> LENGTH: 25
<212> TYPE: PRT
<213> ORGANISM: Artificial Sequence
<220> FEATURE:
<223> OTHER INFORMATION: VH FR1 region of the monoclonal antibody GG3

<400> SEQUENCE: 18
```

Gln Ile Gln Leu Val Gln Ser Gly Pro Glu Leu Lys Lys Pro Gly Glu
1               5                   10                  15

Thr Val Lys Ile Ser Cys Lys Ala Ser
            20                  25

```
<210> SEQ ID NO 19
<211> LENGTH: 8
<212> TYPE: PRT
<213> ORGANISM: Artificial Sequence
<220> FEATURE:
<223> OTHER INFORMATION: VH CDR1 region of the monoclonal antibody GG3

<400> SEQUENCE: 19
```

Gly Tyr Thr Phe Thr Asn Tyr Gly
1               5

```
<210> SEQ ID NO 20
<211> LENGTH: 17
<212> TYPE: PRT
<213> ORGANISM: Artificial Sequence
<220> FEATURE:
<223> OTHER INFORMATION: VH FR2 region of the monoclonal antibody GG3

<400> SEQUENCE: 20
```

Met Asn Trp Val Lys Gln Ala Pro Gly Lys Gly Leu Lys Trp Met Gly
1               5                   10                  15

Trp

```
<210> SEQ ID NO 21
<211> LENGTH: 8
<212> TYPE: PRT
<213> ORGANISM: Artificial Sequence
<220> FEATURE:
<223> OTHER INFORMATION: VH CDR2 region of the monoclonal antibody GG3

<400> SEQUENCE: 21

Ile Asn Ile Tyr Ser Gly Glu Ser
1               5

<210> SEQ ID NO 22
<211> LENGTH: 38
<212> TYPE: PRT
<213> ORGANISM: Artificial Sequence
<220> FEATURE:
<223> OTHER INFORMATION: VH FR3 region of the monoclonal antibody GG3

<400> SEQUENCE: 22

Thr Tyr Val Asp Asp Phe Thr Gly Arg Phe Ala Phe Ser Leu Glu Thr
1               5                   10                  15

Ser Ala Ser Thr Ala Tyr Leu Gln Ile Asn Asn Leu Lys Asn Glu Asp
            20                  25                  30

Met Ala Thr Tyr Phe Cys
        35

<210> SEQ ID NO 23
<211> LENGTH: 19
<212> TYPE: PRT
<213> ORGANISM: Artificial Sequence
<220> FEATURE:
<223> OTHER INFORMATION: VH CDR3 region of the monoclonal antibody GG3

<400> SEQUENCE: 23

Ala Arg Ser Gly Asp Thr Met Ile Thr Ala Gly Arg Ser Phe Phe Ala
1               5                   10                  15

Met Asp Tyr

<210> SEQ ID NO 24
<211> LENGTH: 12
<212> TYPE: PRT
<213> ORGANISM: Artificial Sequence
<220> FEATURE:
<223> OTHER INFORMATION: VH FR4 region of the monoclonal antibody GG3

<400> SEQUENCE: 24

Trp Gly Gln Gly Thr Ser Val Thr Val Ser Ser Ala
1               5                   10

<210> SEQ ID NO 25
<211> LENGTH: 107
<212> TYPE: PRT
<213> ORGANISM: Artificial Sequence
<220> FEATURE:
<223> OTHER INFORMATION: variable light chain region of the monoclonal
      antibody GG3

<400> SEQUENCE: 25

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30
```

```
Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
 50                  55                  60

Ser Arg Ser Gly Ser Asp Tyr Ser Leu Ser Ile Ser Ser Leu Glu Ser
 65                  70                  75                  80

Glu Asp Phe Ala Asp Tyr Tyr Cys Leu Gln Tyr Ala Asn Tyr Pro Trp
                 85                  90                  95

Ser Phe Gly Gly Gly Thr Lys Leu Glu Ile Lys
            100                 105

<210> SEQ ID NO 26
<211> LENGTH: 26
<212> TYPE: PRT
<213> ORGANISM: Artificial Sequence
<220> FEATURE:
<223> OTHER INFORMATION: VL FR1 region of the monoclonal antibody GG3

<400> SEQUENCE: 26

Asp Ile Gln Met Thr Gln Ser Pro Ser Ser Leu Ser Ala Ser Leu Gly
 1               5                  10                  15

Glu Arg Val Ser Leu Thr Cys Arg Ala Ser
            20                  25

<210> SEQ ID NO 27
<211> LENGTH: 6
<212> TYPE: PRT
<213> ORGANISM: Artificial Sequence
<220> FEATURE:
<223> OTHER INFORMATION: VL CDR1 chain region of the monoclonal antibody
      GG3

<400> SEQUENCE: 27

Gln Glu Ile Ser Gly Tyr
 1               5

<210> SEQ ID NO 28
<211> LENGTH: 17
<212> TYPE: PRT
<213> ORGANISM: Artificial Sequence
<220> FEATURE:
<223> OTHER INFORMATION: VL FR2 region of the monoclonal antibody GG3

<400> SEQUENCE: 28

Leu Ser Trp Leu Gln Gln Lys Pro Asp Gly Thr Ile Lys Arg Leu Ile
 1               5                  10                  15

Tyr

<210> SEQ ID NO 29
<211> LENGTH: 3
<212> TYPE: PRT
<213> ORGANISM: Artificial Sequence
<220> FEATURE:
<223> OTHER INFORMATION: VL CDR2 region of the monoclonal antibody GG3

<400> SEQUENCE: 29

Ala Ala Ser
 1

<210> SEQ ID NO 30
<211> LENGTH: 36
<212> TYPE: PRT
<213> ORGANISM: Artificial Sequence
<220> FEATURE:
```

```
<223> OTHER INFORMATION: VL FR3 region of the monoclonal antibody GG3

<400> SEQUENCE: 30

Thr Leu Asp Ser Gly Val Pro Lys Arg Phe Ser Gly Ser Arg Ser Gly
1               5                   10                  15

Ser Asp Tyr Ser Leu Ser Ile Ser Ser Leu Glu Ser Glu Asp Phe Ala
            20                  25                  30

Asp Tyr Tyr Cys
        35

<210> SEQ ID NO 31
<211> LENGTH: 9
<212> TYPE: PRT
<213> ORGANISM: Artificial Sequence
<220> FEATURE:
<223> OTHER INFORMATION: VL CDR3 region of the monoclonal antibody GG3

<400> SEQUENCE: 31

Leu Gln Tyr Ala Asn Tyr Pro Trp Ser
1               5

<210> SEQ ID NO 32
<211> LENGTH: 10
<212> TYPE: PRT
<213> ORGANISM: Artificial Sequence
<220> FEATURE:
<223> OTHER INFORMATION: VL FR4 region of the monoclonal antibody GG3

<400> SEQUENCE: 32

Phe Gly Gly Gly Thr Lys Leu Glu Ile Lys
1               5                   10

<210> SEQ ID NO 33
<211> LENGTH: 180
<212> TYPE: PRT
<213> ORGANISM: Artificial Sequence
<220> FEATURE:
<223> OTHER INFORMATION: variable heavy chain region of antibody GG3
<220> FEATURE:
<221> NAME/KEY: misc_feature
<222> LOCATION: (177)..(177)
<223> OTHER INFORMATION: Xaa can be any naturally occurring amino acid

<400> SEQUENCE: 33

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Ile Tyr Ser Gly Glu Ser Thr Tyr Val Asp Asp Phe
    50                  55                  60

Thr Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Ser Gly Asp Thr Met Ile Thr Ala Gly Arg Ser Phe Phe Ala
            100                 105                 110

Met Asp Tyr Trp Gly Gln Gly Thr Ser Val Thr Val Ser Ser Ala Lys
        115                 120                 125

Thr Thr Ala Pro Ser Val Tyr Pro Leu Ala Pro Val Cys Gly Asp Thr
    130                 135                 140
```

```
Thr Gly Ser Ser Val Thr Leu Gly Cys Leu Val Lys Glu Gly Arg Ile
145                 150                 155                 160

Pro Gln Trp Ile Ser Ser Leu Ser Ile Pro Ser Thr Ser Arg Gly Ala
            165                 170                 175

Xaa Asp Pro Arg
        180

<210> SEQ ID NO 34
<211> LENGTH: 542
<212> TYPE: DNA
<213> ORGANISM: Artificial Sequence
<220> FEATURE:
<223> OTHER INFORMATION: variable heavy chain region of antibody GG3
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (529)..(531)
<223> OTHER INFORMATION: n is a, c, g, or t

<400> SEQUENCE: 34
cagatccagt tggtgcagtc tggacctgag ctgaagaagc tggagagac agtcaagatc      60 tcctgcaagg cttctgggta taccttcaca aactatggaa tgaactgggt gaagcaggct    120
ccaggaaagg gtttaaagtg gatgggctgg ataaacatct acagtggaga gtcaacatat    180
gttgatgact tcacgggacg gtttgccttc tctttggaaa cctctgccag cactgcctat    240
ttgcagatca caaccctcaa aaatgaggac atggctacat atttctgtgc aagatctggg    300
gatactatga ttacggcggg acggtccttc tttgctatgg actactgggg tcaaggaacc    360
tcagtcaccg tctcctcagc caaaacaaca gccccatcgg tctatccact ggcccctgtg    420
tgtggagata caactggctc ctcggtgact ctaggatgcc tggtcaagga agggcgaatt    480
ccacagtgga tatcaagctt atcgataccg tcgacntcga gggggggccnn ngacccacgt   540 ct                                                                  542

<210> SEQ ID NO 35
<211> LENGTH: 160
<212> TYPE: PRT
<213> ORGANISM: Artificial Sequence
<220> FEATURE:
<223> OTHER INFORMATION: variable light chain region of antibody GG3
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa is Ser, Pro, Thr, or Ala
<220> FEATURE:
<221> NAME/KEY: misc_feature
<222> LOCATION: (160)..(160)
<223> OTHER INFORMATION: Xaa can be any naturally occurring amino acid

<400> SEQUENCE: 35

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45
```

```
Tyr Ala Ala Ser Thr Leu Asp Ser Gly Val Pro Lys Arg Phe Ser Gly
    50              55                  60

Ser Arg Ser Gly Ser Asp Tyr Ser Leu Ser Ile Ser Ser Leu Glu Ser
65              70                  75                  80

Glu Asp Phe Ala Asp Tyr Tyr Cys Leu Gln Tyr Ala Asn Tyr Pro Trp
                85                  90                  95

Ser Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Lys Gly Glu Phe His Ser Gly
        130                 135                 140

Tyr Gln Ala Tyr Arg Tyr Arg Arg Pro Arg Gly Gly Pro Xaa Xaa Xaa
145                 150                 155                 160

<210> SEQ ID NO 36
<211> LENGTH: 482
<212> TYPE: DNA
<213> ORGANISM: Artificial Sequence
<220> FEATURE:
<223> OTHER INFORMATION: variable light chain region of antibody GG3
<220> FEATURE:
<221> NAME/KEY: misc_feature
<222> LOCATION: (471)..(475)
<223> OTHER INFORMATION: n is a, c, g, or t
<220> FEATURE:
<221> NAME/KEY: misc_feature
<222> LOCATION: (478)..(480)
<223> OTHER INFORMATION: n is a, c, g, or t

<400> SEQUENCE: 36
gacatccaga tgacccagtc tccatcctcc ttatctgcct ctctgggaga aagagtcagt      60
ctcacttgtc gggcaagtca ggaaattagt ggttacttaa gctggcttca gcagaaacca     120
gatggaacta ttaaacgcct gatctacgcc gcatccactt tagattctgg tgtcccaaaa     180
aggttcagtg gcagtaggtc tgggtcagat tattctctct ccatcagcag ccttgagtct     240
gaagattttg cagactatta ctgtcttcaa tatgctaatt atccgtggtc gttcggtgga     300
ggcaccaagc tggaaatcaa acgggctgat gctgcaccaa ctgtatccat cttcccacca     360
tccagtgagc agttaacatc tggaggtgcc tcagtcgtgt gcttcttgaa caagggcgaa     420
ttccacagtg gatatcaagc ttatcgatac cgtcgacctc gagggggcc nnnnncnnn      480 tt                                                                    482
```